US010405936B2

(12) United States Patent
Awtar et al.

(10) Patent No.: US 10,405,936 B2
(45) Date of Patent: *Sep. 10, 2019

(54) PARALLEL KINEMATIC MECHANISMS WITH DECOUPLED ROTATIONAL MOTIONS

(71) Applicant: The Regents of the University of Michigan, Ann Arbor, MI (US)

(72) Inventors: Shorya Awtar, Ann Arbor, MI (US); Jens Nielsen, Traverse, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 274 days.

This patent is subject to a terminal disclaimer.

(21) Appl. No.: 15/054,068

(22) Filed: Feb. 25, 2016

(65) Prior Publication Data
US 2016/0256232 A1 Sep. 8, 2016

Related U.S. Application Data

(63) Continuation-in-part of application No. 14/166,503, filed on Jan. 28, 2014, now Pat. No. 9,675,370, which
(Continued)

(51) Int. Cl.
*A61B 17/00* (2006.01)
*A61B 17/29* (2006.01)
(Continued)

(52) U.S. Cl.
CPC .......... *A61B 34/71* (2016.02); *A61B 17/2909* (2013.01); *A61B 34/75* (2016.02);
(Continued)

(58) Field of Classification Search
CPC ......... A61B 34/71; A61B 34/70; A61B 34/75; A61B 34/77; A61B 34/37; A61B 17/2909;
(Continued)

(56) References Cited

U.S. PATENT DOCUMENTS 3,497,083 A  2/1970  Anderson et al.
4,328,839 A  5/1982  Lyons et al.
(Continued)

FOREIGN PATENT DOCUMENTS

EP  3232951 A2  6/2016
EP  3232952 A1  6/2016
(Continued)

OTHER PUBLICATIONS

Jug et al.; The JPL Serpentine Robot: a 12 DOF System for Inspection (Conference Paper); Proceedings—IEEE International Conference on Robotics and Automation 3: 5 pgs.; Jun. 1995.
(Continued)

*Primary Examiner* — Katrina M Stransky
(74) *Attorney, Agent, or Firm* — Shay Glenn LLP

(57) ABSTRACT

A parallel kinematic mechanism apparatus includes a frame, a handle and an input joint that connects having at least two independent and functionally parallel paths for transmission of motion coupling the handle to the frame. A first path includes a first intermediate body connected to the frame by a first connector and to the handle by a third connector while the second path that is independent from the first path includes a second intermediate body that is connected to the frame by a second connector and to the handle by a fourth connector. The first connector and the fourth connector both allow rotation in a first rotational direction and restrict rotation in a second rotational direction and the second and third connectors allow rotation in the second rotational direction and restrict rotation in the first rotational direction.

32 Claims, 51 Drawing Sheets

Related U.S. Application Data is a continuation of application No. 12/937,523, filed as application No. PCT/US2009/040353 on Apr. 13, 2009, now Pat. No. 8,668,702.

(60) Provisional application No. 61/044,168, filed on Apr. 11, 2008.

(51) Int. Cl.
*A61B 34/00* (2016.01)
*A61B 34/30* (2016.01)

(52) U.S. Cl.
CPC .... *A61B 34/77* (2016.02); *A61B 2017/00323* (2013.01); *A61B 2017/00424* (2013.01); *A61B 2017/00442* (2013.01); *A61B 2017/00464* (2013.01); *A61B 2017/2917* (2013.01); *A61B 2017/2918* (2013.01); *A61B 2017/2929* (2013.01); *A61B 2017/2931* (2013.01); *A61B 2017/2937* (2013.01); *A61B 2017/2939* (2013.01); *A61B 2017/2944* (2013.01); *A61B 2034/306* (2016.02)

(58) Field of Classification Search
CPC .... A61B 2034/306; A61B 2017/00323; A61B 2017/00424; A61B 2017/00442; A61B 2017/00464; A61B 2017/2917; A61B 2017/2929; A61B 2017/2931; A61B 2017/2937; A61B 2017/2939; A61B 2017/2944; B25J 13/02
See application file for complete search history.

(56) References Cited

U.S. PATENT DOCUMENTS

| | | |
|---|---|---|
| 4,466,649 A | 8/1984 | Ozawa |
| 4,568,311 A | 2/1986 | Miyake |
| 4,712,545 A | 12/1987 | Honkanen |
| 4,750,475 A | 6/1988 | Yoshihashi |
| 4,754,909 A | 7/1988 | Barker et al. |
| 4,950,273 A | 8/1990 | Briggs |
| 5,021,969 A | 6/1991 | Okamura et al. |
| 5,069,596 A | 12/1991 | Mueller et al. |
| 5,147,357 A | 9/1992 | Rose et al. |
| 5,209,747 A | 5/1993 | Knoepfler |
| 5,297,443 A | 3/1994 | Wentz |
| 5,317,952 A | 6/1994 | Immega |
| 5,323,570 A | 6/1994 | Kuhlman et al. |
| 5,330,502 A | 7/1994 | Hassler et al. |
| 5,350,391 A | 9/1994 | Iacovelli |
| 5,368,600 A | 11/1994 | Failla et al. |
| 5,374,277 A | 12/1994 | Hassler |
| 5,454,827 A | 10/1995 | Aust et al. |
| 5,456,695 A | 10/1995 | Dallemagne |
| 5,549,637 A | 8/1996 | Crainich |
| 5,599,151 A | 2/1997 | Daum et al. |
| 5,620,415 A | 4/1997 | Lucey et al. |
| 5,626,608 A | 5/1997 | Cuny et al. |
| 5,683,412 A | 11/1997 | Scarfone |
| 5,713,505 A | 2/1998 | Huitema |
| 5,716,352 A | 2/1998 | Viola et al. |
| 5,735,874 A | 4/1998 | Measamer et al. |
| 5,782,748 A | 7/1998 | Palmer et al. |
| 5,807,376 A | 9/1998 | Viola et al. |
| 5,817,084 A | 10/1998 | Jensen |
| 5,820,009 A | 10/1998 | Melling et al. |
| 5,853,412 A | 12/1998 | Mayenberger |
| 5,860,995 A | 1/1999 | Berkelaar |
| 5,908,436 A | 6/1999 | Cuschieri et al. |
| 6,088,020 A | 7/2000 | Morley et al. |
| 6,270,453 B1 | 8/2001 | Sakai |
| 6,309,403 B1 | 10/2001 | Minor et al. |
| 6,312,435 B1 | 11/2001 | Wallace et al. |
| 6,330,837 B1 | 12/2001 | Charles et al. |
| 6,714,839 B2 | 3/2004 | Salisbury et al. |
| 6,853,879 B2 | 2/2005 | Sunaoshi |
| 6,858,005 B2 | 2/2005 | Ohline et al. |
| 6,889,116 B2 | 5/2005 | Jinno |
| 6,994,716 B2 | 2/2006 | Jinno et al. |
| 7,101,363 B2 | 9/2006 | Nishizawa et al. |
| 7,147,650 B2 | 12/2006 | Lee |
| 7,553,275 B2 | 6/2009 | Padget et al. |
| 7,608,083 B2 | 10/2009 | Lee et al. |
| 7,708,756 B2 | 5/2010 | Nobis et al. |
| 7,736,254 B2 | 6/2010 | Schena |
| 7,862,554 B2 | 1/2011 | Hegeman et al. |
| 8,029,531 B2 | 10/2011 | Lee et al. |
| 8,365,633 B2 | 2/2013 | Simaan et al. |
| 8,425,408 B2 | 4/2013 | Boulais et al. |
| 8,465,475 B2 | 6/2013 | Isbell |
| 8,528,440 B2 | 9/2013 | Morley et al. |
| 8,540,748 B2 | 9/2013 | Murphy et al. |
| 8,551,076 B2 | 10/2013 | Duval et al. |
| 8,603,135 B2 | 12/2013 | Mueller |
| 8,668,702 B2 * | 3/2014 | Awtar ................ A61B 17/2909 294/111 |
| 8,672,206 B2 | 3/2014 | Aranyi et al. |
| 8,764,448 B2 | 7/2014 | Yang et al. |
| 8,992,422 B2 | 3/2015 | Spivey et al. |
| 9,161,771 B2 | 10/2015 | Steger |
| 9,220,398 B2 | 12/2015 | Woodley et al. |
| 9,675,370 B2 * | 6/2017 | Awtar ................ A61B 17/2909 |
| 9,696,700 B2 | 7/2017 | Beira et al. |
| 2001/0031983 A1 | 10/2001 | Brock et al. |
| 2003/0036748 A1 | 2/2003 | Cooper et al. |
| 2003/0135203 A1 | 7/2003 | Wang et al. |
| 2003/0176880 A1 | 9/2003 | Long et al. |
| 2003/0176948 A1 | 9/2003 | Green |
| 2004/0023616 A1 | 2/2004 | Straub et al. |
| 2004/0138700 A1 | 7/2004 | Cooper et al. |
| 2004/0236316 A1 | 11/2004 | Danitz et al. |
| 2004/0253079 A1 | 12/2004 | Sanchez |
| 2005/0004431 A1 | 1/2005 | Kogasaka et al. |
| 2005/0038469 A1 | 2/2005 | Lang |
| 2005/0107667 A1 | 5/2005 | Danitz et al. |
| 2006/0111210 A1 | 5/2006 | Hinman |
| 2006/0111616 A1 | 5/2006 | Danitz |
| 2006/0259073 A1 | 11/2006 | Miyamoto et al. |
| 2006/0282063 A1 | 12/2006 | Gotani |
| 2007/0021738 A1 | 1/2007 | Hasser et al. |
| 2007/0078565 A1 | 4/2007 | Ghodoussi et al. |
| 2008/0039256 A1 | 2/2008 | Jinno et al. |
| 2008/0065098 A1 | 3/2008 | Larkin |
| 2008/0177285 A1 | 7/2008 | Brock et al. |
| 2009/0192511 A1 | 7/2009 | Haffenreffer |
| 2010/0004606 A1 | 1/2010 | Hansen et al. |
| 2010/0016853 A1 | 1/2010 | Burbank |
| 2010/0030018 A1 | 2/2010 | Fortier et al. |
| 2010/0056863 A1 | 3/2010 | Dejima et al. |
| 2010/0234831 A1 | 9/2010 | Hinman et al. |
| 2010/0249497 A1 | 9/2010 | Peine et al. |
| 2011/0024145 A1 | 2/2011 | Click et al. |
| 2011/0118707 A1 | 5/2011 | Burbank |
| 2011/0152881 A1 | 6/2011 | Conner et al. |
| 2011/0152922 A1 | 6/2011 | Jeong |
| 2012/0095298 A1 | 4/2012 | Stefanchik et al. |
| 2012/0118097 A1 | 5/2012 | Ilch |
| 2012/0186383 A1 | 7/2012 | Schvalb et al. |
| 2012/0277762 A1 | 11/2012 | Lathrop et al. |
| 2013/0012958 A1 | 1/2013 | Marczyk et al. |
| 2013/0023868 A1 | 1/2013 | Worrell et al. |
| 2013/0023974 A1 | 1/2013 | Amrani |
| 2013/0066334 A1 * | 3/2013 | Schoepp ............ A61B 17/3403 606/130 |
| 2013/0172860 A1 | 7/2013 | Szewczyk et al. |
| 2013/0224710 A1 * | 8/2013 | Yang .................... G09B 23/28 434/262 |
| 2013/0239734 A1 | 9/2013 | Hinman |
| 2014/0135805 A1 | 5/2014 | Windgassen et al. |
| 2014/0142595 A1 | 5/2014 | Awtar et al. |
| 2014/0371532 A1 | 12/2014 | Trovato |
| 2015/0164601 A1 | 6/2015 | Sholev |
| 2015/0230697 A1 | 8/2015 | Phee et al. |

(56) References Cited

U.S. PATENT DOCUMENTS

| | | |
|---|---|---|
| 2016/0135830 A1 | 5/2016 | Volkmer et al. |
| 2016/0291383 A1 | 10/2016 | Han et al. |
| 2017/0245954 A1 | 8/2017 | Beira |
| 2017/0360522 A1 | 12/2017 | Beira et al. |
| 2018/0000318 A9 | 1/2018 | Rogers et al. |
| 2018/0049842 A1 | 2/2018 | Bowles et al. |
| 2018/0125519 A1 | 5/2018 | Beira et al. |
| 2018/0125592 A1 | 5/2018 | Beira |
| 2018/0221045 A1 | 8/2018 | Zimmerman et al. |
| 2018/0289384 A1 | 10/2018 | Bowles et al. |

FOREIGN PATENT DOCUMENTS

| | | |
|---|---|---|
| EP | 3232973 A1 | 6/2016 |
| EP | 3232974 A2 | 6/2016 |
| EP | 3232977 A1 | 6/2016 |
| EP | 3340897 A1 | 3/2017 |
| GB | 0937587 A | 10/1964 |
| GB | 973587 A | 10/1964 |
| GB | 2513326 A | 10/2014 |
| JP | 3-292879 A | 12/1991 |
| JP | 8-84702 A | 4/1996 |
| JP | H09-96146 A | 4/1997 |
| JP | 2002102248 A | 4/2002 |
| JP | 2003061969 A | 3/2003 |
| JP | 2007130485 A | 5/2007 |
| JP | 2009127289 A | 6/2009 |
| JP | 6220085 B2 | 10/2017 |
| WO | WO2006/036067 A2 | 4/2006 |
| WO | WO 2007/137304 A2 | 11/2007 |
| WO | WO2007/146894 A2 | 12/2007 |
| WO | WO2008/020964 A2 | 2/2008 |
| WO | WO2013/027203 A1 | 2/2013 |
| WO | WO2014/033717 A1 | 3/2014 |
| WO | WO2015/125140 A1 | 8/2015 |
| WO | WO2016/063213 A1 | 4/2016 |
| WO | WO2016/161449 A1 | 10/2016 |

OTHER PUBLICATIONS

Wikipedia; Constant Velocity Joint; 6 pgs.; retrieved from the internet (https://en.wikipedia.org/wiki/Constant-velocity_joint) on Dec. 22, 2016.

Sharma et al.; U.S. Appl. No. 15/284,345 entitled "Handle mechanism providing unlimited roll," filed Oct. 3, 2016.

Licht et al.; U.S. Appl. No. 15/286,489 entitled "Medical devices having smoothly articulating multi-cluster joints," filed Oct. 5, 2016.

Zimmerman et al.; U.S. Appl. No. 15/286,547 entitled "End-effector jaw closure transmission system for remote access tools,"filed Oct. 5, 2016.

Do et al.; Adaptive control of position compensation for cable-conduit mechanisms used in flexible surgical robots; Proceedings of the 11th International Conference on Informatics in Control, Automation and Robotics (ICINCO-2014); IEEE; pp. 110-117; Sep. 1, 2014.

Bowles et al.; U.S. Appl. No. 15/130,915 entitled "Attachment apparatus for remote access tools," filed Apr. 15, 2016.

Awtar; U.S. Appl. No. 15/564,112 entitled "Tesion management apparatus for cable-driven transmission," filed Oct. 3, 2017.

Awtar et al.; A minimally invasive surgical tool with enhanced dexterity and intuitive actuation; J. Med. Devices; 4(3); 8 pages; Sep. 10, 2010 (Author's Draft; 12 pages).

Peirs et al.; A flexible distal tip with two degrees of freedom for enhanced dexterity in endoscopic robot surgery; MME'02; The 13th Micromechanics Europe Workshop; Sinaia, Romania; pp. 271-274; Oct. 6-8, 2002.

Simaan et al.; A dexterous system for laryngeal surgery; Proceedings of the 2004 IEEE International Conference on Robotics and Automation; New Orleans, LA.; pp. 351-357; Apr. 2004.

Clement et al.; Design of a Snake-Like Manipulator; Robotics and Autonomous Systems; 6(3); pp. 265-282; Jul. 1990.

Ikuta et al.; Shape Memory Alloy Servo Actuator System With Electric Resistance Feedback and Application for Active Endoscope (conf. paper); 1988 IEEE Int'l Conf. on Robotics and Automation; pp. 427-430; Apr. 24-29, 1988.

Walker et al.; Novel 'Elephants Trunk' Robot; IEEE/ASME International Conference on Advanced Intelligent Mechatronics, AIM; Piscataway, NJ, United States; pp. 410-415; Sep. 19-23, 1999.

Wikipedia; Six-bar linkage; 2 pgs; retrieved from the internet (https://en.wikipedia.org/w/index.php?title=Six-bar_linkage&oldid=670945266) on Apr. 26, 2019.

\* cited by examiner

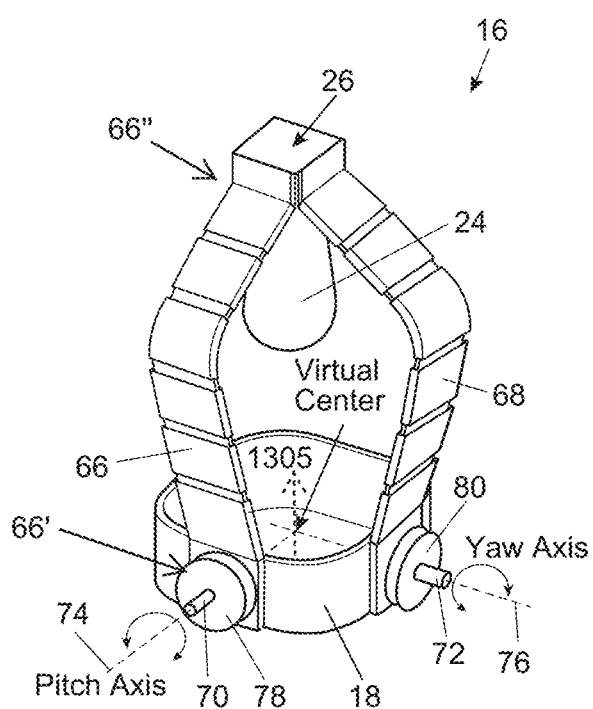
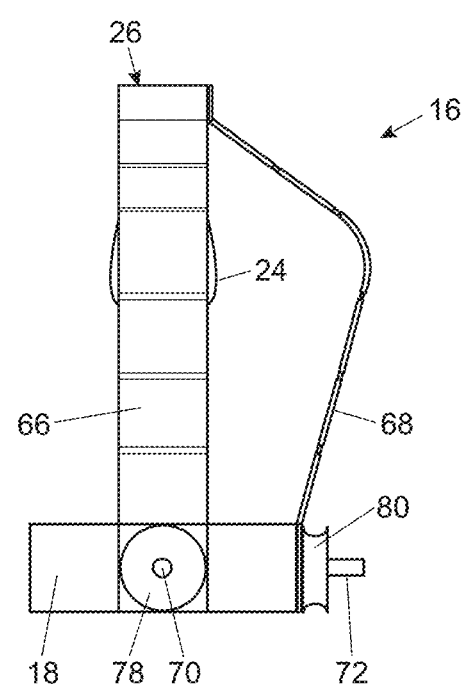
FIGURE 12  FIGURE 13

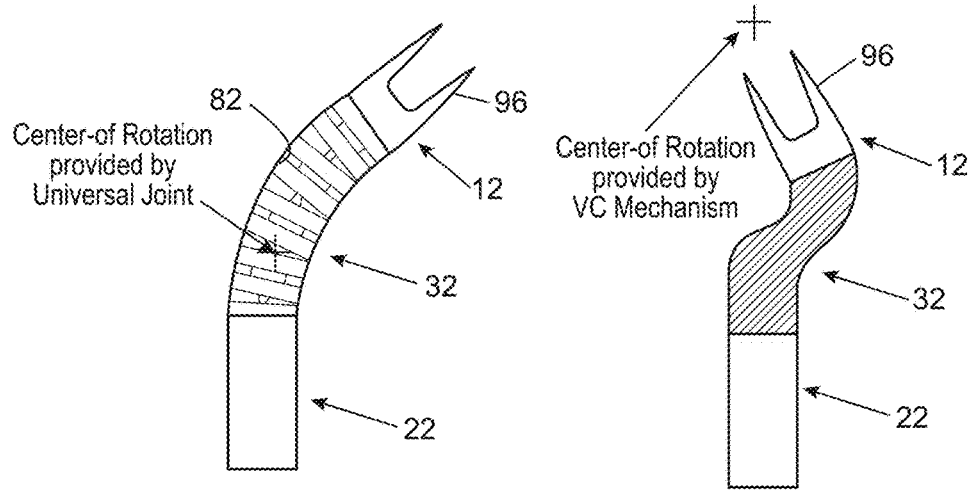
FIGURE 14A  FIGURE 14B
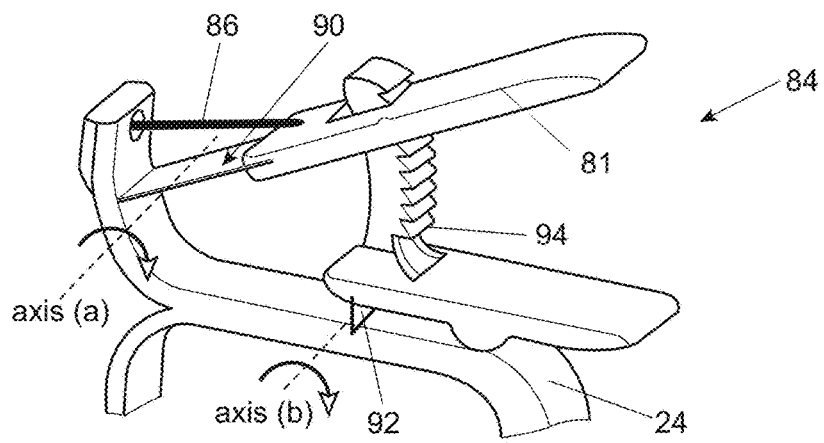
FIGURE 15

BENDING UPWARDS ABOUT THE X DIRECTION IS RESTRICTED BY THE HINGE

SIDE VIEW

BENDING DOWNWARDS ABOUT THE X DIRECTION IS ALLOWED BY THE HINGES AND ACCOMMODATE BY THE CHAMFERS / BEVEL

PARALLEL KINEMATIC MECHANISMS WITH DECOUPLED ROTATIONAL MOTIONS

CROSS REFERENCE TO RELATED APPLICATIONS

This application is a continuation-in-part of U.S. patent application Ser. No. 14/166,503, filed on Jan. 28, 2014, titled "MINIMAL ACCESS TOOL", Publication No. US-2014-0142595-A1, which is a continuation of U.S. patent application Ser. No. 12/937,523, filed on Nov. 30, 2010, titled "MINIMAL ACCESS TOOL", now U.S. Pat. No. 8,668,702, which is a national stage entry of PCT/US2009/040353, filed on Apr. 13, 2009, titled "MINIMAL ACCESS TOOL," Publication No. WO 2009/126955, which claims the benefit of U.S. Provisional Patent Application No. 61/044,168, filed Apr. 11, 2008, titled "MINIMALLY INVASIVE SURGICAL TOOL" each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This invention relates to a minimal access tool, such as for surgery, endoscopy, or other interventions.

BACKGROUND

Devices, including minimally invasive surgical tools, may be controlled by controlling the motion of multiple rigid bodies forming the device. In machines, mechanisms, robots, etc., multiple rigid bodies are often inter-connected such that one body (body 1) has certain motions or degrees of freedom (DoF) with respect to another body (body 2). These motions or degrees of freedom may be accomplished in one of two ways: via serial design (also known as serial kinematic design, serial kinematic chain, and/or serial kinematic mechanism) or via parallel design (also known as parallel kinematic design, parallel kinematic chain, and/or parallel kinematic mechanism).

As used herein, "Degrees of Freedom" (DoF) is a technical term to convey "motions" in an abstract technical and academic sense. In all, there are six independent degrees of freedom possible between two rigid bodies: three translations and three rotations. A joint will allow anywhere between zero and six DoF between the two bodies. For the case when the joint allows zero DoF, this effectively becomes a "fixed joint" where the two bodies are rigidly fused or connected or attached to each other. From a kinematic sense, the two bodies are one and the same. For the case when the joint allows all six DoF, this effectively means that there is no joint, or that the joint really does not constrain any motions between the two bodies. Any practical joint or mechanism allows 1, or 2, or 3, or 4, or 5 DoF between two rigid bodies. If it allows one DoF, then the remaining 5 possible motions are constrained by the joint. If it allows two DoF, then the remaining 4 possible motions are constrained by the joint, etc.

The technical term "kinematics" may refer to the geometric study and description of motion of bodies relative to other bodies. FIGS. 22A and 24 show the difference between a serial kinematic mechanism and a parallel kinematic mechanism. An abstract representation of a serial kinematic mechanism is shown in FIG. 22A, in which body 1 is connected to body 2 via a serial chain of intermediate bodies. If one traces or scribbles a line from body 1 to body 2, there is only one mechanical path (or line) of motion transmission, which makes this a serial design.

Like body 1 and body 2, the intermediate bodies are also rigid, for all practical purposes (nothing ever is perfectly rigid and sometimes some compliance may be intentional). The connectors are simple or complex joints that may allow certain motions and constrain other motions. For convenience, the teems joint and connector may be used interchangeably. Examples of a connector 2305 would be a simple pivot joint (FIG. 23), also known as a hinge, where the pin 2305 would be the connector between the two bodies 2301, 2303 that are pivoted with respect to each other. A hinge with a pin 2305 connecting the two bodies is one example; the intermediate bodies 2301, 2303 may be connected to the objects that are pivoted relative to each other.

A simple joint such as the one shown in FIG. 23 may allow one rotational DoF and constrains the remaining five. Another example would be a prismatic or sliding joint that allows one translational DoF and constrains the remaining five. Another example would be a ball and socket joint that allows three rotational DoF and constrains the remaining three. Alternatively, the connector could be a flexure joint such as a living hinge. These are only a few examples of connectors that are simple joints. In any of these, there are two bodies and some connector in between.

Any mechanism, for example, the serial kinematic mechanism of FIG. 22A, may be part of a larger device, machine, or even mechanism. As shown in FIG. 22B, the serial kinematic mechanism of FIG. 22A is shown to be between two tabs 2201, 2203. But the first tab 2201 may be fused with body 1 (and therefore first tab and body 1 are one and the same), and the second tab 2203 may be fused with body 2 (and therefore second tab and body 2 are one and the same). Body 1 and body 2 can be part of a larger tool, device, machine, or any other mechanism. In that case, the entire mechanism between tabs 2201 and 2203 may be thought of as a complex joint in the large device, machine, or mechanism.

FIG. 24 shows an abstract representation of a parallel kinematic mechanism. In this example, body 1 is connected to body 2 via multiple independent chains of intermediate bodies. Each such chain represents a mechanical path of motion transmission. If one traces possible lines from body 1 to body 2, there is more than one mechanical path, which makes this a parallel design. The connection paths are not parallel in a geometric sense (e.g. two straight lines being parallel such as the opposing sides of a rectangle), but parallel in the kinematic sense, which implies multiple (more than one), independent, non-overlapping chains or paths between body 1 and body 2. The connectors here are simple or complex joints that may allow certain motions and constrain other motions. For convenience, the term joint and connector may be used interchangeably.

Thus, serial and parallel kinematic mechanisms differ in the number of possible connection paths (intermediate rigid members separated by joints) between two tabs or rigid bodies. Although the individual connectors or joints in serial and parallel kinematic mechanisms are similar, their arrangements (linkage, chains, etc.) are different.

Any mechanism, for example, the parallel kinematic mechanism of FIG. 24, may be part of a larger device, machine, or even mechanism. In that case, the entire mechanism between body 1 and body 2 may be thought of as a connector or complex joint, as shown as "New Connector" in FIG. 25.

Even though a mechanism generally comprises multiple joints, there is a certain equivalence between the terms "mechanism" and "joint". Both may refer to an apparatus that allows certain motions or DoF between two bodies and constrains the remaining DoFs. While a joint may be used to refer to a simpler construction, a mechanism may refer to a more complex construction (e.g., which may comprise multiple joints).

Refer to FIG. 25, which is an alternative reproduction of FIG. 24. Everything that lies between body 1 and body 2 (all the intermediate bodies and connectors) may be viewed as a black-box and be termed as one "new" connector or complex joint. Thus, what was viewed as a mechanism in FIG. 24 may also be equivalently viewed as a connector or complex joint in FIG. 25. By the same token, any connector shown in the mechanism of FIG. 22A or FIG. 24 may be a simple joint (such as pivot/pin joint or a prismatic/sliding joint) but can also be a more complex joint or a mechanism in itself.

One example of a serial kinematic mechanism is a universal joint, which may include a rigid body, a pin joint, another rigid body, a second pin joint, and a third rigid body. This entire mechanism (comprising all its rigid bodies and joints) is referred to as a "universal" joint. As used herein, a "joint" refers to a mechanical connection that allows motions as opposed to a fixed joint (such as welded, bolted, screwed, or glued joint). In the latter case, the two bodies become fused with each other and are considered one and the same in the kinematic sense (because there is no relative motion allowed). However, when we refer to "joint" in this document, we mean a connection that allows certain motions, e.g. pin (e.g., hinge) joint, a pivot joint, a universal joint, a ball and socket joint, etc. Thus the referenced joint may interface one body with another in a kinematic sense. Yet another academic term for "joint" is "constraint". Thus, a "connector" or "joint" or "mechanism" or "constraint" allows certain motions or degrees of freedom between two rigid bodies and constrains the rest.

The particular motions that are constrained are also motions that can be transmitted from one rigid body to the other rigid body. That is because since the joint does not allow that particular motion between the two bodies, if one body moves in the constrained direction, it drives along with it the other rigid body as well along that direction. In other words, that particular motion is transmitted from one rigid body to another.

One application area where parallel kinematic mechanisms may be used includes instruments for minimally invasive surgery. Minimally invasive surgical (MIS) and other minimal access procedures are increasing in frequency and becoming more complex, thus demanding improvements in technology to meet the needs of surgeons. In these procedures, generally thin tools are inserted into the body through ports such as trocars or cannulas, which require only small incisions. Motion input from the user, such as a surgeon, is transferred via the tool to the motion of a manipulator or end effector attached to the tool's tip inside the patient's body. This arrangement is used to carry out an operation within the body with the end effector that is controlled from outside the body by a surgeon. This eliminates the need for making large incisions. MIS tools range from simple scissor-like tools to complex robotic systems.

Most traditional tools for use in MIS are mechanical and hand-held, and provide four degrees of freedom (DoF) (three translations and one roll rotation) plus grasping at the end effector, while some newer ones further add up to two DoF (pitch and yaw rotations). These mechanical hand-held tools are inherently capable of force feedback, in general. The traditional mechanical tools are difficult to use because of their lack of dexterity (i.e. the yaw and pitch rotational DoF). While the newer tools are capable of enhanced dexterity given their extra two DoF, they present non-intuitive DoF control (input motion to output motion mapping) schemes that limit user's ability to fully exploit the tool's enhanced dexterity capability. With robotic tools, the user has intuitive control over the dexterity of a tool tip manipulator, the use of electromechanical actuators to produce motion of the tool tip manipulator takes away the mechanical force feedback. In addition, large size, high cost, and limited large-scale maneuverability also reduce the overall functionality of such robotic systems.

Therefore, most existing multiple DoF tools lack the design characteristics to allow for enhanced dexterity as well as desired functionality in a cost effective, compact package. In particular, multiple DoF tools that allow for wrist-like rotations of the tool tip manipulator are important to meet the needs of modern minimal access and MIS procedures, but are not effective unless comfortable, ergonomic, and intuitive control of these additional DoF are ensured.

Examples of serial kinematic mechanisms used in minimally invasive surgical tools may be found in U.S. Pat. No. 5,908,436 to Storz (showing an input joint between a handle and a frame connected by a serial kinematic mechanism) and in U.S. Pat. No. 7,454,268 to Toshiba (also showing a medical device with an input joint between a handle and a frame). In both cases, the input joint is a serial kinematic mechanism. The robotic surgical system shown in U.S. Pat. No. 6,714,839 describes a serial kinematic mechanism as the input joint between a handle and a frame. As used herein a handle is any manual interface (e.g., for fingers, wrist, palm, etc.) and is not limited to controls that are held in the hand. In some of these devices, the frame may refer to a shaft, e.g., tool shaft or an extension of the tool shaft.

In the above cases, the frame is a mechanical reference or a "local ground". It is not necessarily an absolute ground (i.e. attached or bolted to the actual ground). Rather, the frame serves a mechanical reference or local ground for the handle. In the kinematic sense, one may be interested in the motions or DoF of the handle with respect to the frame, and therefore the frame serves as a mechanical reference. Similarly, handle is to be understood in a generic sense, not simply as something to be "held" in the hand; handle could be something that interfaces with the hand, e.g., the fingers, thumb, etc.

In the examples listed above, the handle has at least two rotational DoF (pitch and yaw rotations) with respect to the frame, provided by the input joint. One challenge of using a serial kinematic mechanism design as the input joint of a surgical tool or machine or device is that of transmitting the two rotational DoF from the input joint to another location on the tool or machine or device. For example, the device of U.S. Pat. No. 5,908,436 to Storz or the device of U.S. Pat. No. 7,454,268 to Toshiba has a serial kinematic mechanism as the input joint that provides the handle with two rotational DoFs (pitch and yaw rotations) with respect to the frame. These two DoF are accomplished via a serial kinematic arrangement of two pivot joints with orthogonal rotational axes. In a practical application the handle may be driven by a hand and the two resulting rotations will be available at two pivot joints. While the axis of one pivot joint (i.e. the first axis) is fixed with respect to the frame, the axis of the second pivot joint (i.e. the second axis) is not. Because of the serial kinematic arrangement, the second axis itself rotates with respect to the frame about the first axis. For the tool, device, or machine to be useful, it is generally desirable or required that the two rotations of the input joint be capture and transmitted (in some cases mechanically) to an end effector (such as a grasper, etc.) at some other location on the tool, device, or machine.

In this case, one can capture the rotation about the first axis relatively easily (e.g., by mounting a pulley at this particular pivot joint), or mounting a gear at this pivot joint location that would rotate with respect to frame about the first axis; the resulting axis of rotation of the gear will remain fixed with respect to the frame serving as its ground. This facilitates a variety of mechanical transmission methods/systems to transmit the rotation about first axis to a remotely located end effector which all operate with respect to the same ground reference frame. Unfortunately, since the second axis itself rotates with respect to the frame about the first axis, it does not remain practical or easy to transmit the second rotation to a remote end effector on the frame. Doing so would require designing and constructing a transmission across a moving interface or pivot joint, the first pivot joint in this case. Designing and building a transmission across any moving interface/joint is non-trivial, and adds significant complexity, cost, and the potential for failure. These are some of the biggest limitations of a multi-DoF serial kinematic mechanism design. One way of overcoming the above challenges is to use an electronic transmission rather than mechanical transmission, similar to how a joy-stick (an input interface to many computer controlled tools/devices/machines) works. Instead of mounting a pulley (or other mechanical means for transmission) at the pivot joints in the serial kinematic mechanism, a potentiometer or optical encoder, or any other rotary motion sensor, may be included at the first and second pivot joints. A rotary motion sensor would transduce the rotational motion into an electrical signal with a known relationship between the two. In this case, the entire body of the rotary sensor mounted at the second pivot joint may also rotate about the first axis, but that is not a problem because the rotation information captured by this sensor in the form of an electric signal can be communicated wirelessly or via wires to a computer or other electronic hardware. Wireless does not require any physical transmission components, and so the drawback of the serial kinematic mechanisms described above are no longer relevant. When using wires for electrically transmitting the electric signals generated by the rotary sensor, one simply needs to manage the wire/cables routing across the moving interface/joint (first pivot joint in this case) which is commonly done. Wires can be miniaturized, folded, insulated, and routed in many creative ways that are practical and cost-effective. As a result serial kinematic mechanisms are common input joints or input interfaces for various computer or electronics based devices, but are somewhat challenging for purely mechanical devices.

One can make a similar argument for when a serial kinematic design is used as an output mechanism or output joint of a tool or machine or device. In this arrangement it is important to determine how to transmit power or motion from the frame i.e. reference ground, where it is available, to the mechanism output i.e. handle and route it through a serial kinematic chain, where components or links move with respect to each other. To do this mechanically is very complicated, challenging, and generally impractical. Instead, one can route the power electrically via cables, or hydraulically/pneumatically via hoses routed to the various motors/actuators at each joint in the serial kinematic mechanisms. As a result serial kinematic mechanisms are common in devices/machines where electrical, electromechanical, hydraulic, or pneumatic actuation is involved, but are challenging as output joints of purely mechanical devices/machines. Even in the former case, one drawback of a serial kinematic design is that the multiple actuators in the device/machine are not all mounted on the frame or the reference ground, and instead most move along with the DoFs. This may make the machine large and bulky and require moving cable connections, which add to cost and machine size. Some examples of a serial kinematic design being used as the output mechanism of a machine include earth movers (which may include hydraulic actuators powered by flexible tubing/hoses that can bend and flex and therefore be routed over moving interfaces/joints).

Described herein are parallel kinematic mechanisms, including in particular parallel kinematic mechanisms used as the input joint in surgical devices, which may address the issues raised above.

SUMMARY OF THE DISCLOSURE

In general, described herein are parallel kinematic (PK) mechanisms and apparatuses including them that have at least two rotational degrees of freedom between a handle and a frame. These parallel kinematic mechanisms are based on a constraint map focusing on articulation motion (i.e. two orthogonal rotations). Although the constraint map itself is specific and well-defined, it allows multiple physical embodiments that may look physically different but embody the same basic underlying concept. The particular motions that are constrained between the handle and the frame, according to the constraint map, are also motions that can be transmitted between the handle and the frame. Since a joint that constrains a particular motion does not allow that particular motion between the two bodies, if one body moves in the constrained motion direction, it drives the other body in that motion direction along with it. In other words, that particular motion is transmitted from one body to another.

For example, described herein are parallel kinematic (PK) mechanisms having at least two rotational degrees of freedom between a handle and a frame that include: the frame; the handle; an input joint having at least two independent paths for transmission of motion coupling the handle to the frame, wherein the at least two independent paths comprise a first path and a second path; a first intermediate body in the first path that is connected to the frame by a first connector and to the handle by a third connector; a second intermediate body in the second path that is connected to the frame by a second connector and to the handle by a fourth connector; wherein the first connector and the fourth connector both allow rotation in a first rotational direction and restrict rotation in a second rotational direction; further wherein the second and third connectors allow rotation in the second rotational direction and restrict rotation in the first rotational direction.

As used herein, independent paths for transmission of motion may refer to paths (e.g., connections between the handle and the frame) that may independently transmit mechanical force or motion. As used herein a parallel path refers to the independent and parallel operation of the path with one or more other paths, and does not necessarily refer to the geometric relationship between the paths.

In the apparatuses (e.g., mechanisms, devices, and systems) and methods described herein, when a connector allows rotation in a first rotational direction and restricts rotation in a second rotational direction, the connector typically allows some rotations (or certain motions/DoF) and constraints other rotations (or motions/DoF) between two bodies that the connector is connected between. These rotations (e.g., motions) are relative to or in between the two bodies. For example, two rotational directions, 1 and 2, can be defined with respect to a ground reference such as the frame. When an apparatus (e.g., a minimally invasive device) includes other components that are rigidly coupled to the frame, e.g., a tool shaft, the same definitions for directions 1 and 2 may be used throughout the device, as needed.

In general, the angle between an axis of rotation of the first rotational direction and an axis of rotation of the second rotational direction may be between 30 and 150 degrees, including approximately 90 degrees, or orthogonal. For example, an axis of rotation of the first rotational direction may be orthogonal to an axis of rotation of the second rotational direction.

Any of the apparatuses described herein may include a virtual center of rotation. For example, an axis of rotation of the first rotational direction and an axis of rotation of the second rotational direction may intersect in a virtual center of rotation, wherein the virtual center of rotation is located in a vacant space devoid of any other components of the parallel kinematic mechanism or attached to the parallel kinematic mechanism. The virtual center of rotation may coincide with a center of a user's articulating joint when the user interfaces with the handle. For example, the virtual center of rotation may coincide with a center of a user's wrist joint when the user is holding the handle.

In any of the apparatuses described herein, the parallel kinematic mechanism may be configured as a minimally invasive tool and may include a tool shaft having a proximal end and a distal end. The proximal end of the tool shaft may be connected to the frame. In particular, the tool shaft (e.g., the proximal end) may be rigidly connected to the frame. When the apparatus is configured as a minimally invasive tool, it may also include at least two rotational degrees of freedom output joint between an end effector and the distal end of the tool shaft wherein the output joint is coupled to the input joint via a transmission (e.g., a transmission system) to correlate and transmit the at least two independent paths of the input joint to the at least two rotational degrees of freedom of the output joint. In some variations, when the apparatus is configured as a minimally invasive tool, it may further comprise an end effector connected to the frame via an output joint having at least two rotational degrees of freedom between the end effector and the distal end of the tool shaft. The output joint may be coupled to the input joint via a transmission system to correlate and transmit rotations of the handle with respect to the frame to corresponding rotations of the end effector with respect to the tool shaft.

In operation, the parallel kinematic mechanisms described herein may act in part by separating out the rotations of the handle. For example, two rotations of the handle may be separated and filtered into rotation 1 only at body 1 and rotation 2 only at body 2.

Any of the parallel kinematic mechanisms described herein may include an output wherein the output is coupled to the input joint via a mechanical transmission system configured to correlate and transmit rotations of the first and second intermediate bodies to the output. An output joint may include multiple joints, such as one or more pulleys or links. The output joint may be coupled to the input joint so that the separated and filtered movements (rotations) may be respectively transmitted to components of the output joint. For example, an output may be coupled to the input joint via an electromechanical transmission system configured to correlate and transmit rotations of the first and second intermediate bodies to the output. The electromechanical transmission may include sensors/encoders, which may encode the respective rotations (e.g., pitch, yaw, etc.) from the input joint. Any appropriate transmission or transmission system may be used. For example, the output may be coupled to the input joint via a fluidic transmission configured to correlate and transmit rotations of the first and second intermediate bodies to the output. The fluidic transmission may include hydraulic and/or pneumatic components.

In any of the variations described herein, the frame may be configured to interface with the forearm of a user. Thus, the frame may be coupled to the user's forearm by straps, etc.

The first and second intermediate bodies may be pulleys. In any of the variations described herein, the first connector may be a first pivot joint, the second connector may be a second pivot joint, the third connector may be a first flexure transmission strip and the fourth connector may be a second flexure transmission strip.

The apparatuses described herein may include additional independent paths. For example, the input joint may include a third independent path coupling the handle to the frame, wherein the third independent path operates in parallel with the first and second paths; a third intermediate body in the third independent path that is connected to the frame by a fifth connector and to the handle by a sixth connector; wherein the fifth connector allows rotation in the first rotational direction and restricts rotation in the second rotational direction. Thus, the third independent path may be analogous to the first independent path; a fourth independent path may be analogous to the second independent path.

Any of the apparatuses described herein may also allow translation in another direction. For example, the first path and the second path may allow translation along a third axis. The first path or the second path or both the first path and the second path may constrains rotation about a third axis.

As mentioned, in general, any of the apparatuses described herein may be configured as a minimally invasive tool comprising a tool shaft extending from the frame, an output joint that couples the tool shaft to an end effector and a transmission that couples rotations between the input joint and the output joint.

Another embodiment of the apparatuses described herein may be configured as a parallel kinematic (PK) mechanism having at least two rotational degrees of freedom between a handle and a frame, and may include: the frame; the handle; an input joint having at least two independent paths for transmission of motion coupling the handle to the frame, wherein the at least two independent paths comprise a first path and a second path; a first intermediate body comprising a first pulley in the first path that is connected to the frame by a first connector comprising a first pulley pin and to the handle by a third connector comprising a first transmission strip; a second intermediate body comprising a second pulley in the second path that is connected to the frame by a second connector comprising a second pulley pin and wherein the second intermediate body is connected to the handle by a fourth connector comprising a second transmission strip; wherein the first pulley pin allows rotation in a pitch rotational direction and restricts rotation in a yaw rotational direction, and the second transmission strip is compliant in bending in the pitch direction and has a high stiffness in bending in the yaw direction; further wherein the second pulley pin allows rotation in the yaw rotational direction and restricts rotation in the pitch rotational direction and the first transmission strip is compliant in the yaw direction and has high stiffness in bending in the pitch direction.

The first and second transmission strips may comprise a plurality of rigid segments interconnected in a line by hinged connections. As used herein the phrase "rigid segments interconnected in a line" may refer to a serial connection (in which A is connected to B, B is connected to C, C is connected to D, etc. and A and C connect only through B while A and D connect only through B and C).

In any of these apparatuses, the first and second transmission strips may include a plurality of rigid segments and a plurality of hinges, wherein each rigid segment is hinged to an adjacent rigid segment by a hinge from the plurality of hinges, and wherein each hinge has an axis of rotation that is parallel to an axis of rotation of each hinge in the plurality of hinges. The first and second transmission strips may include a plurality of rigid segments and a plurality of living hinges, wherein each rigid segment is connected to an adjacent rigid segment by a living hinge from the plurality of living hinges, and were in each living hinge has an axis of rotation that is parallel to an axis of rotation of each living hinge in the plurality of living hinges.

A first end of the first transmission strip may be rigidly attached to the handle and an opposite end of the first transmission strip may be rigidly attached to the first pulley; further, the first end of the second transmission strip may be rigidly attached to the handle and an opposite end of the second transmission strip is rigidly attached to the second pulley.

Another embodiment of the parallel kinematic (PK) mechanisms described herein may include: a frame; a handle comprising a plate; an input joint having at least two independent paths for transmission of motion between the handle to the frame, wherein the at least two independent paths comprise a first path and a second path (which may operate in parallel); a first intermediate body comprising a first plate in the first path that is connected to the frame by a first connector comprising a first plurality of transmission strips and to the handle by a third connector comprising a third plurality of transmission strips; a second intermediate body comprising a second plate in the second path that is connected to the frame by a second connector comprising a second plurality of transmission strips and to the handle by a fourth connector comprising a fourth plurality of transmission strips; wherein the first connector and the fourth connector both allow rotation in a pitch rotational direction and restrict rotation in a yaw rotational direction; further wherein the second and third connectors allow rotation in the yaw rotational direction and restrict rotation in the pitch rotational direction.

The first plurality of transmission strips and the fourth plurality of transmission strips may be compliant in bending in the pitch direction and have a high stiffness in bending about the yaw direction and wherein the second plurality of transmission strips and the third plurality of transmission strips may be compliant in bending in the yaw direction and have a high stiffness in bending about the pitch direction.

Each transmission strip in the first plurality of transmission strips may be rigidly attached at a first end to the first intermediate body and rigidly attached at a second end opposite from the first end to the frame. Each transmission strip in the third plurality of transmission strips may be rigidly attached at a first end to the first intermediate body and rigidly attached at a second end, opposite from the first end, to the handle. Similarly, each transmission strip in the second plurality of transmission strips may be rigidly attached at a first end to the second intermediate body and rigidly attached at a second end opposite from the first end, to the frame. Each transmission strip in the fourth plurality of transmission strips may be rigidly attached at a first end to the second intermediate body and rigidly attached at a second end, opposite from the first end, to the handle.

Another embodiment of the parallel kinematic (PK) mechanisms described herein may include: a frame; a handle; an input joint having at least two independent paths for transmission of motion coupling the handle to the frame, wherein the at least two independent paths comprise a first path and a second path (which may operate in parallel); a first intermediate body in the first path that is connected to the frame by a first connector comprising a first pivot joint and to the handle by a third connector comprising a third pivot joint; a second intermediate body in the second path that is connected to the frame by a second connector comprising a second pivot joint, and to the handle by a fourth connector, wherein the fourth connector comprises a flexible torsion shaft; wherein the first connector and the fourth connector both allow rotation in a pitch rotational direction and restrict rotation in a yaw rotational direction; further wherein the second and third connectors allow rotation in the yaw rotational direction and restrict rotation in the pitch rotational direction. The flexible torsional shaft may transmit rotations about its center axis, which corresponds to the yaw direction, while remaining compliant in bending in the pitch rotational direction. In any of these variations, the yaw and pitch rotation directions are defined with respect to the frame, as illustrated herein. The flexible torsional shaft may be rigidly connected to the handle at a first end of the flexible torsional shaft, and rigidly connected to the second intermediate body at a second end of the flexible torsional shaft. The first and second intermediate bodies may comprise pulleys. The first path (e.g., the first and third connectors) may constrain rotation about a roll axis that is orthogonal to both the pitch and yaw axes.

Also described herein is another embodiment of a parallel kinematic (PK) mechanism that includes: a frame; a handle; an input joint having at least two independent paths for transmission of motion coupling the handle to the frame, wherein the at least two independent paths comprise a first path and a second path (which may operate in parallel); a first intermediate body comprising a pitch mount (e.g., pitch support, pitch arch, pitch ring, or any other appropriate shape) in the first path that is connected to the frame by a first connector comprising a pivot joint and to the handle by a third connector comprising a first slider joint; a second intermediate body comprising a yaw mountyaw mount (e.g., yaw support, yaw arch, yaw ring, or any other appropriate shape) in the second path that is connected to the frame by a second connector comprising a pivot joint and the handle by a fourth connector comprising a second slider joint; wherein the first connector and the fourth connector both allow rotation in a pitch rotational direction and restrict rotation in a yaw rotational direction; further wherein the second and third connectors allow rotation in the yaw rotational direction and restrict rotation in the pitch rotational direction. The first intermediate body may comprise a pulley rigidly coupled to the pitch mount and wherein the second intermediate body comprises a yaw pulley rigidly coupled to the yaw mount.

In some variations, the pitch mount of the first intermediate body may comprise a first slot forming the first slider joint within which the handle (or member rigidly extending from the handle, which may form a portion of the handle or may be connected, e.g., rigidly, to the handle) may slide; and further wherein the yaw frame of the second intermediate body may comprise a second slot forming the second slider joint within which the handle or the member rigidly extending from the handle may slide. The handle (or a member rigidly extending from the handle) may be constrained from rotating within the first and second slider joint about a roll axis that is orthogonal to both the pitch and yaw axes.

The first independent path (e.g., the first slider joint) and the second intermediate path independent path (e.g., the second slider joint) may allow the handle or the member rigidly extending from the handle to translate along a roll axis that is orthogonal to both the pitch and yaw axes.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 12 and 13 are perspective and front elevational views, respectively, of a fixed axes VC mechanism according to the present invention;

FIGS. 14A and 14B are front elevational views of a cascaded-disk implementation and a VC mechanism implementation, respectively, of an output joint according to the present invention;

FIG. 15 is a perspective view of a closure mechanism according to the present invention;

34A shows a strip of material prior to forming the living hinge; FIG. 34B shows side view of a transmission strip formed using living hinges, and FIG. 34C is a top view of the transmission strip of FIG. 34B. FIG. 34D is another example of a transmission strip formed to include living hinges between rigid segments.

FIG. 42A shows a side perspective view, FIG. 42B shows a top view, FIG. 42C is a side view and FIG. 42D is a top view of a partially constructed configuration.

FIG. 45A is a top view, FIG. 45B is an enlarged top view, FIG. 45C is a front perspective view, and FIG. 45D is a side view.

In FIG. 56A the handle portion is configured to interface with the user's palm. In FIG. 56B the handle portion is configured to interface with one or more of the user's fingers (e.g., as a ring). In FIG. 56C the handle portion is configured to interface with a user's thumb.

In FIG. 67 a portion of one of the flexible torsional shafts has been made partially transparent to show the flexible torsional shaft.

DETAILED DESCRIPTION

Described herein are parallel kinematic (PK) mechanism apparatuses based on a constraint map focusing on articulation motion (i.e. two orthogonal rotations). As will be described in greater detail below, although the constraint map is specific and well-defined, it serves as the basis for multiple physical embodiments that may look physically different but all incorporate the same basic underlying concept. The apparatuses and methods described herein may embody applications of the parallel kinematic constraint map shown in FIG. 26.

Figure 26:
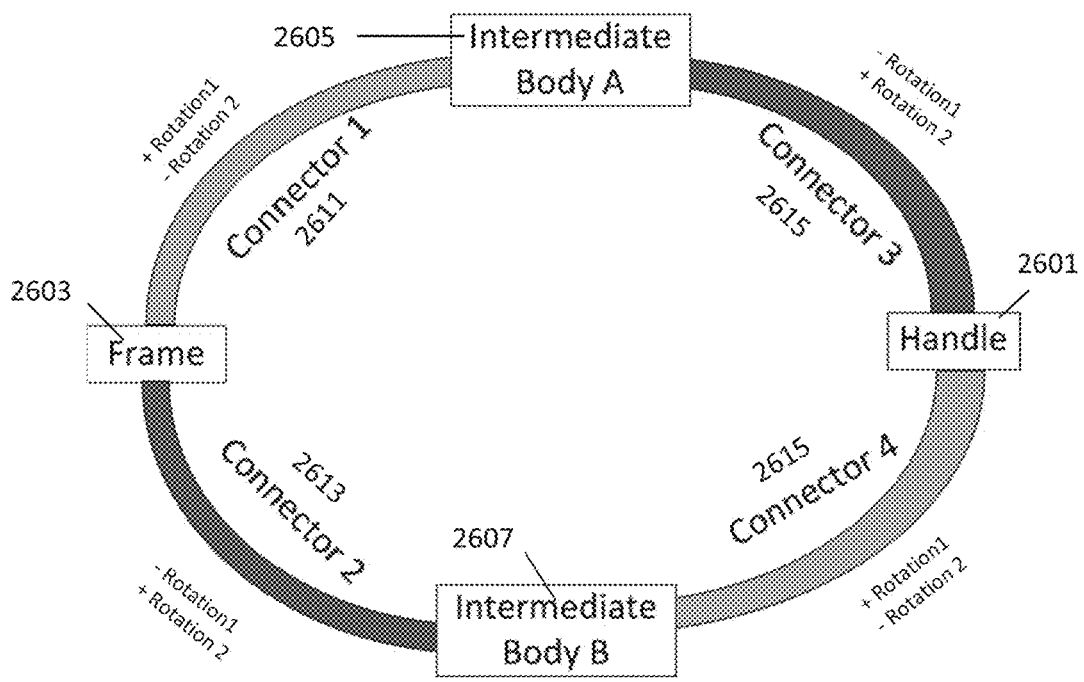
FIG. 26 is an illustration of a core constraint map defining the parallel kinematic mechanisms described herein.

The constraint map shown in FIG. 26 indicates that, for a device such as a minimally invasive surgical tool which includes a frame portion and a handle portion, there may be at least two independent, non-overlapping paths of connection, which make a parallel kinematic arrangement. The frame 2603, handle 2601, intermediate body A 2605, and intermediate body B 2607 may be generally "rigid" (e.g., difficult to bend or deform). Connector 1 (2611), connector 2 (2613), connector 3 (2615), and connector 4 (2617) are joints or connectors, which are also referred to as constraints (hence the name constraint map). Connector 1 2611 allows rotation 1 and restricts (and therefore transmits) rotation 2. In other words, connector 1 is compliant in rotation 1 and stiff in rotation 2. Connector 2, on the other hand, allows rotation 2 and restricts rotation 1. Connector 3 also allows rotation 2 and restricts rotation 1. Connector 4 allows rotation 1 and restricts rotation 2. As explained previously, it is important to note that a connector "transmits" the particular rotation that it "restricts" or "constrains". It may equivalently be said that the connector provides high stiffness along this particular rotation. Similarly, when a connector "allows" a particular rotation, it also means that the connector does not "transmit" this particular rotation, or is compliant along this particular rotation. This arrangement provides at least two rotational degrees of freedom (DoF) at the handle with respect to the frame. Any rotation happens about a rotational axis. Accordingly, one can define that rotation 1 happens about rotational axis 1, and rotation 2 happens about rotational axis 2.

In one specific case, the two rotations can be orthogonal to each other and be defined as yaw and pitch rotations, i.e. rotations about a pitch axis and a yaw axes, respectively, where the pitch and yaw axes are orthogonal to each other. However, the constraint map shown in FIG. 26 is more generally relevant: the two rotational axes need not be called the pitch and yaw axes, and need not be exactly orthogonal (perpendicular to each other) and can instead be at another angle. For example, depending on the application, the range of the angle between the two axes can be approximately from 30 degrees to 150 degrees.

In some variations, the frame may serve as a reference, which means that one may observe/study/discuss the motion of intermediate body A, intermediate body B, and handle with respect to the frame. In another case, one may consider the handle to be reference, which means that one may observe/study/discuss the motion of the remaining bodies with respect to the handle. For much of the discussion in this document, the frame is treated as the reference. Specifically, as used and described herein, rotations (e.g., "rotation 1", "rotation 2", "rotation 3") may be made with respect to the frame.

Using physical connectors that have the attributes described above, the constraint map shown in FIG. 26 may provide the basis for constructing PK mechanisms that exhibit unique and specific functionality. This functionality can be described in two different ways depending on whether the PK mechanism is used as an input interface/mechanism/joint or an output interface/mechanism/joint in a tool, device, or machine, but these functionalities are the consequence of the same construction/structure illustrated.

Considering the case when the PK mechanism is used as an input interface/mechanism/joint: when the handle is rotated about rotational axis 1, this rotation (i.e. rotation 1) is transmitted to intermediate body A via connector 3, which transmits rotation 1. When the handle is rotated about rotational axis 2, this rotation (i.e. rotation 2) is NOT transmitted to intermediate body A because connector 3 allows (and therefore does not transmit) rotation 1. Intermediate body A has the ability to rotate about rotational axis 1 but can't rotate about rotation axis 2, with respect to the frame, because of connector 1. Thus, for any arbitrary combination of rotation 1 and rotation 2 at the handle, only rotation 1 is transmitted to and exhibited by intermediate body A, which does not see any effect of rotation 2.

When the handle is rotated about rotational axis 2, this rotation (i.e. rotation 2) is transmitted to intermediate body B via connector 4, which transmits rotation 2. When the handle is rotated about rotational axis 1, this rotation (i.e. rotation 1) is NOT transmitted to intermediate body B because connector 4 allows (and therefore does not transmit) rotation 2. Intermediate body B has the ability to rotate about rotational axis 2 but can't rotate about rotation axis 1, with respect to the frame, because of connector 2. Thus, for any arbitrary combination of rotation 1 and rotation 2 at the handle, only rotation 2 is transmitted to and exhibited by intermediate body B, which does not see any effect of rotation 1.

Thus, for any arbitrary combination of rotation 1 and rotation 2 at the handle, the proposed constraint map ensures that only rotation 2 is transmitted to and exhibited at intermediate body B, and only rotation 1 is transmitted to and exhibited at intermediate body A. Thus, the constraint map of FIG. 26 serves as a basic concept for a means to mechanically separate a two DoF rotational motion at the handle to two individual single DoF rotations at intermediate body A and intermediate body B, respectively. This is particularly important from a transmission stand-point. It is difficult (or mechanically more complex) to transmit a 2 DoF rotational motion from one location on a tool/machine/device to another location. But once the two DoF rotational motion has been separated into two individual single DoF rotational motions, where each one of the latter is about a respective well-defined rotation axis, transmitting these two individual rotations is relatively easy via cables, pulleys, gears, linkages, etc. Alternatively, these rotations could be electronically captured via encoders, or potentiometers, or other rotary sensors.

Another way of viewing the arrangement outlined by the constraint map of FIG. 26 is to note that the two rotations (rotation 1 at intermediate body A, and rotation 2 at intermediate body B) are completely decoupled. Rotation 1 at intermediate body A does not affect and is not affected by rotation 2 at intermediate body B.

In some variations, the parallel kinematic configuration is used as an output mechanism. In this variation, intermediate body A is allowed rotation 1 with respect to the frame due to connector 1. If rotation 1 is applied to intermediate body A via some means (e.g. a motor, or a manual crank, etc.) then intermediate body A will exhibit this rotation about rotational axis 1 with respect to the frame. Furthermore, rotation 1 will be transmitted from intermediate body A to the handle via connector 3, without affecting or being affected by any rotation 2 at the handle. This is due to the fact that connector 3 transmits rotation 1 but does not transmit rotation 2. This means that connector 3, which is compliant about rotation 2, accommodates any relative rotation 2 between handle and intermediate body A. Thus, any rotation 1 at intermediate body A is transmitted to handle.

Intermediate body B is allowed rotation 2 with respect to the frame due to connector 2. If rotation 2 is applied to intermediate body B via some means (e.g. a motor, or a manual crank, etc.) then intermediate body B will exhibit this rotation about rotational axis 2 with respect to the frame. Furthermore, rotation 2 will be transmitted from intermediate body B to the handle via connector 4, without affecting or being affected by any rotation 1 at the handle. This is due to the fact that connector 4 transmits rotation 2 but does not transmit rotation 1. This means that connector 4, which is compliant about rotation 1, accommodates any relative rotation 1 between handle and intermediate body B. Thus, any rotation 2 at intermediate body B is transmitted to handle.

Thus, any rotation 1 at intermediate body A and any rotation 2 at intermediate body B are both transmitted to the handle without conflicting with or countering each other. The handle then exhibits both of these rotations. Thus, any parallel kinematic mechanism built using the above constraint map serves as means for mechanically combining two individual single DoF rotations into a two DoF rotation. This arrangement is particularly useful because the each of two individual single DoF rotation is easy to provide via a rotary motor, or via a manual crank, or a pulley/cable, or via various other means, while directly generating a two DoF rotation motion is difficult.

Another way of viewing this structure/arrangement is to note that the two rotations (rotation 1 at intermediate body A, and rotation 2 at intermediate body B) are completely decoupled. Rotation 1 at intermediate body A does not affect and is not affected by rotation 2 at intermediate body B.

Figure 27:
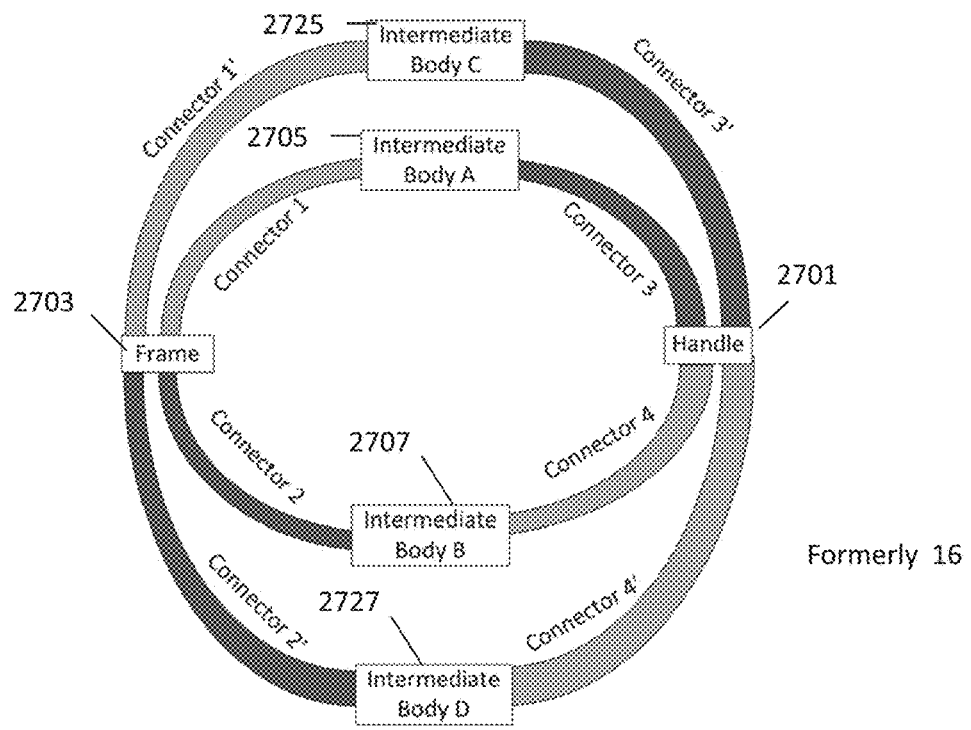
FIG. 27 shows a variation of the constrain map of FIG. 26, in which additional parallel paths have been added while maintaining the same functionality.

FIG. 27 is an example of an enhanced constraint map similar to the constraint map shown in FIG. 26. The constraint map shown in FIG. 26 is a minimalist representation of the proposed constraint map. Additional rigid bodies and connectors may be added to this constraint map to achieve the same functionality or enhanced functionality, while keeping the basic ideas of mechanical decoupling/separation/combination intact. One such example is shown in FIG. 27. In addition to intermediate bodies A 2705 and B 2707, there can be intermediate body C 2725 and intermediate body D 2727. Intermediate body C is connected to frame 2703 via connector 1', which allows rotation 1 but restricts/constrains (and therefore transmits) rotation 2. Intermediate body C is connected to handle 2701 via connector 3' which allows rotation 2 but restricts/constrains/transmits rotation 1. Intermediate body D is connected to frame via connector 2' which allows rotation 2 but restricts/constrains/transmits rotation 1. Intermediate body D 2727 is connected to handle 2701 via connector 4' which allows rotation 1 but restricts/constrains/transmits rotation 2. It is important to note that the constraint map of FIG. 27 is an augmentation of FIG. 26. It has all the elements seen in the constraint map of FIG. 26 plus more elements that do not compromise the original structure of functionality of the FIG. 26 constraint map. The additional elements shown in FIG. 27 may further improve functionality in terms of physical strength and robustness without conflicting with structure, intent, logic, and functionality of the original constraint map.

The connectors shown in FIGS. 26 and 27 could have additional attributes beyond those listed above. For example, connector 1 allows rotation 1 and constrains/restricts/transmits rotation 2. This accounts for only two out of six possible DoF or motions. One could also add that: for the constraint map of FIG. 26, connectors 1 and 3 and/or connectors 2 and 4 are stiff in rotation 3 (which could be referred to as roll rotation if rotations 1 and 2 are pitch and yaw). In other words, any given connector constrains/restricts/transmits rotation 3 in addition to its functionality with respect to rotation 1 and rotation 2. This would enable that rotation 1 and rotation 2 are allowed between handle and frame, while rotation 3 is restricted and therefore transmitted between handle and frame. As described in detail below, rotations 1, 2, and 3 may be defined with reference to the frame. For example, rotations 1, 2 and 3 (e.g., pitch, yaw, and roll rotation, respectively) may be understood to be rotations relative to the frame.

The constraint map may also be modified to include a requirement that connectors 1 and/or 3 and connectors 2 and/or 4, allow translation along rotational axis 3. This would result in allowing translational motion along direction 3 to be allowed between the handle and frame.

Described herein are apparatuses that embody the constraint map of FIG. 26, including the variations shown in FIGS. 9-11 and 12-13.

As required, detailed embodiments of the present invention are disclosed herein; however, it is to be understood that the disclosed embodiments are merely exemplary of the invention that may be embodied in various and alternative forms. The figures are not necessarily to scale, and some features may be exaggerated or minimized to show details of particular components. Therefore, specific structural and functional details disclosed herein are not to be interpreted as limiting, but merely as a representative basis for teaching one skilled in the art to variously employ the present invention.

The present invention provides a high-dexterity, multi-DoF, minimal access tool capable of intuitive actuation for use in MIS, endoscopy, or other interventions. With reference to the drawings, a tool in accordance with the present invention is designated generally by reference numeral 10 and may provide the following functionality. First, six DoF may be provided at an end effector 12, such as a tool tip manipulator, to provide complete motion control in the three translational directions and three rotational directions. Additionally, the end effector 12 may have an open/close capability for grasping, cutting, etc., depending on its use. Ergonomic and intuitive motion mapping may be provided from an input (i.e., a user's arm, hand, and fingers) to an output (i.e., the end effector 12), and the tool 10 may provide force feedback to allow the user to feel the amount of force exerted by the tool 10. Still further, the tool 10 may provide motion scaling between the input and output motions, and hand-tremor reduction to improve the precision in surgery. It should be noted that "DoF" and "motion" are used interchangeably in the description provided herein. The tool 10 according to the present invention may be purely mechanical with a minimal number of components and assembly steps, ensuring simplicity and cost-effective manufacturing.

Figure 1:
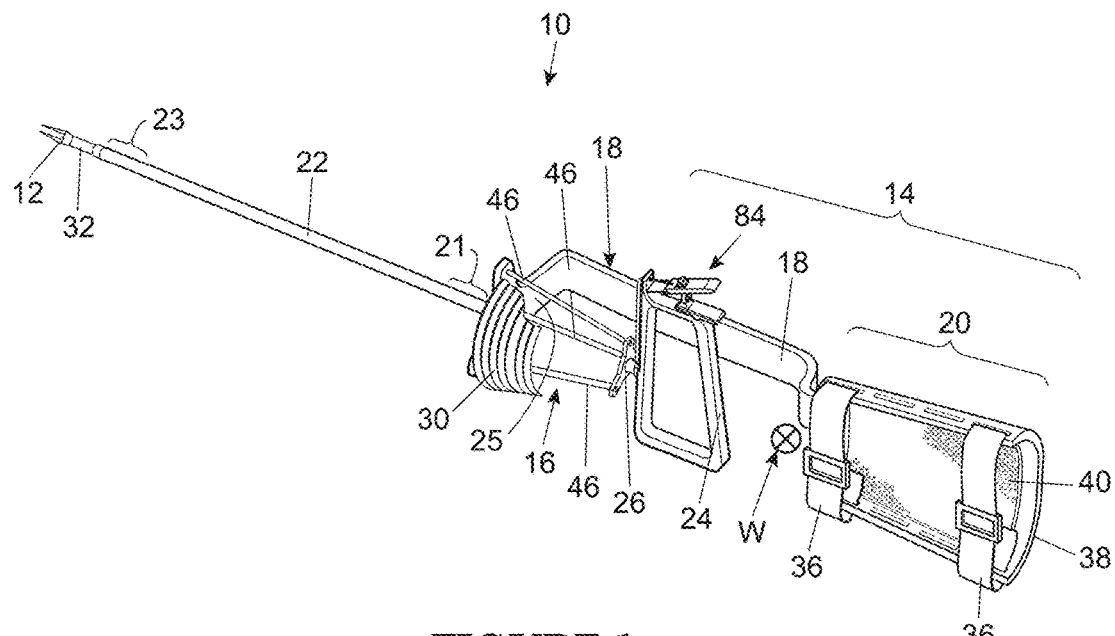
FIG. 1 is a perspective view of a minimal access tool according to the present invention.

With reference to FIG. 1, a mechanical hand-held tool 10 is illustrated, wherein the DoF of the end effector 12 may be controlled by their physiological analogs at the user's end 14. Intuitive input-output motion mapping for the tool 10 may be achieved when the DoF motions of the end effector 12 match those of the user's arm, hand, and fingers. The tool 10 includes a frame 18 arranged to be attached to the user's arm, typically the forearm, such as via an arm attachment member 20 or other means. The frame 18 may be generally rigid, and also may incorporate length and size adjustability features so as to accommodate users of varying sizes. The tool 10 further includes a tool shaft 22 having a proximal end 21 and a distal end 23, wherein the frame 18 may be connected to the shaft proximal end 21. The tool shaft 22 is configured to pass through a surgical port (e.g. trocar or cannula) in the patient's body (not shown), such that the tool shaft 22 may be generally elongated and thin with a generally round cross-section, although the shaft 22 is not limited to this configuration. The tool shaft 22 may be generally rigid, or alternatively a flexible tool conduit such as one used in endoscopy may be used while retaining all other functionality.

In this example, an input joint is connected to the frame 18 and arranged to receive the user's wrist motion input at a handle, wherein the input joint includes a virtual centerof-rotation (VC) mechanism 16 (best shown in FIGS. 9, 12, and 13) which provides a center of rotation that generally coincides with a wrist joint W of the user. In other words, the VC mechanism 16 creates a 2-DoF or 3-DoF joint between the frame and the handle with a virtual center-of-rotation located close to the user's own wrist W when the user's hand holds/interfaces the handle. A joint or mechanism with a virtual center-of-rotation is one where no physical structure need exist at the virtual center-of-rotation. Such a joint should include a body that the user's hand can actuate, wherein this body is constrained by the VC mechanism 16 to move as if virtually pivoted at a point at the user's wrist by a 2-DoF universal or 3-DoF rotational joint. With this arrangement, the user's hand can rotate freely in at least two directions relative to the user's forearm naturally about the user's wrist W. The natural motion of the user's arm is then replicated at the end effector 12 inside the patient's body, via transmission systems described subsequently.

A traditional 2-DoF joint could be used for the input joint, as in U.S. Pat. No. 7,147,650, incorporated by reference herein. However, the center-of-rotation of the input joint in such cases coincides with the physical location of the joint, and hence can never be made to coincide with the user's wrist given the physical geometry/space constraints. Consequently, at the tool input, the user would have to move his/her forearm, elbow, and shoulder along with his/her wrist to produce the output pitch and yaw motions at the end effector 12, which is cumbersome and non-intuitive. It is highly desirable for the user to be able to generate the pitch and yaw input motions by simply rotating his/her wrist relative to his/her forearm, which provides for the most natural, intuitive, and ergonomic actuation. For this to happen, the center-of-rotation of the input joint 16 should generally coincide with the location of the user's wrist. This enables the user to move his/her wrist naturally and comfortably during operation, independent of forearm, elbow, and shoulder motions.

Figure 3:
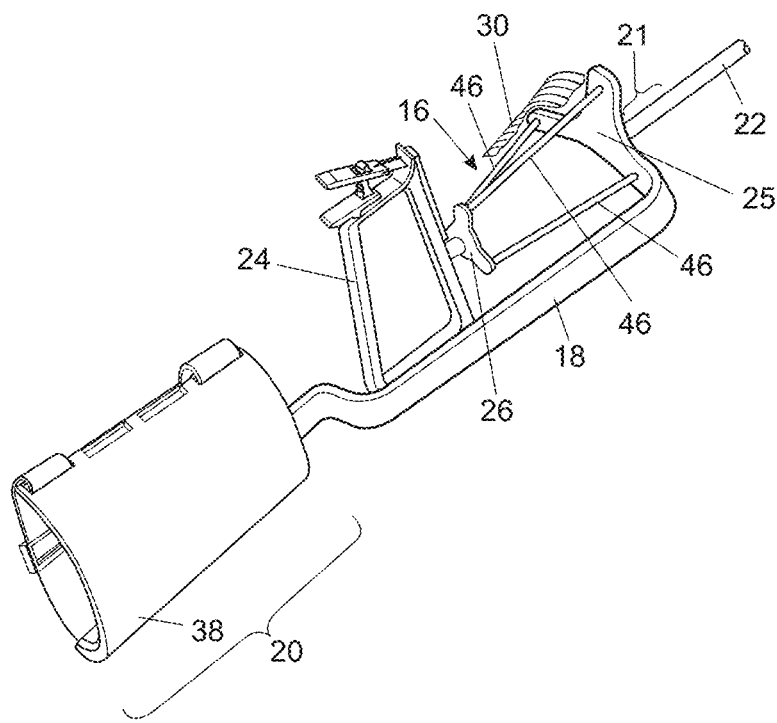
FIG. 3 is a perspective view of a user end of a minimal access tool according to the present invention.

With reference to FIGS. 1 and 3, the frame 18 gives structural integrity to the entire tool 10, providing a rigid connection between the arm attachment member 20 and the tool shaft 22, and also providing the reference ground for the VC mechanism 16. The frame 18 may be implemented in one of several ways. According to one non-limiting aspect of the present invention, a curved structure that does not interfere with the user's hand/fingers during wrist rotations may be provided, which may include a T-shaped or tubular or rectangular cross-section to enhance structural rigidity. The VC mechanism 16 may include a first end or ground base which is connected to or part of the frame.

With further reference to FIG. 1, a second, input end of the VC mechanism 16 may comprise a floating member, such as a plate 26. The tool 10 may further comprise a handle 24 (also shown in FIGS. 3 and 4) mounted to the plate 26 to allow convenient grasping by a user's hand, wherein any wrist rotations of the user's hand are transmitted to the plate 26 via the handle 24. The handle 24 may include a soft covering comprised of a material such as rubber, and different types of grip tape, foam, or other materials may be used for comfort. The handle 24 may be of a pistol-grip type as depicted, or other handle shapes may be used including, but not limited to, scissor-like rings, a squeeze-ball grip design, or an ergonomic shape that conforms to a user's hand grip. Any shape of handle 24 may be used, provided it can be mounted to the floating plate 26. Alternatively, the handle 24 and the plate 26 may be embodied as a single component by simply extending the shape of the floating plate 26. It is also understood that the floating member 26 may take forms other than the plate depicted herein. The VC mechanism 16 may be covered with a baffle 30, such as for aesthetic reasons, and to contain an additional roll rotational DoF that may be provided by a 3-DoF VC mechanism 16 as described further below.

The end effector 12 may be connected to the tool shaft distal end 23 via an output joint 32, wherein the output joint 32 is mechanically coupled to the VC mechanism input joint 16 to correlate rotational motions of the VC mechanism 16 to the rotational motions of the output joint 32. As such, the tool shaft 22 provides the reference ground for the end effector 12. A transmission system comprising cables 34 (best shown in FIGS. 5-10) connects the VC mechanism input joint 16 to the output joint 32, thereby linking their motions. However, it is understood that the present invention is not limited to the use of cables 34, and that any type of mechanical transmission between the input joint 16 and the output joint 32 is fully contemplated, as described further below. This arrangement provides that rotations of the handle, as generated by a user's wrist, are transmitted to corresponding rotations of the end effector. Furthermore, the dimensions and geometry of all components of the tool 10 according to the present invention may be chosen such that the wrist motion of the user's hand is replicated at the end effector 12 with any desired and adjustable scaling factor.

Figures 2A, 2B:
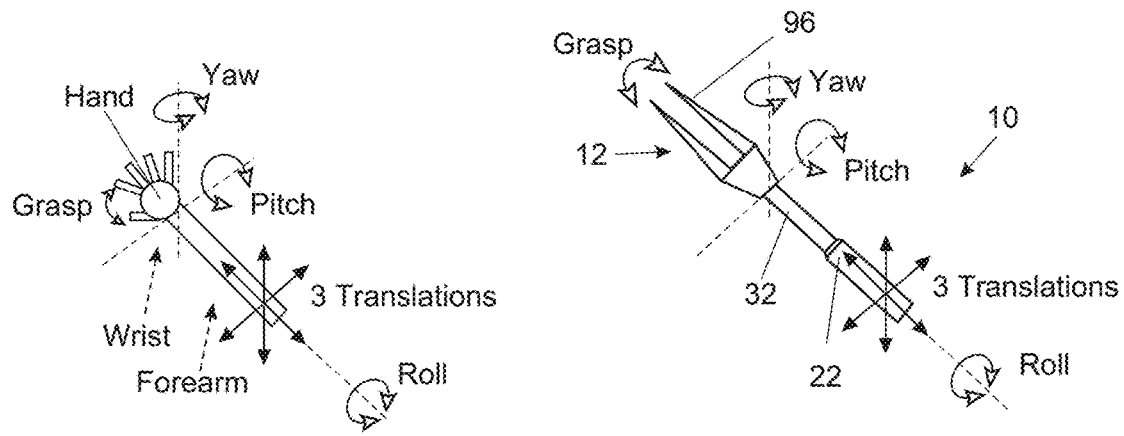
FIGS. 2A and 2B are illustrations depicting the motion input at the user's end and motion output at the tool tip, respectively, of a minimal access tool according to the present invention.

FIG. 2A shows the three translational motions and roll rotation of the human forearm, the two rotational motions (pitch and yaw) of the human wrist, and the grasping motion of human hand. FIG. 2B shows the corresponding DoF of the tool 10 according to the present invention. These DoF include three translations and a roll rotation of the tool shaft 22, two wrist-like rotations (pitch and yaw), and a grasping motion of the end effector 12. A tool 10 as described herein that provides a one-to-one mapping between the human input DoF and the output DoF of the end effector 12. The fact that the mapping of each DoF of the user input to the corresponding DoF of the end effector 12 is largely decoupled from the mapping of all the remaining DoF greatly facilitates the intuitive control (i.e., motion mapping from user input to tool output) of the end effector 12 by a user equipped with the tool 10.

In attaching the user's forearm to the tool shaft 22 via the frame 18 and the arm attachment member 20, and using the VC mechanism 16 in communication with the output joint 32, the 6 DoF of the arm and wrist, and the grasping action of the hand, may be relayed successfully to the end effector 12. Because control of the motion of the end effector 12 happens with natural motion of the user's forearm, wrist, and hand, the tool 10 according to the present invention successfully provides multi-DoF motion with intuitive input-output motion mapping. Because the system may be purely mechanical, it intrinsically relays force feedback and is robust and low-cost.

In one embodiment, the roll rotation at the end effector 12 is the consequence of forearm roll rotation only, as there is no roll rotation at the user's wrist with respect to the user's forearm. Since the frame 18 is secured to the user's forearm, any roll rotation of the forearm is transmitted entirely to the frame 18, the tool shaft 22, and ultimately to the end effector 12 when the output joint 32 is a 2-DoF joint. Thus, it is acceptable to have an input joint 16 that provides three rotational DoF (the desired yaw and pitch, and an additional roll). The roll is redundant because, in the above-described arrangement, any roll DoF of the input joint 16 cannot be actuated by the user's wrist motion. For this actuation to happen, the wrist would have to roll with respect to the frame 18, but this cannot happen given the physiological construction of the human wrist. However, as explained here, if the input joint 16 is such that it provides an extra roll DoF, this DoF simply goes unused and has no detrimental effect of the desired functionality and dexterity of the overall tool 10.

In another embodiment, a spatial transmission mechanism/system may be used not only to transmit two rotational DoF (pitch and yaw) but all three rotational DoF (pitch, yaw, and roll). In such an embodiment, it would become possible to use input 16 and output 32 joints, each with three rotational DoF. In that case, the roll DoF of the input 16 and output 32 joints would be used. The roll DoF provided by the input joint may be actuated by the twirling of the user's fingers. Note that the user's fingers are capable of generating such roll rotation in addition to the pitch and yaw rotations provided by the user's wrist. In this scenario, the transmission system can mechanically or electromechanically transmit the roll rotation generated at the input joint to the output joint.

The present invention may provide a method to translate the user's forearm's four DoF (3 translations and one roll rotation) to the corresponding DoF of the end effector 12 by providing a reference ground for the end effector 12. With reference to the description above of FIGS. 1-4, the tool 10 described herein may be provided with a continuous rigid structure attached directly or indirectly to the user's arm. This continuous rigid structure may also incorporate a relatively long narrow feature (analogous to the tool shaft) to penetrate the patient's body. The tip of the long narrow feature, which now is part of the continuous rigid structure, may provide a reference ground for the end effector 12. This ground and end effector 12 may be interconnected via an output joint 32. This continuous rigid structure also provides a reference ground for the VC mechanism 16 described above. The plate 26, which sees the user's motion inputs, may be connected to this ground via the VC mechanism input joint 16. Thus, the continuous rigid structure may effectively create a shared reference ground for the various mechanisms, sub-mechanisms, and input as well as output joints in the tool 10 according to the present invention. This continuous rigid structure can include a single rigid body or several bodies connected rigidly to each other. These several rigid bodies may be detachable, re-attachable, and re-configurable.

According to one aspect of the present invention, the continuous rigid structure may comprise the arm attachment member 20, the frame 18, and the tool shaft 22 (see FIG. 1). The arm attachment member 20 may be used to attach the continuous rigid structure to the forearm of the user. The coupling with the user's forearm may be rigid or non-rigid. The coupling may itself allow certain DoF and constrain others between the forearm and attachment member. The end effector 12 may be attached to the continuous rigid structure at the tool shaft distal end 23 via an output joint 32. During a surgical procedure, the end effector 12, the output joint 32, and a portion of the tool shaft 22 are generally in vivo, while the other components are generally in vitro. The implementation of the frame 18, the tool shaft 22, and the arm attachment member 20 dictates the general shape of the continuous rigid structure. Obviously, the geometries of these components and the overall continuous rigid structure can vary from that depicted herein and can be selected for right-hand or left-hand use.

In one embodiment, the end effector 12 may be made detachable so that the user may release and detach one end effector 12 and replace it with a different kind of end effector 12. The end effector 12 may be replaced while keeping the frame 18 attached to the user's forearm and the tool shaft 22 remaining attached to the frame 18. This allows the end effector 12 to be pulled out of the tool shaft 22 at a location outside the patient's body and be replaced by an end effector 12 with a different functionality during an operation, thus allowing the tool shaft 22 to remain in place while the end effector 12 is replaced. The end effector 12 and associated mechanisms may be disengaged utilizing a quick release or other mechanism and withdrawn through a hole in the frame 18 or tool shaft 22 without moving the tool shaft 22. This allows the user to change end effectors 12 while keeping the tool 10 inside of the patient.

Figure 4:
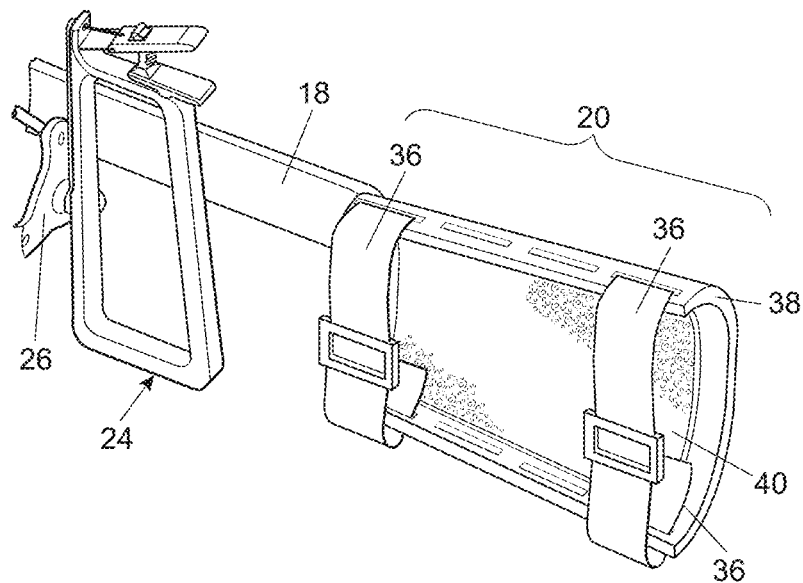
FIG. 4 is a perspective view of a user end of a minimal access tool according to the present invention including a forearm attachment device.

Turning to FIGS. 1 and 3-4, the arm attachment member 20 is provided to quickly and easily secure the user's forearm to the frame 18. The arm attachment member 20 may include flexible or rigid members to provide a secure interface or coupling between the forearm and the frame 18. The coupling may allow certain DoF and constrain others between the forearm and attachment member 20. According to one aspect of the present invention, the arm attachment member 20 may include flexible adjustable straps 36 that encircle the forearm and use a hook-and-loop arrangement, snap joints, buckles or other features for securing the arm attachment member 20 to the user's forearm. The arm attachment member 20 may also include a supporting shell-type structure 38 which may be made generally in the shape of a forearm (for example, half cone-shaped) to ensure comfort and correct attachment positioning. Furthermore, the shell structure 38 may be at least partially lined with a foam pad 40 or other suitable material to provide a comfortable interface between the user's forearm and the arm attachment member 20. The foam pad 40 may comprise a polyurethane open cell foam, although other types of soft gel and/or foam may also be used. In one embodiment, the arm attachment member 20 may extend around approximately half of the forearm circumference. According to one non-limiting aspect of the present invention, the arm attachment member 20 may be integrated with the frame 18 for ease of manufacturing.

It is understood that variations of the arm attachment member 20 are also contemplated within the scope of the present invention. For example, the support shell structure 38 may extend partially or completely around the forearm. If the shell structure 38 extends partially around the forearm, other flexible or rigid components may be used to completely enclose and secure the forearm. The shell structure 38 can also extend around the entire circumference of the arm either continuously or in multiple sections. If the shell structure 38 encircles the forearm continuously, shape-morphing padding may be used to fit the forearm in place snugly. This padding could possibly be either passive or actuated by pressure, heat, or some other controllable shape-morphing structure. If the shell structure 38 encircles the forearm in sections, joints may be provided between each section.

Figure 5A:
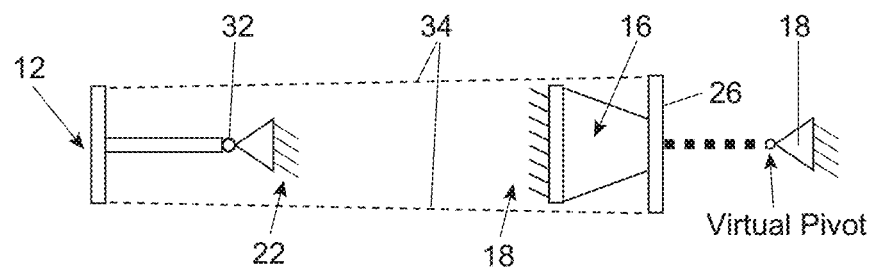
FIGS. 5A-5C are schematic illustrations of a cable transmission mechanism of a minimal access tool according to the present invention.
Figure 5B:
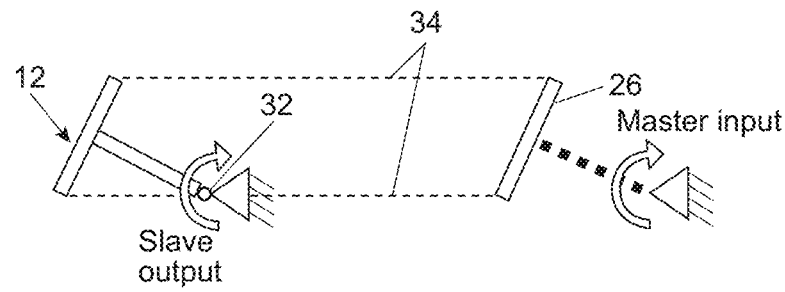
Figure 5C:
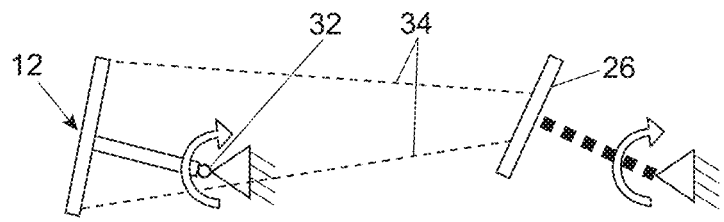

Turning now to FIGS. 5A-5C, the present invention provides a method to relate the two wrist DoF to the corresponding two rotational DoF of the end effector 12. This may be achieved using a master-slave, cable-based spatial transmission design, where the user actuates the master joint (input joint or VC mechanism 16) and the motion is transferred to the slave joint (output joint 32) via cables 34, and optionally cams (see, for example, FIG. 7) or pulleys (see, for example, FIG. 8). In this design, the two joints are coupled such that the motion at the output joint 32 is dependent on the input joint 16. The user input for actuating the input joint 16 comes from the rotation of the user's hand which happens about the user's wrist relative to the user's forearm. The two joints in question should have at least two rotational DoF (pitch and yaw) each. Furthermore, since the frame 18 is secured to the user's forearm, as described earlier, this structure and its extension such as the tool shaft also provide the ground for the two joints. Consequently, the two rotations produced at the end effector 12 are with respect to the user's forearm. A planar illustration of the transmission design, depicting one rotational DoF, is provided in FIG. 5 for the purpose of explanation. However, it should be understood that the present invention includes a spatial or three-dimensional transmission design that transmits at least two wrist rotations (pitch and yaw) while utilizing 2-DoF or 3-DoF joints as the input 16 and output 32 joints.

In one embodiment, respective points on the floating plate 26 at the input joint 16 and the end effector 12 at the output joint 32 with similar orientation are connected (i.e., top to top, bottom to bottom, etc.) via cables 34, as schematically represented in FIG. 5. This kind of connection ensures independent control of the two rotational DoF (pitch and yaw) at the end effector 12 by corresponding rotations of the user's wrist. rotation of the input joint 16 causes push and/or pull action to be transmitted from the floating plate 26 to the end effector 12 via cables 34 that may pass through the tool shaft 22 and attach to the output joint 32. In general, corresponding points on the floating plate 26 and end effector 12 can be connected with either cables 34 or instead with rigid links (or push rods) with appropriate joints/interfaces. It is also contemplated that the connection points could be reversed, e.g. top to bottom, bottom to top, to produce motion at the end effector 12 in a direction opposite the input motion at the floating plate 26 and the handle 24.

The transmission system according to the present invention allows for motion scaling, depending upon the type and location of the cable connection points. For example, FIG. 5C depicts motion scaling between the input and output joints 16, 32 which may be accomplished by varying the attachment points of the cables 34 between the end effector 12 (output joint 32) and the floating plate 26 (input joint 16). In one embodiment, compliant and dampened joints may be used in the VC mechanism 16, a compliant and dampened universal joint may be used for the output joint 32, and finite stiffness cables 34 may be used for the motion transmission system. All these flexible and dampening elements together may act as a low-pass filter, reducing the effects of high frequency input hand-tremors at the output motion of the end effector 12.

Figure 6:
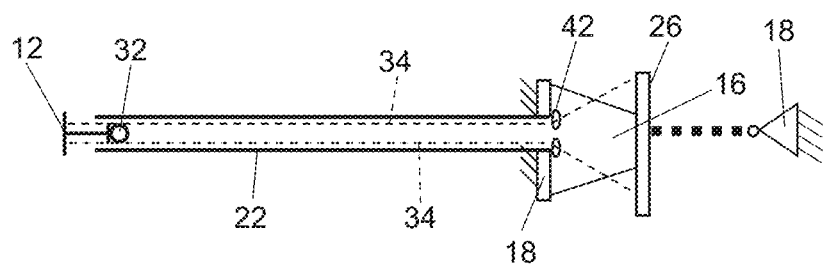
FIG. 6 is a schematic illustration of another embodiment of a cable transmission mechanism of a minimal access tool according to the present invention.
Figure 7:
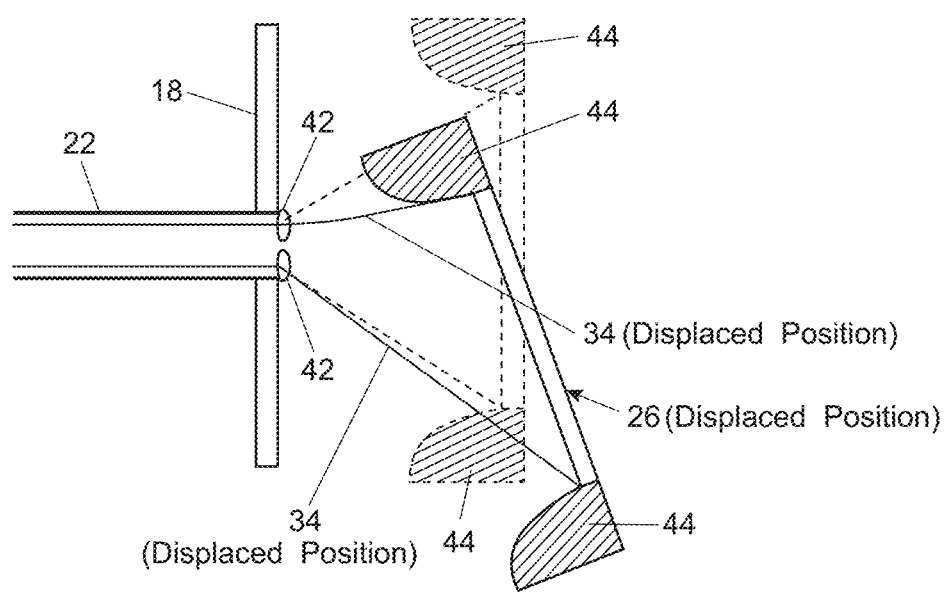
FIG. 7 is a schematic illustration of an input of a cable transmission system according to the present invention in the presence of cam surfaces.
Figure 8:
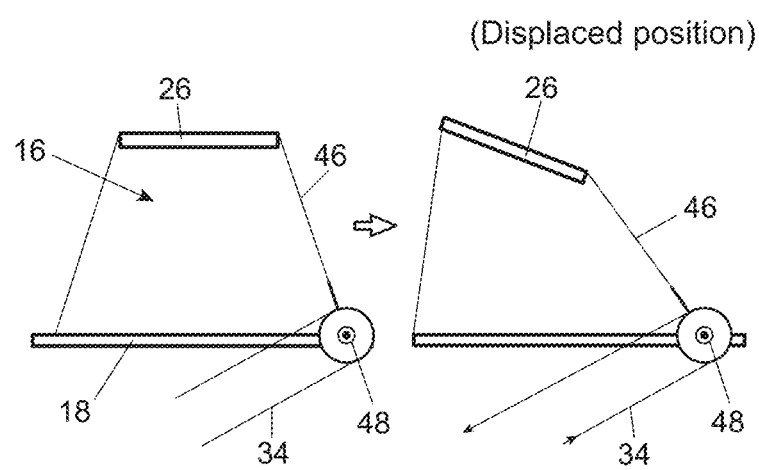
FIG. 8 is a schematic illustration of a cable transmission system according to the present invention wherein the transmission cables are attached to links of a virtual center-of-rotation (VC) mechanism.

The cables 34 may be routed through the tool shaft 22 (e.g., as illustrated in FIGS. 6 and 7) so that they remain shielded and protected from wear. According to the present invention, there may also be several routing components to prevent tangling of the cables 34 and ensure uninhibited motion. These components may be attached to or supported on the frame 18 or the tool shaft 22, and may include several individual holes 42 through which individual cables 34 pass, or small pulleys or rollers around which the individual cables 34 are routed. There may be variations on these routing components, depending on the configuration of the tool shaft 22 and the frame 18.

With the motion transmission system according to the present invention, a plurality of cables 34 may be used such as, but not limited to, four or more. Increasing the number of cables 34 may be beneficial up to a certain point, providing a higher degree of articulation at every position. The cables 34 may also be stiff or moderately compliant along their lengths. If compliant, the cables 34 may have inherent flexibility or springiness in series that provide the elasticity. This axial compliance can be carefully selected to filter/dampen any hand tremors and provide more stable and precise motion at the end effector 12. Also this axial compliance can serve to limit tension in the cables and prevent damage or failure of the transmission and routing components (such as the cables themselves, small pulleys/rollers, etc.)

At least one spring or other such mechanism may be attached to the VC mechanism 16 ground (i.e., the frame 18) on one side and the floating plate 26 on the other side. While such a spring would not constrain the previously described DoF of the input joint 16, it may keep the plate 26 in a nominal "centered" condition in the lack of any input motions from the user.

As shown in FIG. 7, as the plate 26 of the VC mechanism 16 turns to one side in response to a user input at handle 24, it pulls on the transmission cable 34 on one side and releases the transmission cable 34 on the other side. The tension in the cable 34 on one side transmits all the way to the end effector 12 and makes it turn accordingly. During this entire procedure, the geometry of the VC mechanism 16 and transmission may be such that more cable 34 is released on the second side as compared to the amount of cable 34 pulled on the first side. Since the overall length of cable 34 has to remain constant in the system, this results in cable slack on the second side. According to one embodiment, cam surfaces 44 may be incorporated in the floating plate 26 geometry, another portion of the input joint 16, or the frame 18 in order to alleviate this issue. It is understood that cam surfaces 44 may be utilized in any of the various tool embodiments disclosed herein. The cam surfaces 44 may be configured such that any extra cable 34 on any side of the input portion of the transmission gets wrapped over the cam surface 44, thus effectively eliminating any cable slackness. Another embodiment, illustrated in FIG. 8, involves attaching the transmission cables 34 to one or more components/links of the VC mechanism 16 as opposed to the floating plate 26 of the VC mechanism 16. Pulleys 48 may also be utilized, wherein each pulley 48 rotates about a point on the frame 18 and alleviates the challenges associated with cable slack discussed above.

As described above, the VC mechanism 16 may include a floating plate 26 that the user's hand can actuate, such as via a handle 24, with respect to the frame 18. The VC mechanism 16 ensures that this plate 26, and therefore the handle 24, is restricted to move as if virtually pivoted around a point at the user's wrist via a 2 DoF or 3DoF joint. The VC mechanism 16 should provide a virtual center located at the user's wrist as best as possible. Second, the virtual center created by the VC mechanism 16 should remain located close to the user's wrist throughout the mechanism's entire range of motion. However, the VC mechanism 16 may cause a drift in the location of the virtual center, typically with large rotational displacements by the user. In certain embodiments of the VC mechanism 16, the location of the virtual center can drift along the axis of the tool 10, which is a consequence of the mechanism type and geometry. Dimensions and geometry can be chosen to minimize the magnitude of this drift, but a small amount may remain. In that case, it is desirable that the VC mechanism 16 provide some means for accommodating the deviation of the virtual center from the user's actual wrist rotation point (such as the springs described above). If this is not provided, the range by which the user can move the plate 26, via the handle 24, smoothly and effortlessly in the yaw and pitch rotational directions may become restricted.

Figure 9:
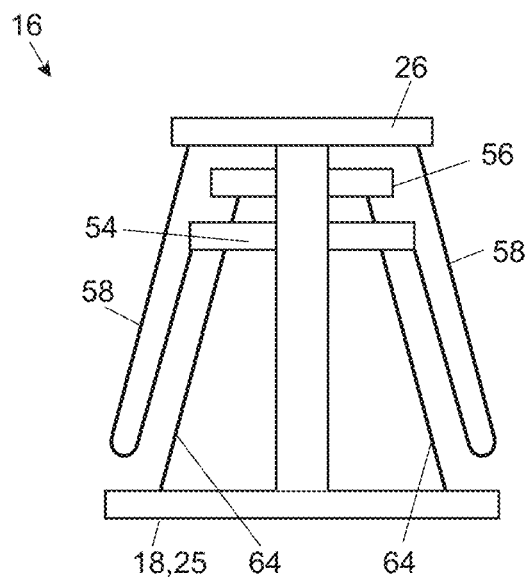
FIGS. 9, 10, and 11 are front elevational, side elevational, and perspective views, respectively, depicting a cascaded-link VC mechanism according to the present invention.
Figure 10:
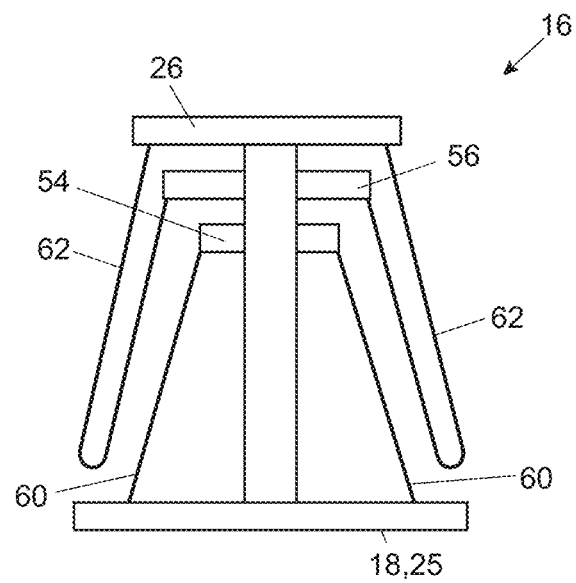
Figure 11:
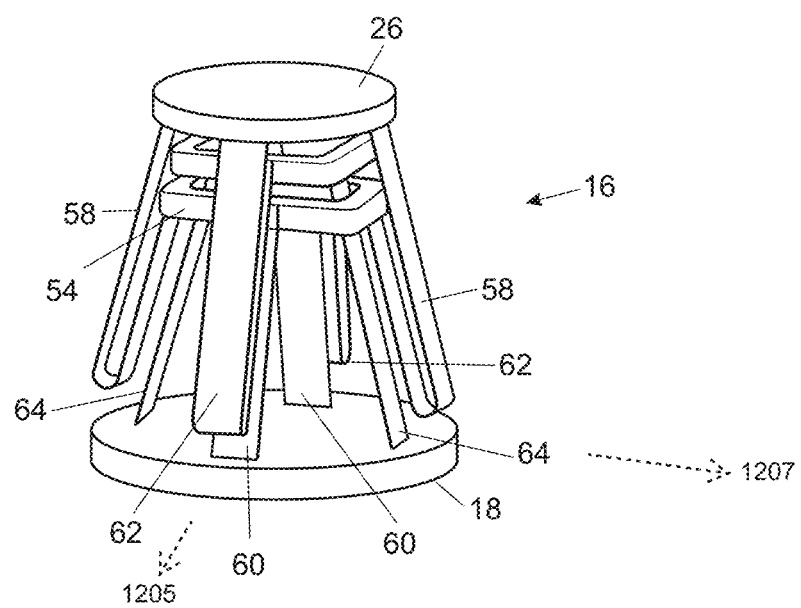

The VC mechanism 16 should allow for a practical transmission method to transmit the floating plate 26 pitch and yaw motions, actuated by the user's hand via the handle 24, to the end effector 12. In another embodiment, a cascaded VC mechanism 16 may be provided which resolves the user input (which can be a general combination of pitch and yaw) and into two clearly separated single rotations. In other words, as depicted in FIGS. 9-11, when the floating plate 26 is rotated by yaw and pitch, a first intermediate member or plate 54 only experiences the yaw part of the overall input motion while rejecting the pitch component, whereas a second intermediate member or plate 56 only experiences the pitch part of the overall motion while rejecting the yaw component. Cables (not shown) mechanically coupled to the first and second intermediate members 54, 56 then transmit the separate pitch and yaw motions to the end effector 12. Cam surfaces, similar to those described above with reference to FIG. 7, may be provided on one or both of the first and second intermediate members 54, 56 in order to prevent cable slack. This configuration reduces the one 2-DoF transmission design problem, which has to transmit two rotations at the same time, into two 1-DoF transmission design problems, each of which have to transmit only one rotation independent of the other.

The floating plate 26 of the VC mechanism 16 of FIGS. 9-11 may be connected to the intermediate member 54 via a first set of connectors 58. Connectors 58 may be such that they transmit a yaw rotation from the floating plate 26 to the first intermediate member 54 because the connectors 58 are stiff in that direction. The first intermediate member 54 may be connected to the frame 18 via a second set of connectors 60. Because the connectors 58 are compliant in the pitch rotational direction and the connectors 60 are stiff with respect to pitch rotation relative to the frame 18, any pitch rotation of the floating plate 26 does not get transmitted to the first intermediate member 54.

Thus, this VC mechanism 16 of FIGS. 9-11 provides a mechanical filtering arrangement such that, given any random combination of yaw and pitch rotations of the plate 26 (actuated by the user's hand such as via the handle 24), only the yaw component of that rotation is seen by the first intermediate member 54, while the pitch component of the overall rotation is rejected or not seen by the first intermediate member 54. In the other direction, the plate 26 is attached to the second intermediate member 56 via a third set of connectors 62 which are stiff in the pitch direction and compliant in the yaw direction. The second intermediate member 56 is attached to the frame 18 via a fourth set of connectors 64 which are stiff in the yaw direction and compliant in the pitch direction. Hence, any pitch rotation of the floating plate 26 is transmitted to the second intermediate member 56 via the connectors 62. However, any yaw rotation of the plate 26 is not transmitted to the second intermediate member 56 since the connectors 62 are compliant in this direction and the connectors 64 are stiff in this direction.

In the end, therefore, this embodiment of the VC mechanism 16 is able to separate out the combined yaw and pitch rotations of the floating plate 26, produced by the yaw and pitch rotation of user's wrist as the user's hand holds the handle 24, into a pure yaw rotation of the first intermediate member 54 and a pure pitch rotation of the second intermediate member 56. Now, intermediate members 54, 56 may be used to further transmit the yaw and pitch rotations to the end effector 12 via coupling to cables (not shown). As mentioned above, two relatively independent 1-DoF transmission problems may be dealt with as opposed to a single 2-DoF transmission problem. It should be noted that the members 54, 56 and connectors 58, 60, 62, and 64 are not limited to the shapes and configurations depicted herein.

Connectors 60 and 64 may be oriented such that an extrapolation of their lengths would intersect at the user's wrist. This may provide the virtual center attribute of the VC mechanism 16. Connectors 58 and 62 may be shaped such that they do not impose any constraint along the tool axis 52. Thus, any deviation of the virtual center provided by connectors 60 and 64 from the actual wrist center of the user may be accommodated by the axial direction compliance of connectors 58 and 62.

The mechanism variation shown in FIGS. 9-11 also embodies the constraint map of FIG. 26. In addition to being a two rotational DoF (pitch and yaw) PK mechanism based on the constraint map of FIG. 26, this variation provides the virtual center (VC) functionality. In this example, frame 18 corresponds to the frame 18 of FIG. 26 and plate 26 (or equivalently handle 24) corresponds to the handle of FIG. 26. The pitch rotation (rotation about pitch axis 1205) corresponds to rotation 1 and the yaw rotation (rotation about yaw axis 1207) corresponds to rotation 2. Frame 18 is connected to Plate 56 (intermediate body A) via strips 64 (connector 1) which allows pitch rotation and constrains yaw rotation. Plate 56 (intermediate body A) is connected to the Plate 26 (handle) via strips 62 (connector 3), which allow yaw rotation and constrain pitch rotation. Furthermore, frame 18 is connected to Plate 54 (intermediate body B) via strips 60 (connector 2) which allows yaw rotation and constrains pitch rotation. Plate 54 (intermediate body B) is connected to the Plate 26 (handle) via strips 58 (connector 4), which allow pitch rotation and constrain yaw rotation.

This embodiment illustrates that any given connector (1, 2, 3, or 4) can comprise one or more physical elements. For example, connector 1 comprises the two strips labeled 64. The actual construction of the connector defines an embodiment, but its functionality is conveyed by the constraint map. Strips may also be referred to as transmission strips.

Figure 47A:
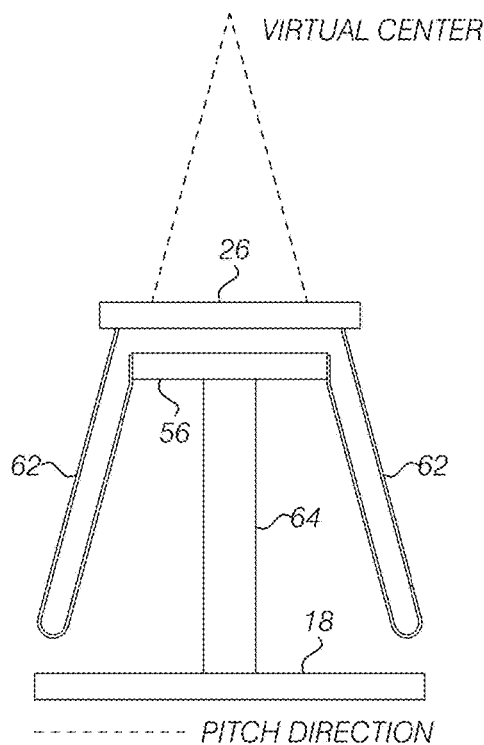
FIGS. 47A and 47B show front and side views, respectively, of a schematic illustrating one of the two independent paths for transmission of motion from a parallel kinematic mechanism similar to the variation shown in FIGS. 9-11.
Figure 47B:
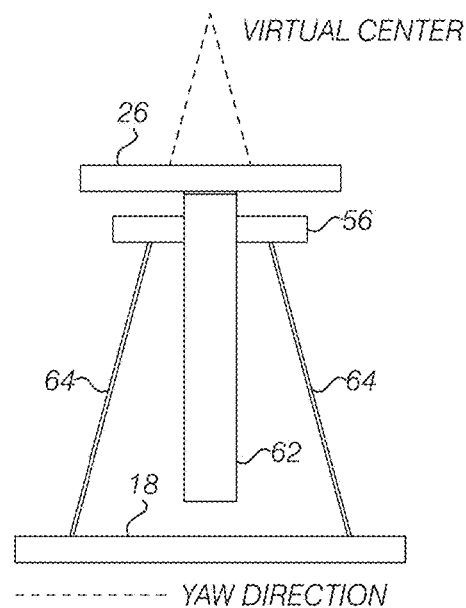
Figure 48A:
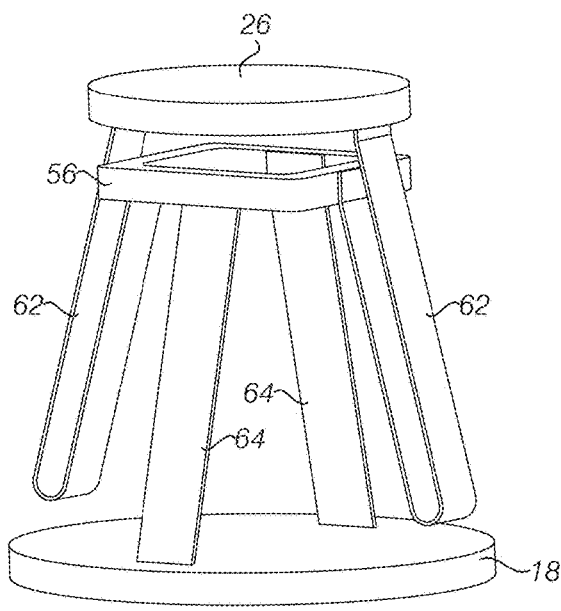
FIGS. 48A and 48B show side perspective views of the portion of the parallel kinematic mechanism shown in FIGS. 47A and 47B.
Figure 48B:
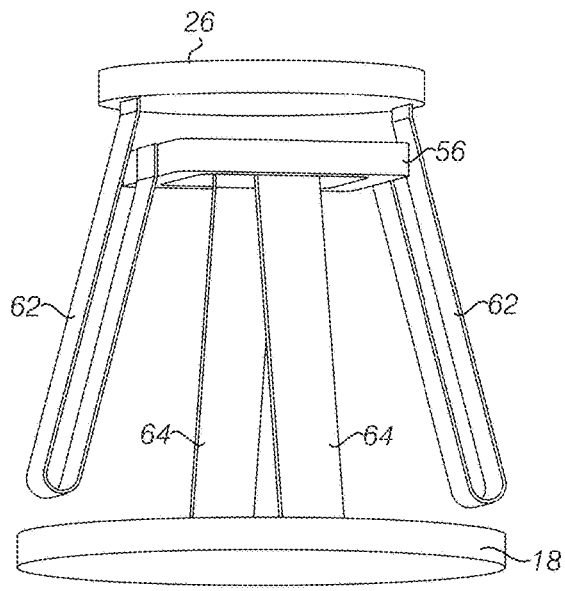
Figure 49A:
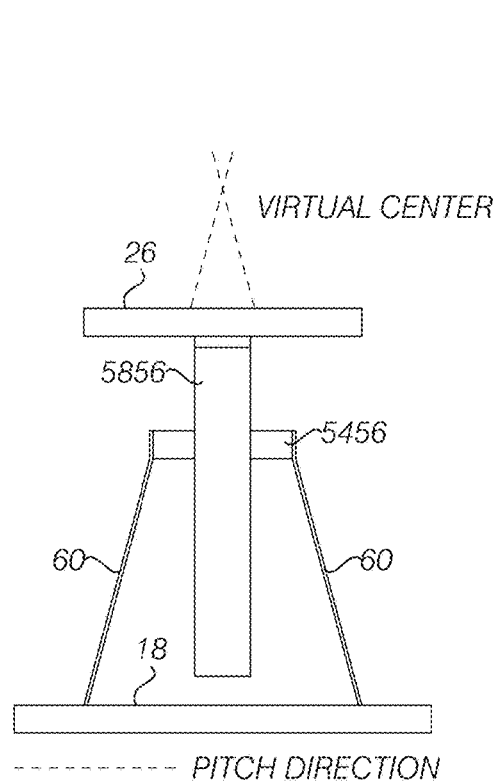
FIGS. 49A and 49B illustrate a second portion of the parallel kinematic mechanism similar to that shown in FIGS. 9-11, which may be combined with the portion shown in FIGS. 47A and 48B.
Figure 49B:
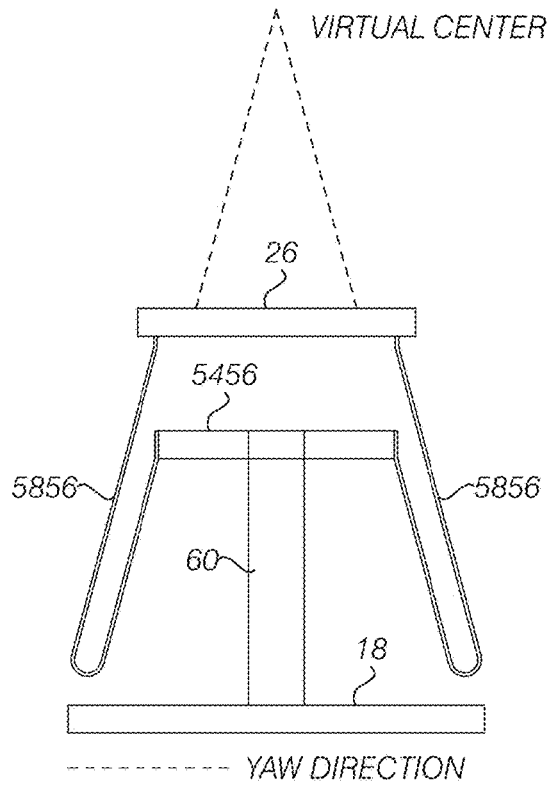
Figure 50:
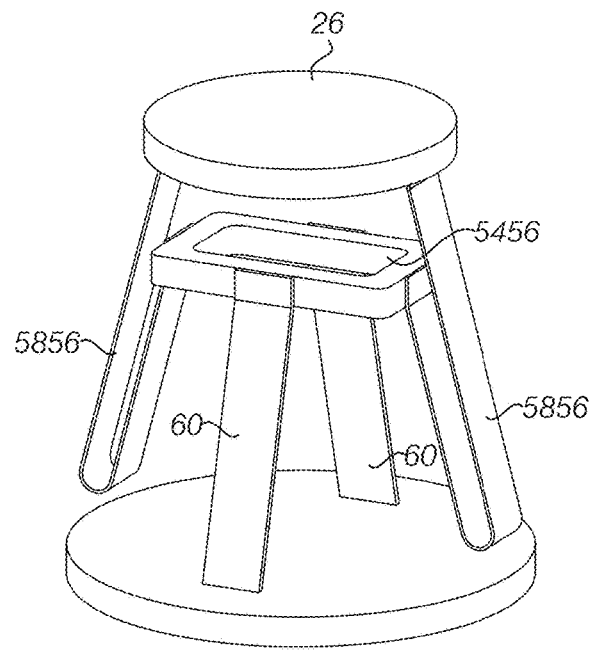
FIG. 50 sows a side perspective view of the portion of the parallel kinematic mechanism shown in FIGS. 49A and 49B.
Figure 51A:
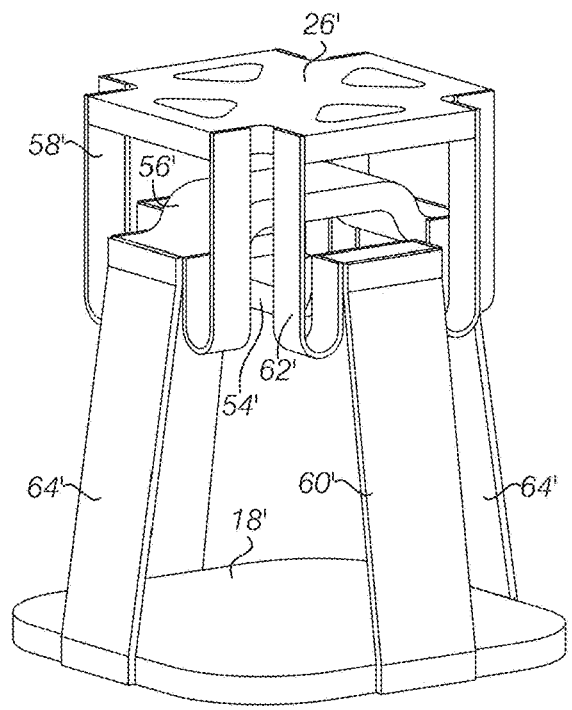
FIGS. 51A and 51B show side and bottom perspective views, respectively, of another variation of a parallel kinematic mechanism, similar to the variation shown in FIGS. 9-11.
Figure 51B:
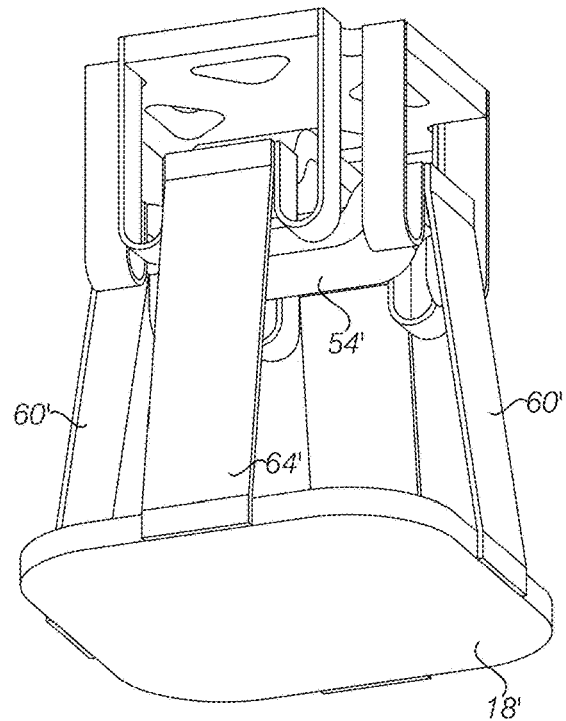

FIGS. 47A and 47B illustrate the mechanism of FIGS. 9-11 in partial configurations. It should be understood that these figures are simply meant for describing the structure and functionality of the mechanism and separately do not describe the complete mechanism, illustrating the virtual center. The elements are labeled as indicated in FIGS. 9-11 and correspond. Similarly, FIGS. 48A and 48B show views of a portion of the PK mechanism of the apparatus shown in FIGS. 47A and 47B. For example, from FIG. 11, FIG. 47A shows the portion that is represented by the path "frame-connector 1-intermediate body A-connector 3-handle" of the constraint map in FIG. 26. These figures (FIG. 47B) also show that plate 56 has a virtual center of rotation with respect the frame 18 and that handle 26 has a virtual center of rotation with respect to plate 56. By choosing the geometries of the strips, these two virtual centers can be made to overlap and/or lie close to each other. FIGS. 47A and 48B, shows various different views of a portion of the PK mechanism of FIG. 9-11, including the portion that is represented by the path "frame-connector 2-intermediate body B-connector 4-handle" of the constraint map in FIG. 26. These figures also show that plate 54 has a virtual center of rotation with respect the frame 18 and that handle 26 has a virtual center of rotation with respect to plate 54. By choosing the geometries of the strips, these two virtual centers can be made to lie close to each other, as well as to the virtual centers shown in FIGS. 47A and 47B.

Figure 52A:
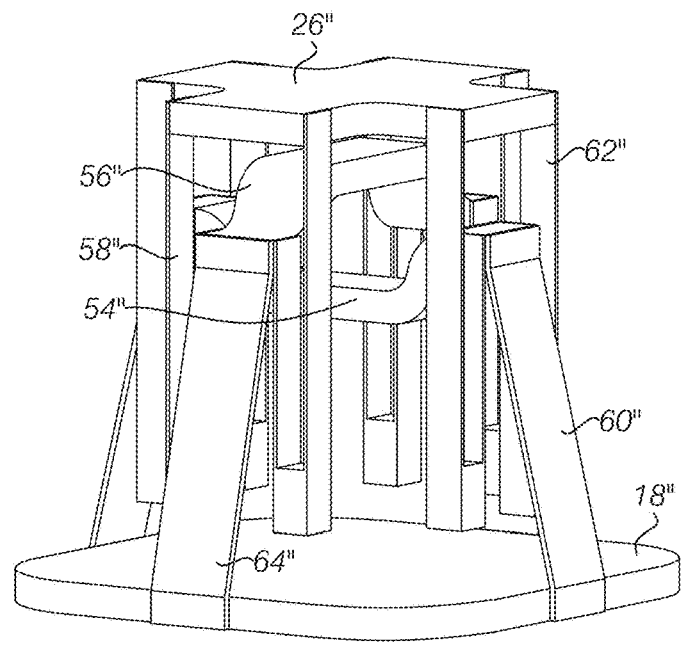
FIGS. 52A and 52B show side and bottom perspective views, respectively, of another variation of a parallel kinematic mechanism.
Figure 52B:
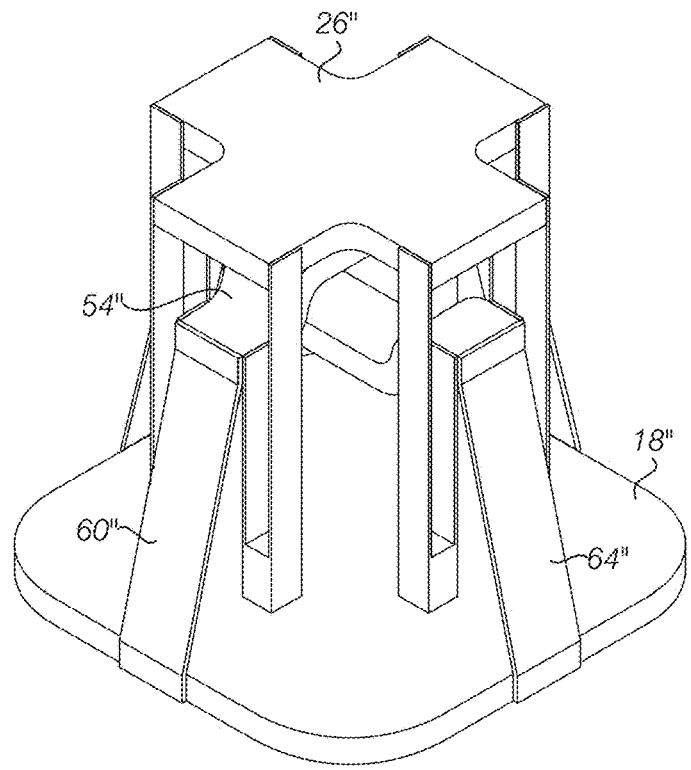

Thus, in addition to being based on the constraint map of FIG. 26, this embodiment also provides a virtual center of rotation as discussed above. This design shown in FIGS. 9-11, 47A and 47B, and 48A and 48B makes use of flexure based transmission strips, such as any of those described herein. FIGS. 51A and 51B and 52A and 52B illustrate other variations of apparatuses having parallel kinematics with two rotational DoF (pitch and yaw) based on the constraint map of FIG. 26. For example, in FIG. 51A includes a handle that may be connected to a floating plate 26'. When floating plate 26' is rotated about yaw and pitch rotational axes, a first intermediate member or plate 54' only experiences the yaw rotation part of the overall input motion while rejecting the pitch rotation component, whereas a second intermediate member or plate 56' only experiences the pitch rotation part of the overall motion while rejecting the yaw rotation component. Cables (not shown) may mechanically couple to the first and second intermediate members 54', 56' then transmit the separate pitch and yaw rotational motions to the end effector 12. The floating plate 26' of the VC mechanism may be connected to the intermediate member 54' via a first set of connectors 58'. Connectors 58' may be such that they transmit a yaw rotation from the floating plate 26' to the first intermediate member 54' because the connectors 58' are stiff in that direction. The first intermediate member 54' may be connected to the frame 18' via a second set of connectors 60'. Because the connectors 58' are compliant in the pitch direction and the connectors 60' are stiff with respect to pitch rotation relative to the frame 18', any pitch rotation of the floating plate 26' does not get transmitted to the first intermediate member 54'. FIGS. 52A and 52B show another variation similar to that in FIGS. 51A and 51B, having sets of connectors 58'', 62'' that have a slightly different geometry.

Turning now to FIGS. 12 and 13, yet another variation of VC mechanism 16 is shown. This VC mechanism 16 provides a method to transmit the pitch and yaw rotations about the respective fixed axes, actuated by the user's hand via the handle 24, to the end effector 12. This may be accomplished by resolving the user input (which can be a general combination of pitch and yaw rotations) into two clearly separated single rotations about their fixed respective axes. The VC mechanism 16 includes two fixed orthogonal pivots whose extended lines of rotation intersect, and thus create a virtual center, at the location of the user's wrist. This VC mechanism 16 ensures that the handle 24, and therefore the user's hand, is allowed to move as if virtually pivoted about a point located at the user's wrist. It should be noted that the handle 24 in this embodiment can move in towards or out away from the arm attachment location with respect to the frame, allowing the tool 10 to naturally adapt to a wide range of user hand and arm sizes, and ensuring that there is no restriction to the natural range of motion of the user's wrist.

Referring again to FIGS. 12 and 13, the handle 24 and the floating plate 26 may be connected to a first, pitch connector 66 and a second, yaw connector 68 as shown. Each connector 66, 68 may in turn be pinned about shafts 70, 72 on the respective pitch 74 and yaw 76 axes, wherein the pitch shaft 70 may receive a pitch axis pulley 78 and the yaw shaft 72 may receive a yaw axis pulley 80. The shafts 70, 72 are connected to the frame 18, which is secured to the user's arm, such that the rotations are relative to the VC mechanism 16 itself. The pitch connector 66 is stiff about the pitch axis, but is compliant about the yaw axis, allowing for the transmission of only the pitch component of the rotation while filtering the yaw component by allowing unconstrained rotation of the pitch connector 66 about the yaw axis. The opposite is true for the yaw connector 68, which will strictly transmit any yaw component of rotation while it will reject any pitch component of rotation. This design reduces the one 2-DoF transmission design problem, which has to transmit two rotations at the same time, into two 1-DoF transmission design problems, each of which have to transmit only one rotation independent of the other, such that the motion and force inputs about fixed axes may be easily transmitted to the end effector 12. Most importantly, the resulting virtual center location remains static with respect to the tool frame 18 (and therefore the user's forearm when the user's hand holds the handle) at all times, and therefore may be referred to as the "fixed axis" VC mechanism.

As such, this fixed axes VC mechanism 16 provides a mechanical filtering arrangement such that, given any general combination of yaw and pitch rotations to the handle 24 via the user's hand, only the yaw component of that rotation is seen by the yaw connector 68 while the pitch component of the overall rotation is rejected and not experienced about the yaw axis 76, and only the pitch component is seen by the pitch connector 66 while the yaw component is rejected and not experienced about the pitch axis 74. In the end, the combined yaw and pitch rotations of the handle 24 may be separated into a pure yaw rotation about the yaw axis 76 and a pure pitch rotation about the pitch axis 74. Now, the rotations about the respective pitch and yaw axes 74, 76 may be used to transmit the desired yaw and pitch rotations to the pitch and yaw axes of the end effector 12. In particular, the rotations produced at the pitch and yaw axis pulleys 78, 80 may be individually transmitted to the end effector 12 using a cable arrangement (not shown) similar to the one described above.

With this fixed axes embodiment, the orthogonal pitch and yaw axes of rotation intersect at a desirable location in space, providing the desired VC mechanism 16 behavior. This location can be made to coincide with a user's wrist when the user holds the handle and his/her forearm interfaces the frame via the forearm attachment member 20. In addition, since the axes are fixed, the location of the virtual center will remain stationary throughout the range of motion of the VC mechanism 16. The geometry of the connectors 66, 68 is such that they do not impose any constraint to translational motion along the tool axis 52 (or equivalently the roll axis), allowing for handle 24 to be adjustably held by the user depending on the user's hand size/length. Lastly, the fixed axes of rotation provide a simple transmission method that can independently transmit pitch and yaw components of a rotational input by the user to the end effector 12 while maintaining a constant transmission cable length.

In one embodiment, the present invention provides a 2 DoF (pitch and yaw) output joint 32 for motion output at the end effector 12. The output joint 32 transmits roll rotation from the tool shaft 22 to the end effector 12. Since the tool shaft 22 is part of the continuous rigid structure, and since the continuous rigid structure is securely coupled to the user's forearm, the roll rotation of the user's forearm can be transmitted to the end effector 12. Therefore, a 2-DoF rotational joint, that provides pitch and yaw rotation DoF, mounted to the in vivo portion of the tool shaft 22 may be used for this purpose. In another embodiment, the output joint 32 may be provided with a third DoF (roll rotation), along with an appropriate method for coupling this roll rotation to a corresponding roll rotation by the user at the tool's input end 14.

As mentioned above, FIG. 12 is also an example of an embodiment of a parallel kinematic mechanism based on the constraint map of FIG. 26. This mechanism 16 provides a method to resolve pitch and roll rotations at the handle 24 into a pitch only rotation at pulley 78 and roll only rotation at pulley 80. Note that pitch and yaw rotations are specific terms that may be used in place of the more generic rotation 1 and rotation 2. Comparing with the constraint map of FIG. 26, that apparatus includes a frame 18, and handle 24; in FIG. 12 the intermediate body A (referenced in FIG. 26) is pulley 78, and intermediate body B is pulley 80. The pivot joint provided by pulley pin 70 is connector 1, the pivot joint provided by pulley pin 72 is connector 2, the flexure transmission strip 66 is connector 3, and the flexure transmission strip 68 is connector 4.

In this example, connector 1 (pivot joint provided by pin 70) allows pitch rotation but constrains yaw rotation between frame (frame 18) and intermediate body A (pulley 78); connector 3 (transmission strip 66) allows yaw rotation and constrains pitch rotation between intermediate body A (pulley 78) and handle (handle 26/24); connector 2 (pivot joint provided by pin 72) allows yaw rotation but constrains pitch rotation between frame (frame 18) and intermediate body B (pulley 80); connector 4 (transmission strip 68) allows pitch rotation and constrains yaw rotation between intermediate body B (pulley 80) and handle (floating plate 26 and handle 24).

The transmission strip 66 (connector 3) has two ends 66', 66". The first end 66' is rigidly connected to pulley 78 (intermediate body A) and the other end 66" is rigidly connected to the floating plate 26 which is an extension of the handle 24 (handle). Since the pulley 78 and first end of the transmission strip are rigidly connected, they became effectively the same rigid body (intermediate body A in the constraint map of FIG. 26) and similarly since the second end of the transmission strip is rigidly connected to the handle, the two are effectively the same rigid body (handle in the constraint map of FIG. 26). Thus, one way to physically describe this would be to say that the connector 3 of FIG. 26 is that segment of the transmission strip 66 that lies between its first end and second end. Thus, the ends of a connector may be viewed/described as either part of the connector or the rigid body that the connector is attached.

Referring again to FIG. 12, the handle 24 and the floating plate 26 may be connected to a first, pitch connector 66 and a second, yaw connector 68 as shown. One end of each connector 66, 68 may in turn be pinned about a shaft 70, 72 (forming a pivot joint) on the respective pitch 74 and yaw 76 axes, wherein the pitch shaft 70 may receive a pitch axis pulley 78 and the yaw shaft 72 may receive a yaw axis pulley 80. Note that a pulley is one variation of the more generic intermediate body discussed above. In general, an intermediate body may be pulley, a gear, a pinion, a link, etc. The choice of the specific type of intermediate body may be dictated by how one plans to transmit the rotation of the intermediate body to another location. For example, if cables or belts are used as the transmission, the intermediate body may be a pulley. The intermediate body may be a gear/pinion if the transmission comprises a gear system.

The pitch connector 66 may be stiff about the pitch axis, but compliant about the yaw axis, allowing for the transmission of only the pitch component of the rotation while filtering the yaw component by allowing unconstrained rotation of the pitch connector 66 about the yaw axis. The opposite is true for the yaw connector 68, which will transmit any yaw component of rotation while it will reject any pitch component of rotation.

Thus, this mechanism 16 provides a mechanical filtering arrangement such that, given any general combination of yaw and pitch rotations at the handle 24; only the yaw component of that rotation is seen by the yaw pulley 80 while the pitch component of the overall rotation is rejected (i.e. absorbed or filtered out or not transmitted) by the flexure transmission strip 68 and is therefore not experienced by the yaw pulley 80; and only the pitch component is seen by the pitch pulley 78 while the yaw component of rotation is rejected (i.e. absorbed or filtered out or not transmitted) by the flexure transmission strip 66 and is therefore not experienced by the pitch pulley 78. In the end, the combined yaw and pitch rotations of the handle 24 may be separated into a pure yaw rotation about the yaw axis 76 at the yaw pulley 78 and a pure pitch rotation about the pitch axis 74 at pitch pulley 78.

When used as the input joint/interface of an instrument/tool/device/machine, the rotations of the pitch and yaw pulleys 78, 80 about the respective pitch and yaw axes 74, 76 may be used to transmit the desired pitch and yaw rotations mechanically to a remote end effector, or electronically to a computer input device. Compared to a serial kinematic mechanism, in the case of a parallel kinematic mechanism the two axes of rotations 74 and 76 are fixed with respect to the frame. Therefore, rotations about these axes can be transmitted via various mechanical transmission methods/systems that are practically simple and feasible. These various transmission methods/systems all operate with respect to the same ground reference frame 18. Thus, any moving components of this transmission system, all have an axis of rotation or translation or a trajectory of motion that is fixed with respect to this ground reference frame. That makes the task of designing and implementing a transmission system from each individual axis 74 or 76 to some other location on the frame (or an extension of the frame) practically feasible.

In one instance, the rotations produced at the pitch and yaw axis pulleys 78, 80 may be individually transmitted to a remote end effector using pitch and yaw transmission cables, respectively. This design greatly facilitates the capturing and transmission of 2-DoF rotational motion of a handle with respect to a frame; doing so directly from the handle is difficult; instead this design separates out the 2-DoF rotation into two 1-DoF rotations; these two rotations may be individually and independently transmitted relatively easily (using cables, or gears, or links, or electronically, or pneumatically) because they are now well-defined rotations about pitch and yaw rotation axes that are fixed with respect to the frame.

Figure 28:
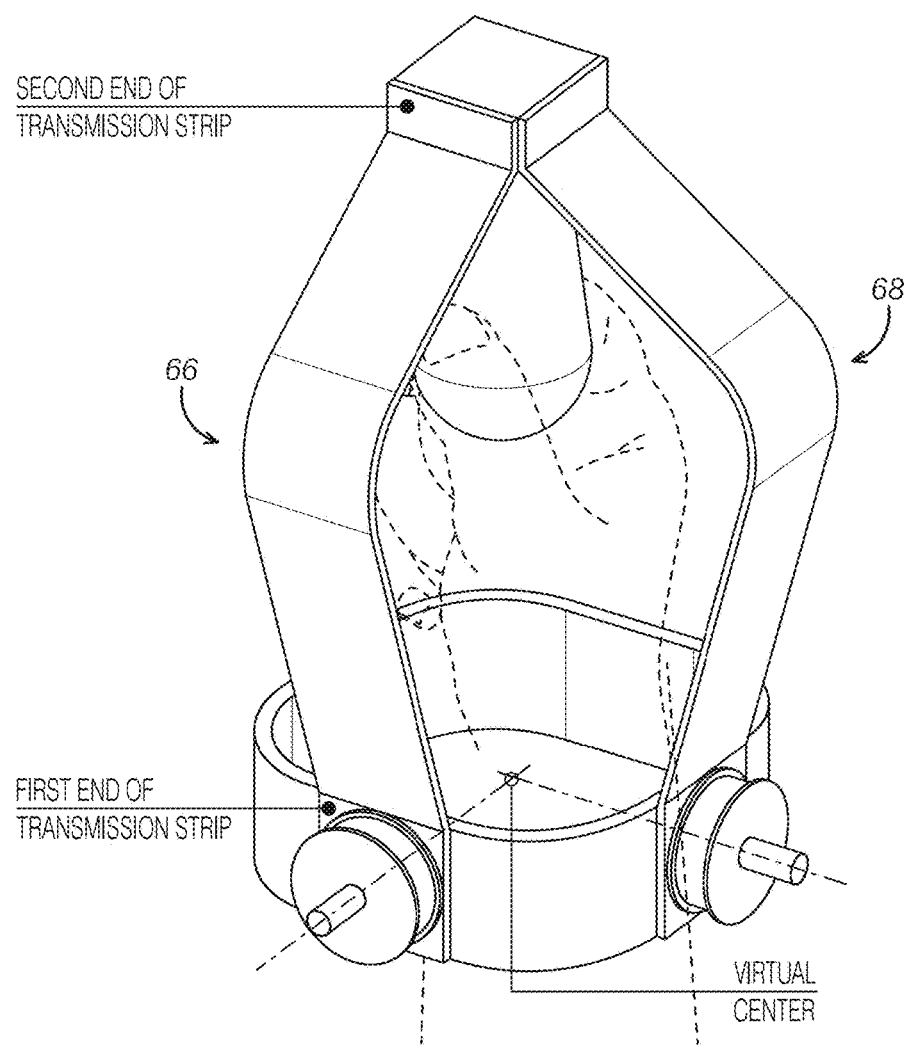
FIG. 28 is an example of a first embodiment of a parallel kinematic mechanism as described in FIGS. 12 and 13 in which input joint is configured for positioning around a human wrist.

While the functionality of the PK mechanism 16 described so far is a primarily a result of the abstract constraint map of FIG. 26, there may be additional functionalities that arise as a consequence of the actual specific geometry and construction of the intermediate rigid bodies and connectors in this particular embodiment. For example, this particular PK mechanism embodiment 16 may include two orthogonal pivot joints (70 and 72) located on the frame 18 whose extended lines of rotation intersect, and thus create a virtual center (VC) of rotation in free space. This mechanism 16 may ensure that the handle 24, is allowed to move with respect to the frame as if virtually pivoted about a point located at the virtual center even though there is no physical body, or entity, or joint at this location. The geometry of connectors 1 and 2 (i.e. pivot joints 70 and 72) is such that if their respective rotational axes are extrapolated, these axes intersect at a point in open space (i.e. virtual center) where this is no other physical entity. As shown in FIG. 28 (showing the PK mechanism 16 configured as an input joint/interface around a human wrist), the geometry of connectors 3 and 4 (i.e. flexure transmission strips 66 and 68) is such that the handle is located a bit further away from the frame and the said virtual center. This allows for a PK mechanism that not only achieves the decoupling/separation/filtering between the two rotations (rotations 1 and 2), it also provides a center of rotation for the handle (which has two rotational DoF—rotation 1 and rotation 2, or pitch and yaw) to be about a virtual center located in free space.

This functionality may be leveraged in a situation where it is desired to have the handle rotate about a certain specific location or range of locations. One example is where this mechanism 16 may be used as an input interface (as discussed above) to capture and transmit the articulation of a human wrist, for example in the control of a joy-stick, or control of a remote steerable end effector, or control of an electronic pointing device such as a computer mouse, etc. In such an application it may be beneficial to locate the virtual center provided by the mechanism in proximity to the center of human wrist joint, as the user's hand holds the handle 24. This arrangement would allow the human to articulate his/her hand about his/her wrist in a natural manner without the mechanism 16 restricting this articulation motion in any way. Furthermore, the two DoF rotational motion of the human hand about the human wrist is transferred to the handle that is held by the human hand; this two DoF rotational motion of the handle is then mechanically separated into a yaw only motion at yaw pulley 80 and pitch only motion at the pitch pulley 78. These two rotational motions thus separated are about rotational axes 74 and 78, and can then be transmitted individually with relative ease (using cables, or gears, or links, or electronically, or pneumatically, for example). These various methods of transmission are described in subsequent sections.

Figure 29A:
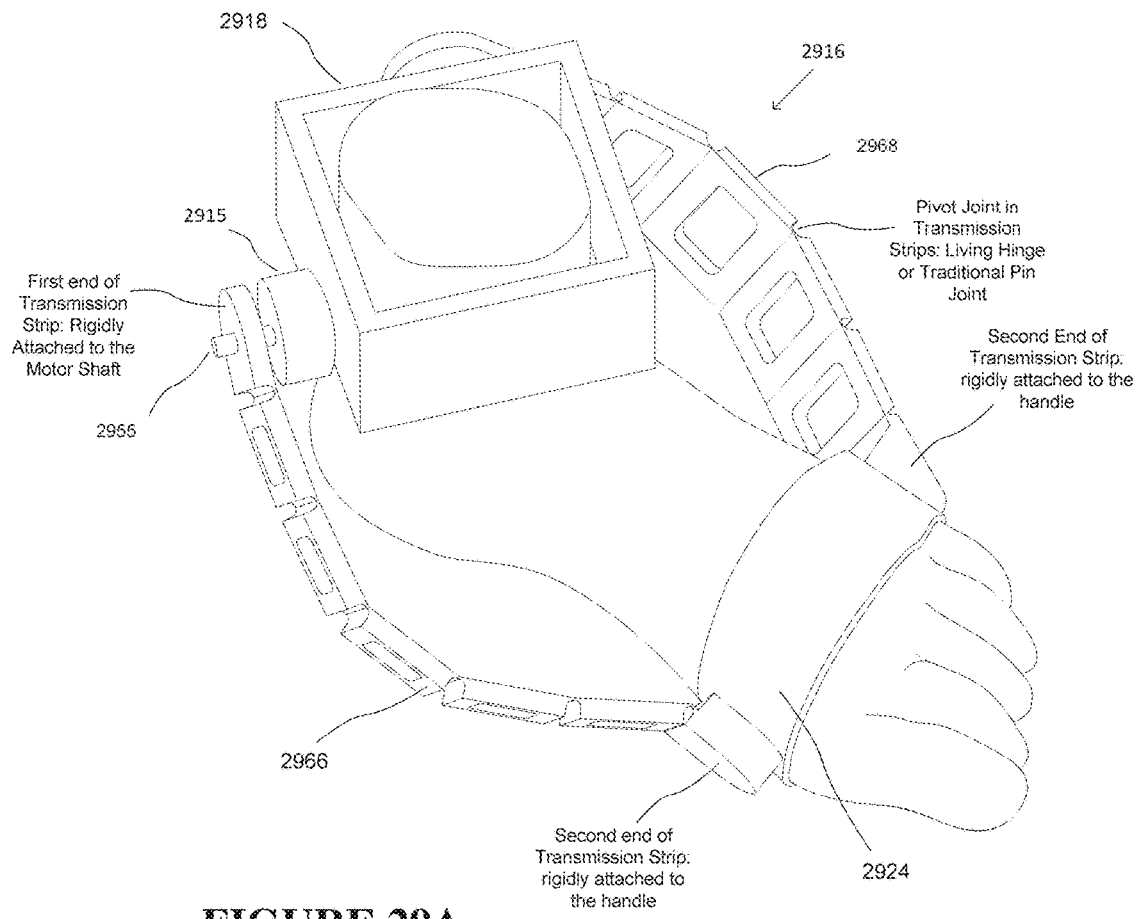
FIGS. 29A and 29B show side and top perspective views, respectively of another variation of a parallel kinematic mechanism configured for positioning around a human foot (e.g., ankle).
Figure 29B:
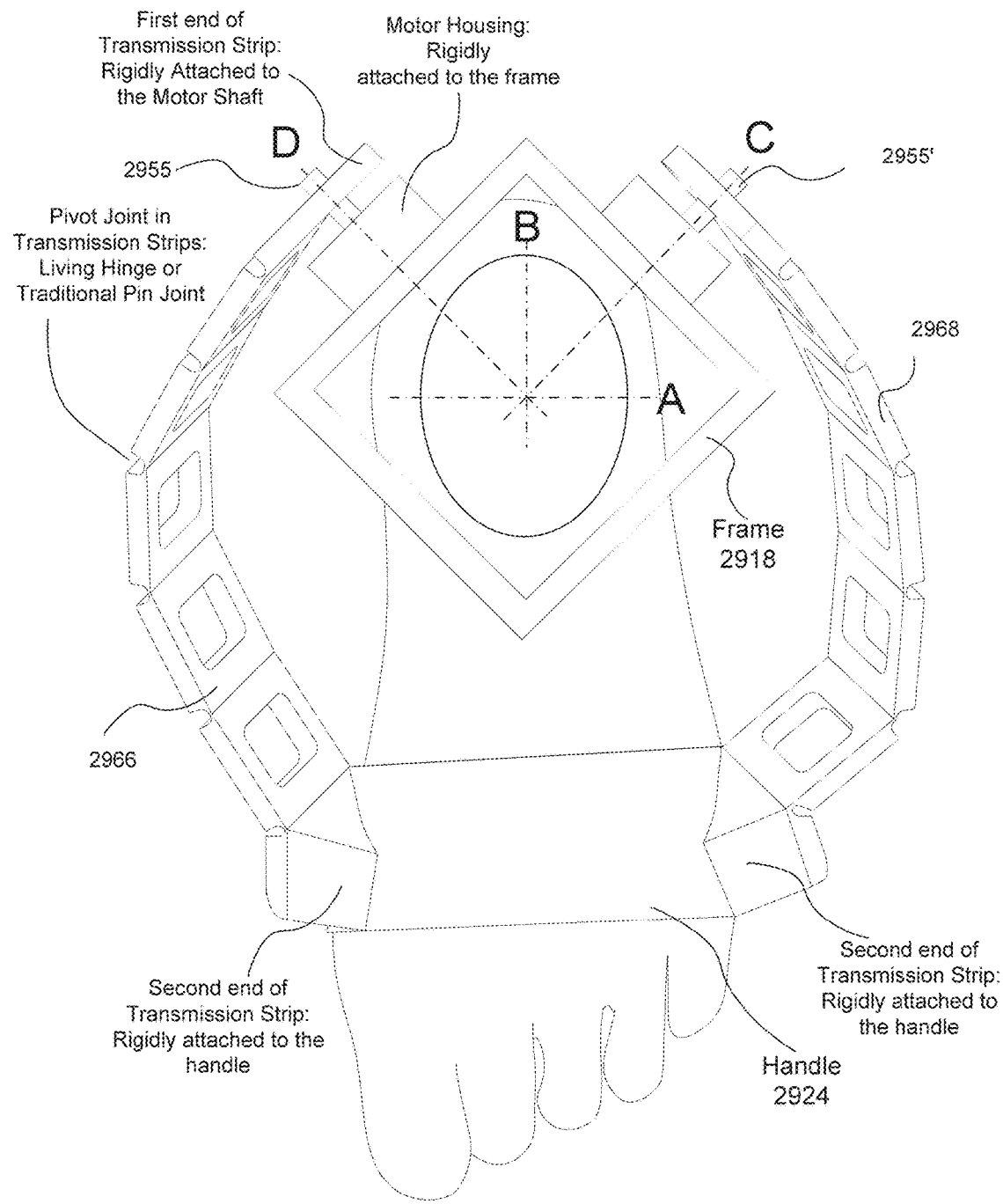

Virtual center functionality may also be beneficial when a mechanism 16 such as the one shown in FIG. 12 is used as an output interface/joint of a tool/machine/instrument/device. For example, a machine used for the rehabilitative therapy of a human articulating joint (see, e.g. FIGS. 29A and 29B showing use with an ankle joint) after injury. In FIG. 29A, the handle 2924 can interface with a human foot via straps or other securement means and the frame 2918 can interface with a human leg (e.g., ankle, shin, etc.) via straps or other securement means. The overall location of the mechanism 2916 can be such that the center of rotation of the ankle joint is approximately colocated with the virtual center provided by the PK mechanism 2916. The construction of the mechanism remains the same as that shown in FIG. 12 and follows the constraint map of FIG. 26. However, this example may include a pitch motor 2915 at the pivot joint (or connector 1) between the frame and intermediate body A (first end of transmission strip 2966). A yaw motor (not visible) may also or alternatively be included at the pivot joint between the frame and intermediate body B (first end of transmission strip 2968). As shown in FIGS. 29A and 29B, intermediate body A here is the first end of transmission strip 2966. Recall that in reference to FIG. 12, the pulley 78 and first end of transmission strip 66 are rigidly attached, and therefore constitute a single rigid body (intermediate body A). In FIGS. 29A and 29B, a pulley is not included (although it could have been shown without introducing any discrepancy with respect to previous description) and instead we just show the first end of the transmission strip 2966. A stator (or body or housing) of the pitch motor is attached to the frame while the rotor (shaft 2955) of the motor is attached to the first end of the transmission strip 2966 (intermediate body A). Similarly, a stator (or body or housing) of the yaw motor may be attached to the frame while the rotor (shaft 2955') of the yaw motor may be attached to the first end of the transmission strip 2968 (intermediate body B). The rotational joint and associated axis between the rotor and stator of the pitch motor may serve as the pivot joint (connector 1) between the frame and intermediate body A. In the other words, either pivot joints (or connector 1 and/or connector 2) are now powered or actuated joints/connectors. There are many different ways of constructing/materializing such powered pivot joints. In all cases though, the logic of the constraint map (FIG. 26) is preserved by this configuration.

The two rotations (pitch rotations and yaw rotations), independently generated by the respective actuators (pitch motor and yaw motor), are mechanically combined via the PK mechanism 2916 as described above, and are conveyed to the handle 2924. Because the handle 2924 is coupled to the foot, precise and known amounts of pitch and yaw rotations (and torques), as desired/indicated by a physician or medical personnel, can be transmitted from the motors to the foot of the patient to help build strength of the damaged ankle joint and associated tendons/ligaments/muscles. Generating a two-DoF rotation (and associated torque) at the handle directly (and therefore the human foot, in this case) is difficult, but the PK mechanism 16 permits the use of two independent single DoF rotations (produced by single DoF motors) that get combined and transmitted to the handle (and therefore foot) with relative ease. Colocation of center of the ankle joint with the virtual center ensures a natural and unrestricted range of rotation for ankle joint during such a procedure.

Figure 29C:
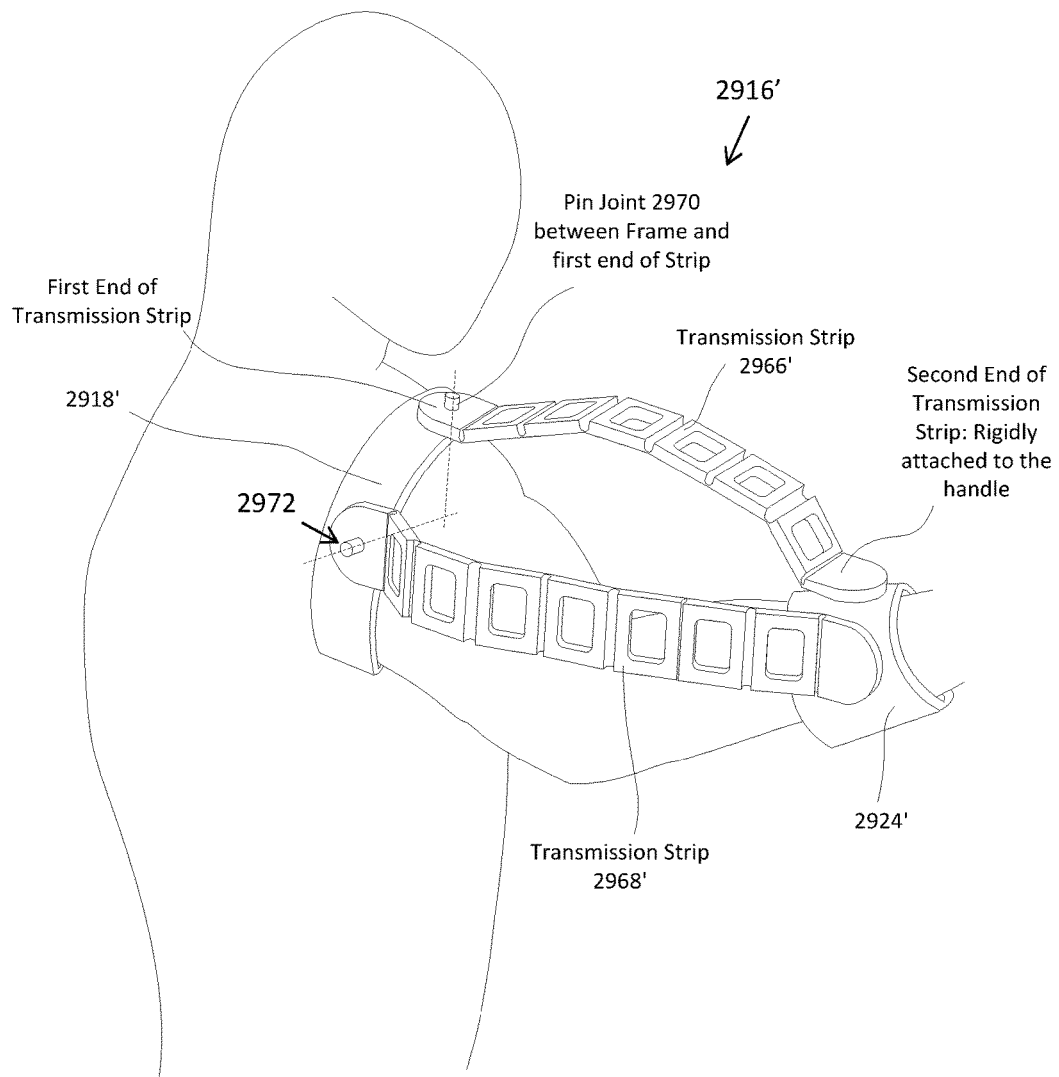
FIG. 29C is an example of a variation of a parallel kinematic mechanism configured for positioning around an arm.

In general the virtual center functionality of the parallel kinematic mechanism of FIG. 12 may be beneficial as part of a wearable output interface/joint. In addition to the leg/ankle example shown in FIGS. 29A and 29B, FIG. 29C shows an apparatus having a parallel kinematic mechanism that is configured with the constraint map of FIG. 26 for use as an output interface/joint of a power lift assist device. For example, an exoskeleton or other assistive tools/machines/devices, which may be referred to as powered exo-skeletons, may incorporate this mechanism. The mechanism 16 can be used in a similar application where the handle 2924' can interface with a human wrist/forearm location via straps or other securement means and the frame 2918' can interface with a human shoulder via straps or other securement means. The overall location of the mechanism 2916' can be such that the center of rotation of the shoulder ball and socket joint is approximately colocated with the virtual center provided by the mechanism. The construction of the mechanism remains the same as that shown in FIG. 12 and follows the constraint map of FIG. 26. A pitch motor may be included at the pivot joint 2970 (or connector 1) between the frame and intermediate body A. Additionally or alternatively, a yaw motor may be included at the pivot joint (e.g., connector 2) between the frame and intermediate body B. As shown in FIG. 29C, intermediate body A here is the same as the first end of transmission strip 2966'. Recall in reference to FIG. 12, the pulley 78 and first end of transmission strip 66 are rigidly attached, and therefore constitute a single rigid body (intermediate body A). As discussed above two rigid bodies may be considered equivalent if they are rigidly attached to each other.

In FIG. 29C, a pulley (such as the pulley 78 shown in FIG. 12) is not shown, although it could have been shown without introducing any discrepancy with respect to the previous description, and instead we just show the first end of the transmission strip. The stator (or body or housing) of the pitch motor is attached to the frame while the rotor (shaft) of the motor is attached to the first end of the transmission strip (intermediate body A). The rotational joint and associated axis between the rotor and stator of the motor serve as the pivot joint (connector 1) between the frame and intermediate body A. In the other words, this pivot joint (or connector 1) is now a powered or actuated joint. There are many different ways of constructing/materializing such a powered pivot joint, and this is just one way. In all cases though, the logic of the constraint map (FIG. 26) is preserved. A yaw motor and a yaw rotation axis may be included in the apparatus shown in FIG. 29C.

These two rotations (pitch rotations and yaw rotations), independently generated by the respective actuators (motors), are mechanically combined via the PK mechanism 2916 as described above, and are conveyed to the handle 2924'. Because the handle 2924' is coupled to the human wrist/forearm, the torques applied by these actuators can assist the user in lifting heavy weights. Applying these two torques (pitch torque and yaw torque) at the handle is difficult, but the PK mechanism 2916' permits the use of two independent rotations (and corresponding torques) that get combined and transmitted to the handle with relative ease. Colocation of center of the shoulder joint with the virtual center of the PK mechanism ensures a natural and unrestricted range of rotation for shoulder joint during such a procedure.

In an alternate application, the arrangement shown in FIG. 29C may be used as an input joint/interface as opposed to an output joint/interface. In that case, instead of actuators or motors between frame and intermediate body A, and between frame and intermediate body B, one or more sensors, such as optical encoders or potentiometers that would measure the pitch and yaw rotation angles of the shoulder joint, may be included. This information could then be transmitted electrically/electronically/wirelessly as an input to a computer controlled system. Alternatively or additionally, the pitch and yaw rotations could be mechanically transmitted via cables/pulleys, gear chain, belts, linkage, etc. to a remote end effector of interest, as described later.

The PK mechanism embodiments shown above in FIG. 29C, which may include a VC, may result in a virtual center location that remains fixed with respect to the tool frame 2918'. This may be helpful in the various application examples described above. Since the two orthogonal axes provided by the pivot joints 2970 and 2972 are fixed with respect to the frame, the location of the virtual center of rotation of the handle with respect to the frame will remain stationary throughout the range of rotation of the handle with respect to the frame provided by the mechanism 2916.

When any P-K mechanism embodying the constraint map of FIG. 26 is used an input or output joint/interface in a tool/machine/device, then, in addition to retaining all the functionality described above, there may be a need to provide the ability for the handle to translate along a third axis with respect to the frame. The third axis may be one that is orthogonal to two axes of rotations referred to in the description of the constraint map of FIG. 26.

For example, consider the mechanism of the FIGS. 12 and 13. In this example the third axis may be as shown by the dashed line 1305 in FIG. 12. If 74 and 76 are referred to as the pitch and yaw axes, respectively, then this third axis can be referred to as the roll axis (per generally used and known terminology). Per the constraint map of FIG. 26, connector 3 (i.e. the transmission strip 66 of FIG. 12) it is stiff about the pitch axis or rotation direction, which is the same as saying that it transmits pitch rotation; it is also compliant about the yaw axis or rotational direction, which is the same as saying that it absorbs or does not transmit yaw rotation.

Similarly, connector 4 in the constraint map of FIG. 26 (i.e. the transmission strip 68 of FIG. 12) is stiff about the yaw axis or rotation direction, which is the same as saying that it transmits yaw rotation; also it is compliant about the pitch axis or rotational direction, which is the same as saying that it absorbs or does not transmit pitch rotation. Additionally, these two connectors (i.e. transmission strips) may be compliant in translation along the roll axis, which is the same as saying that they allow translation along the roll axis. In fact, the geometry of the connectors/transmission strips 66, 68 (as shown in their bent configuration in FIG. 17) is such that they do not impose any constraint against translation along the roll axis, allowing for handle 24 to adjustably be located within a certain range along the roll axis with respect to the frame 18. Thus, the handle 24 can translate towards or out away from the frame 18, while retaining all relevant functionality described above. In other words, the PK mechanism of FIG. 12 and the examples shown in FIGS. 28 and 29A-29C also provides a translational DoF along the roll axis between the handle and the frame.

One example where such added functionality would be useful can be described with reference to FIG. 28, to allow differently sized users to operate the apparatus. For example, when this PK mechanism is used an input interface/joint in a tool/machine/device, where a user's hand holds the handle and the user's forearm interfaces with the frame, thereby approximately positioning the virtual center provided by the PK mechanism close to the center of his/her wrist joint. In such a situation, a translational DoF provided by the PK mechanism along the roll axis, may allow users of different hand sizes to interface with this PK mechanism with relative ease. A user with a longer hand can hold the handle a bit further away from the frame, while retaining an approximate colocation between the mechanism's VC and his/her wrist. Similarly, a user with a shorter hand can hold the handle a bit closer to the frame, while retaining an approximate colocation between the mechanism's VC and his/her wrist. This would maintain all the functionality of the mechanism as described above without restricting the range of rotation about the pitch and yaw axes.

Similarly, if this PK mechanism were used around a human foot (as in the output joint/interface shown in FIGS. 29A and 29B), then the additional translational DoF along roll axis between the handle and frame makes the PK mechanism easily adaptable to a wide range of foot sizes, without any loss in the above-described functionality of the PK mechanism. The translational DoF along the roll axis may be relevant and useful even when a human hand or foot is not involved.

When any parallel kinematic (PK) mechanism following the constraint map of FIG. 26 is used an input or output mechanism/device in a tool, machine or device, then in addition to retaining all the functionality described above there may be a need to provide the ability for the handle to transmit a rotation from the handle to the frame (and vice versa) about a third axis. The third axis may be one that is orthogonal to two axes of rotations referred to in the description of the constraint map of FIG. 26.

Using a specific example to explain this, consider the mechanism of the FIGS. 12 and 13. In this example, the third axis may be as shown by the dashed line 1305 in FIG. 12. If 74 and 76 are referred to as the pitch and yaw axes, respectively, then this third axis can be referred to as the roll axis as discussed above. Per the constraint map of FIG. 26, connector 3 (i.e. the transmission strip 66 of FIG. 12) is stiff about the pitch axis or rotation direction, which is the same as saying that it transmits pitch rotation; also it is compliant about the yaw axis or rotational direction, which is the same as saying that it absorbs or does not transmit yaw rotation. Similarly, connector 4 (e.g. the transmission strip 68 of FIG. 12) is stiff about the yaw axis or rotation direction, which is the same as saying that it transmits yaw rotation; also it is compliant about the pitch axis or rotational direction, which is the same as saying that it absorbs or does not transmit pitch rotation. Additionally, either or both these connectors (i.e. transmission strips) may be stiff in rotation about the roll axis, which is the same as saying that they transmit rotation about the roll axis. In fact, the geometry of the connectors/transmission strips 66, 68 (as shown in FIG. 12) is such that they can transmit roll rotation. The individual pivot joints in each transmission strip (described in detail below) may be, e.g., traditional pin joints or a living hinge joint. As long as each of these individual joints constrains (and therefore transmits) roll rotation, the entire strip will also do the same. However, strictly speaking only one of the two strips needs to constrain (therefore transmit) roll rotation. In practice, it may be beneficial to have both strips constrain (and therefore transmit) roll. In practice, it might be even more beneficial to have four transmission strips constrain (and therefore transmit) roll, as in the case of the PK mechanism shown in FIGS. 30A and 30B. With such transmission strips, the PK mechanism of FIG. 12 (or alternatively FIGS. 28, 29A-29C or alternatively 30A and 30B) allows rotations along pitch and yaw axes (or more generally rotation 1 and rotation 2 in FIG. 26); in other words it provide DoF along these two rotational directions; AND at the same time offer a constraint along the roll axis (or more generally rotation 3) between the handle and the frame; in other words, it transmits rotation 3 from the handle to the frame and vice versa.

One example where such added functionality would be useful can be described with reference to FIG. 28. If in a certain application, when this PK mechanism is used an input interface/joint in a tool/machine/device, where a user's hand holds the handle and approximately positions the virtual center provided by the mechanism close to the center of his/her wrist joint. In such a situation, transmission of roll provided by the PK mechanism from handle to frame along the roll axis, allows the user to affect the roll of the frame by just rolling the handle with his/her thumb, fingers, and/or hand. Thus, while maintaining all the functionality of the mechanism as described above, this feature provides the additional functionality where the user can drive/affect the roll of the frame by providing a roll rotation at the handle. In this case, the interface/coupling provided by the arm attachment member between the proximal end of the frame and the user forearm should allow at least a roll rotational DoF, to allow the frame to freely rotate about the roll axis with respect to the forearm.

Reference to a user and user's hand and wrist was made simply to explain significance of the additional functionality. Such functionality is relevant even when a human hand is not involved.

Figure 30A:
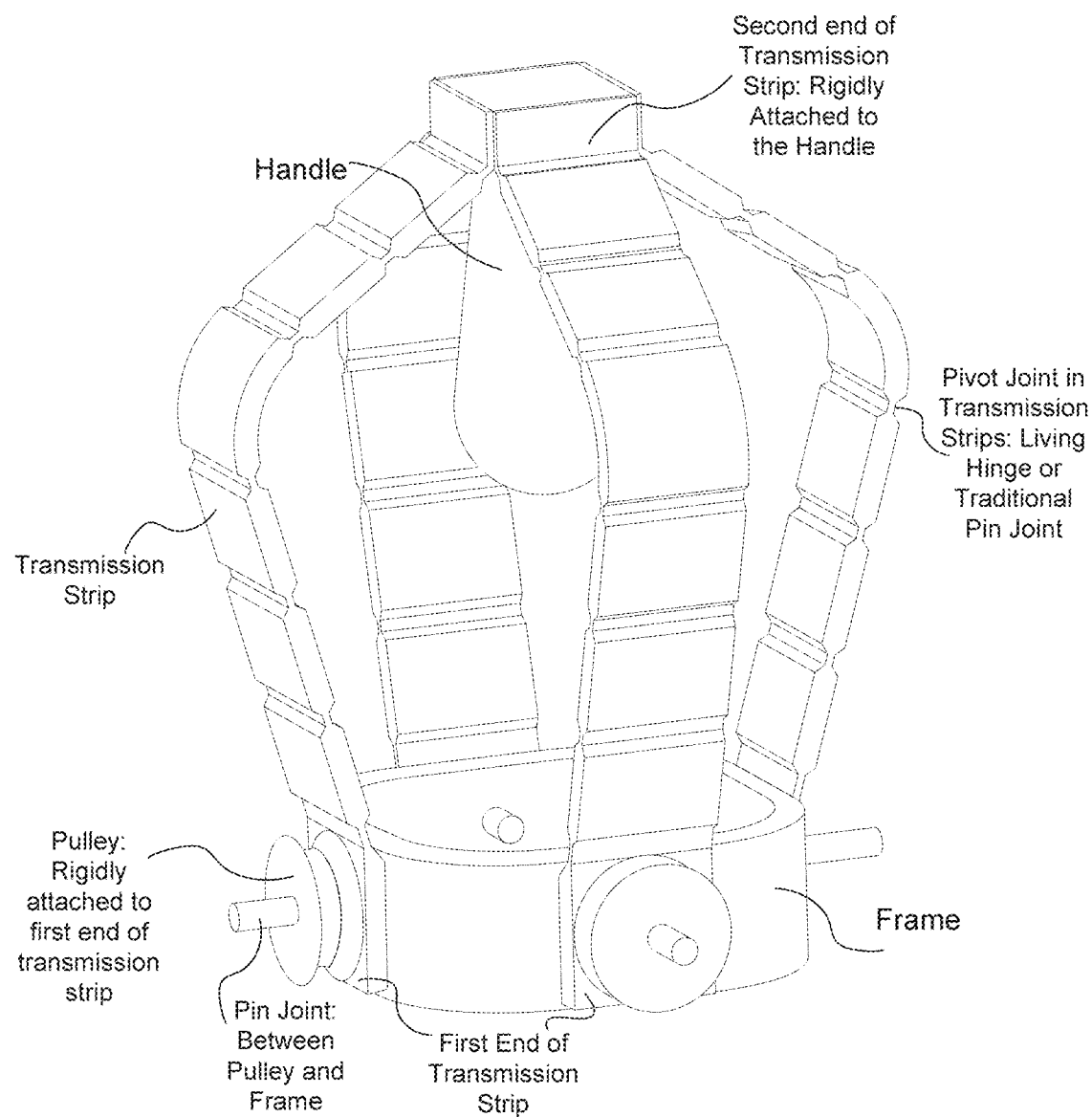
FIGS. 30A and 30B show another example of a parallel kinematic mechanism similar to the one shown in FIGS. 12 and 13, configured to be worn around a user's wrist so that the handle may be gripped by a hand.
Figure 30B:
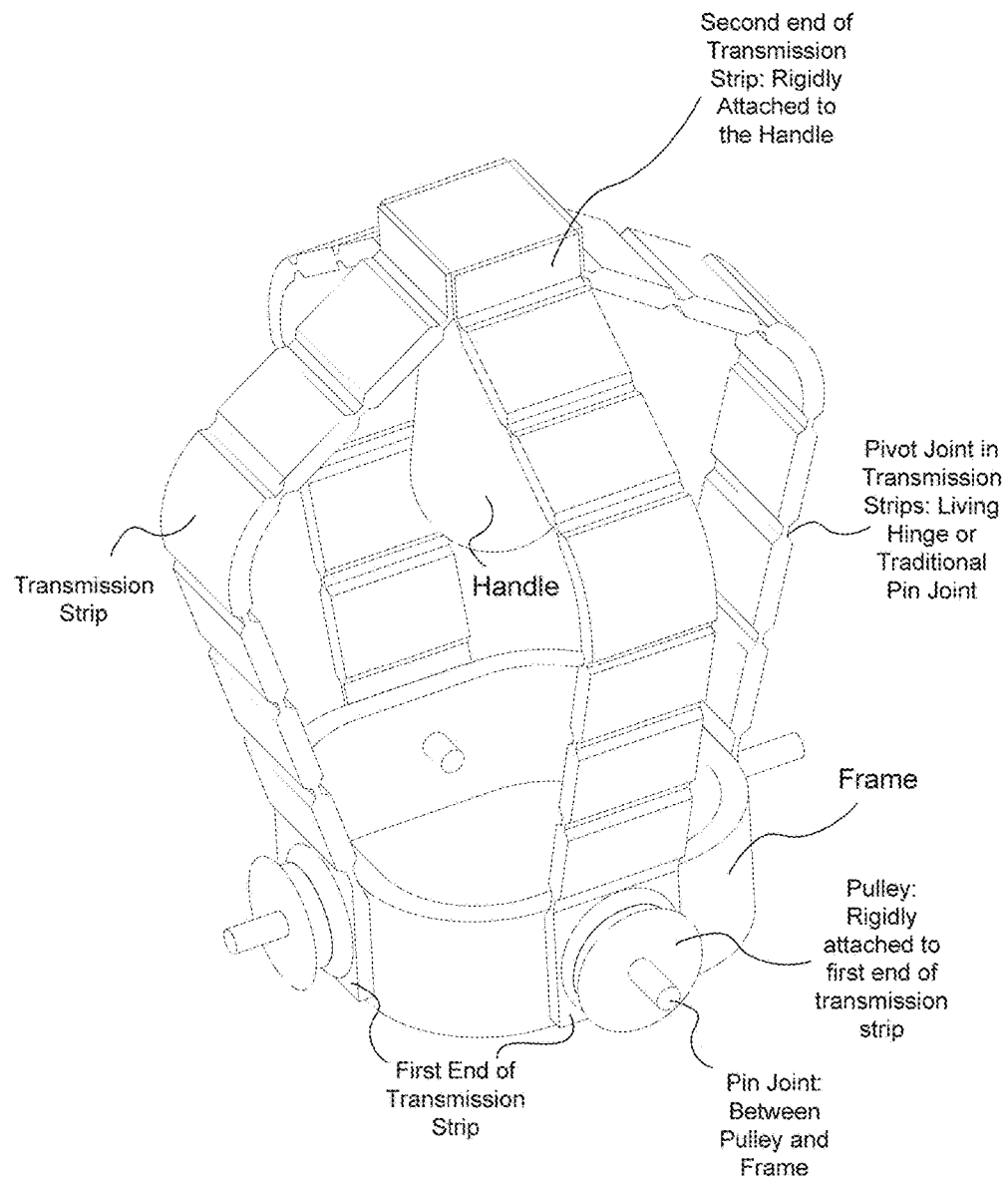

A physical embodiment that corresponds to the expanded constraint map of FIG. 27 is shown in FIGS. 30A and 30B. Here instead of two parallel mechanical connection paths between the frame and the handle, there are four independent parallel paths, as diagrammatically shown in FIG. 27.

Figure 31A:
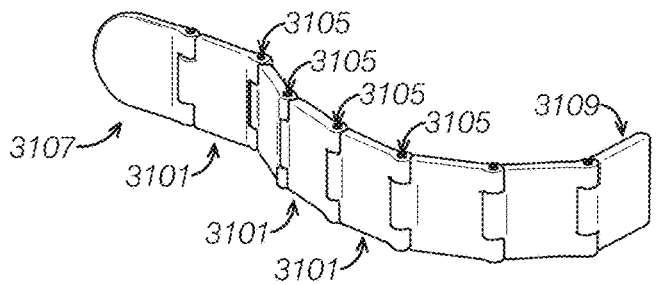
FIG. 31A shows an example of a transmission strip formed from a plurality of rigid members that are connected in a line at hinge points that are, in this example, aligned to have geometrically parallel axes of rotation.
Figure 31B:
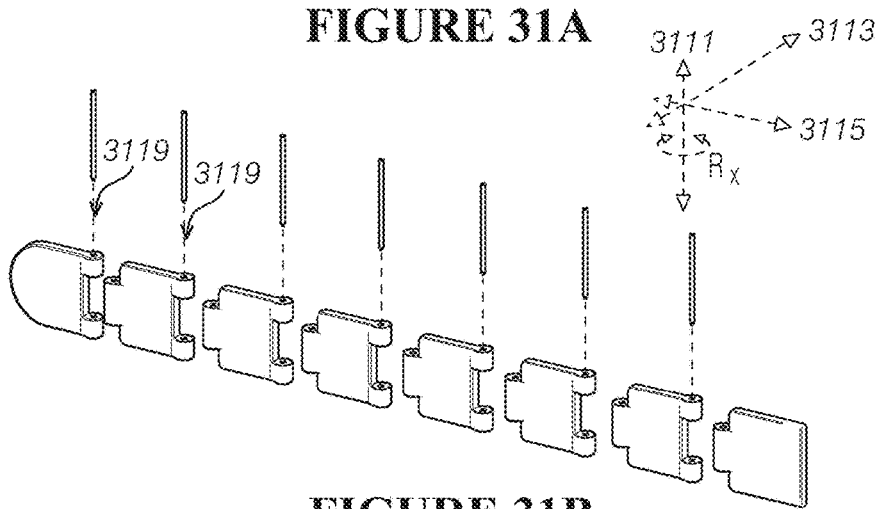
FIG. 31B is an exploded view of the transmission strip of FIG. 31A.

For the flexure strip based PK mechanisms shown in FIGS. 12, 13, 28 and 29A-29C, the flexure transmission strips can be constructed/realized in multiple different ways. FIGS. 31A and 31B show one variation of flexure transmission strips having rigid links 3101 separated by pins forming pivot joints 3105. The ends 3107, 3109 of the flexure transmission strips may be attached (e.g., rigidly attached) as described above. The transmission strip may be a joint or connector that allows certain degrees of freedom and constrains the remaining degrees of freedom. For example, referring to FIG. 12, the transmission strip 66 (connector 3) allows yaw rotation and constrains pitch rotation and the transmission strip 68 (connector 4) allows pitch rotation and constrains yaw rotation. In some variations, the basic construction of a strip comprises an alternating chain of rigid segments/links/elements and hinge/pivot/pin joints; this can be realized in many different ways. One example is shown in FIG. 31A and an exploded view of the same configuration is shown in FIG. 31B.

In use, the first rigid element 3107 in the transmission strip, which may also be referred to as the first end of the transmission strip, is attached to an intermediate body (A or B) of the PK mechanism (e.g., as shown in FIGS. 12, 28 and 29A-29C), and the last rigid element 3109 in the transmission strip, which may also be referred to as the second end of the transmission strip, is attached to the handle of the PK mechanism, as shown in FIGS. 12, 28 and 29A-29C. The rigid segments 1301 are rigid in a practical sense, i.e. much stiffer than the other associated elements/features in the construction. For example, each pivot joint provides low resistance or low stiffness in one rotational direction; in contrast, the rigid segments have a much higher stiffness about this rotational direction and a similarly high stiffness along all other directions. The rigid segments may be made out of any material such as plastic (e.g. delrin, nylon, polypropylene, ultem, polyethylene, etc.), metal (e.g. steel, aluminum, copper, etc.), wood, ceramic, composite, etc. and may be provided with a geometry that ensures maximum rigidity with minimum material utilization.

In a transmission strip such as the one shown in FIG. 31A, there will are at least two rigid segments interconnected by one pivot joint. In general, there can be many alternating rigid segments and pivot joints, dictated by the nature of application that the PK mechanism would be employed in.

All the pivot joints in a transmission strip have rotational axes that are aligned in the same direction (e.g. rotation direction $R_x$) and are therefore parallel, see, e.g., the axes X (3111), Y (3113), Z (3115) in FIG. 31B. In other words, all the pivot joints have a rotational DoF about this rotation axis X (e.g. the pivot joints of the transmission strip 68 in FIG. 12 have a rotational axis along the pitch rotation direction). As mentioned, the pivot joints may have axes that are not all parallel to each other.

The constraint map of FIG. 26 calls for a connector (e.g. connector 3 or 4) that at the very least allows one rotation, e.g. about direction X (3111) and constrains a second rotation, e.g. about direction Y (3113), between its first end and its second end. Note that between connectors 3 and 4, the definition of directions X and Y is interchanged. However, in addition to these two directions, certain additional functionality of the PK mechanism may require the connectors 3 and/or 4 to also constraint a third rotation (e.g. about direction Z 3115 in FIG. 31B). Rotation between first end and second end of the transmission strip about direction Z may also be referred to as twisting of the transmission strip. In many applications it may be important to transmit the third rotation from a handle to frame or vice-versa, as described earlier. In those cases, it becomes important that the construction of the transmission strip (at least one of the strips, and potentially all of the strips) be such that the relative rotation between the first end and second end of the strip about the Z direction is constrained, when the strip is bent (e.g., FIG. 31A) as well straight (e.g., FIG. 32A). In other words, the twisting stiffness or resistance of the transmission strip may be high.

For example, compare the transmission strip 66 (connector 3) of FIG. 12 to transmission strip of FIG. 31A. A first end of strip 66 (connector 3) is rigidly connected to pulley 78 (intermediate body A), which in turn is connected to frame 18 via a pivot joint 70 (connector 1). Pivot 70 allows rotation about pitch axis (rotation 1) and constrains rotation about yaw axis (rotation 2). Strip 66 (connector 3) itself allows (i.e. is compliant) about yaw axis (rotation 2) and restricts (i.e., is stiff) about the pitch axis (rotation 1). When comparing to FIG. 31B, rotation 2 is direction X and rotation 1 is direction Y. This description would be reversed when considering the transmission strip 68 (connector 4) of FIG. 12.

In general, the pivot joints and rigid segments can be realized in one of many different ways. For example, a simple pivot joint may be used that employs a pin as shown in FIGS. 31A and 31B. This is a traditional pin joint. Advantages of this choice include that this joint provides very low stiffness or resistance about rotational axis X and very high stiffness in the other rotational directions, Y and Z. This helps meet the functionality requirement of the overall strip that it should allow rotation X and constrain rotation about orthogonal directions Y and Z. In reference to the transmission strips described herein, the term "axis" generally refers to a specific line; for example, in FIG. 31B, each line 3119 is in the same direction (e.g., direction X, 3111) but is a distinct axis.

Transmission strips such as those shown in FIGS. 31A and 31B may have some small friction in the joints, resulting in some of the joints to be stuck in a certain position. This can result in the entire strip getting collapsed into an undesired shape. This issue can generally be addressed via appropriate lubrication, material choice, and dimensional tolerancing of the pins and mating holes. Furthermore, to ensure that the transmission strip retains a gradual shape rather than collapse, a light (weak) spring action may be included in bending about the X direction. This spring action may provide a restoring effect to the shape of the strip. This can be accomplished via tiny torsional springs incorporated in each individual pivot joint. Alternatively, it can be accomplished by coupling a flexible element along the length of the strip, where this flexible element offers some small bending stiffness with respect to direction X. This flexible element could be a thin wire, rod, strip, tubing, coil-spring, etc. made of metal or plastic or other appropriate materials. This element would provide a spring like action to the overall strip, providing form and shape so that the strip does not collapse. In given applications such as FIGS. 28 and 29A-29C, this defined shape and absence of collapsing may help avoid interference with, for example, the human hand or foot that is interfaced with the parallel kinematic mechanism.

Other examples of a transmission strip construction where the pivot joints employ pins or traditional hinges are shown in FIGS. 32A-33C.

For example, other pivot joint designs are shown in FIG. 32A-33C where the pivot joint employs a pin but the rigid segments are shaped such that bending in only an upwards direction (arrows in FIG. 33C) is allowed and bending downwards is restricted by interference between consecutive rigid segments.

Figure 32A:
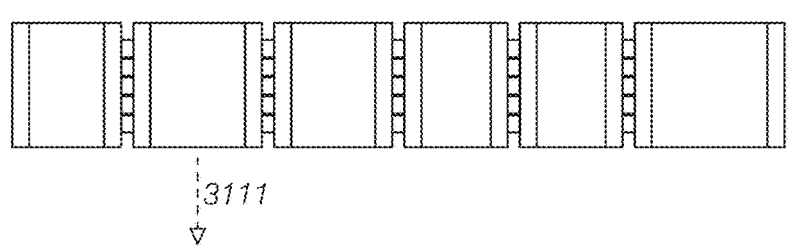
FIG. 32A is another example of a transmission trip similar to the one shown in FIGS. 31A and 31B, having chamfered or beveled edges that are hinged.
Figure 32B:
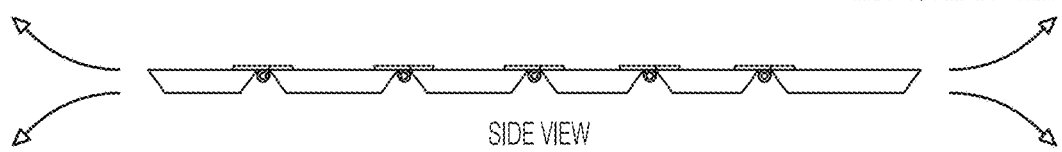
FIG. 32B shows a side view of the transmission strip of FIG. 32A.
Figure 33A:
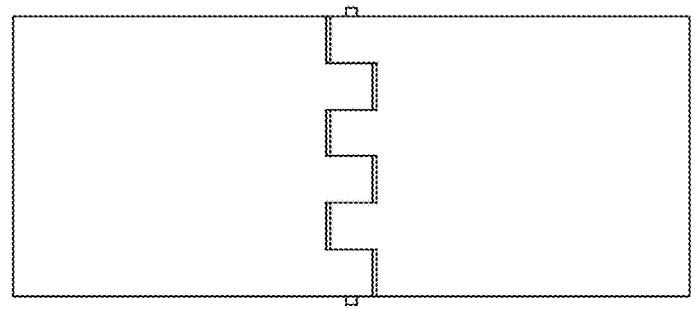
FIGS. 33A-33C illustrate an example of a pivoting joint, in top, side and side perspective views, that includes rigid segments that are hinged by a pin to allow rotation.
Figure 33B:
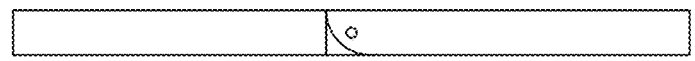
Figure 33C:
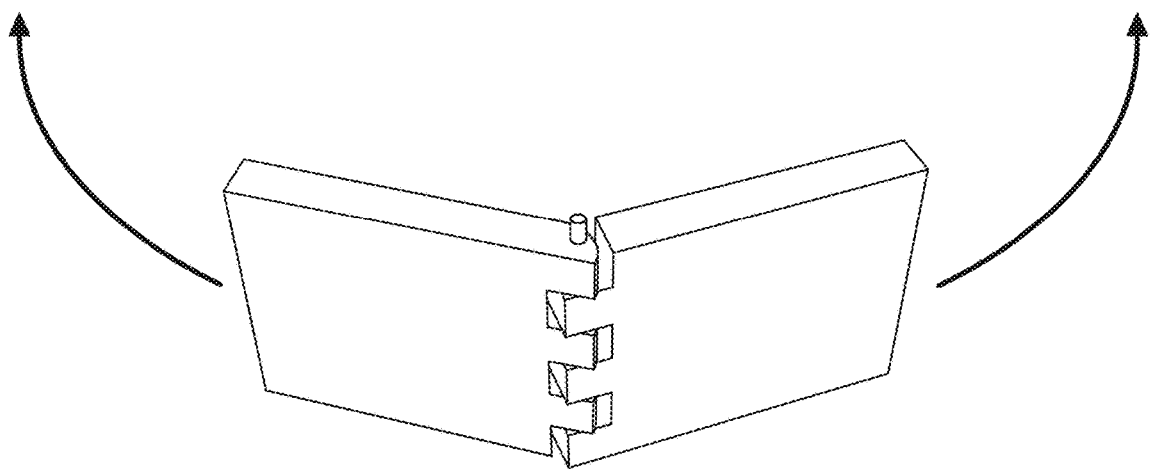

All of the pin-based pivot designs shown above provide excellent stiffness about rotational axes Y and Z. In other words, bending stiffness about Y direction and twisting stiffness about the Z direction are very high, as desired by the constraint map and functionality described previously. Rotation about X direction is allowed, or in other words, stiffness/resistance in bending about direction X is low. Additionally, this construction constrains relative translations, between the first and second ends of the strip, along the Y and Z directions. Relative translation between the first and second ends of the strip along the X direction is constrained/restricted (i.e. high stiffness) when the strip is laid out straight (e.g. as shown in FIGS. 32A, 33A and 33B). However, when the strip is in a bent configuration (e.g. FIG. 31A), relative translation between the first and second ends of the strip along the X direction becomes allowable.

A transmission strip may alternatively or additionally include a living hinge (also known as flexure hinge) as the pivot joints. The rigid segments may be assembled with the living hinges (i.e., the rigid segments and living hinges may be separate components that are sequentially assembled to construct a transmission strip). Alternatively, the transmission strip can be made monolithic i.e. the rigid segments and pivot joints made out of the same material by simply varying the geometry along the length of the strip. The advantage of a living hinge is that it is free of friction, wear, and backlash. Furthermore, a living hinge may provide some inherent bending stiffness about the X rotational direction. This results in the overall transmission strip assuming a well-defined shape and not collapsing on itself. In some applications, such as the apparatuses shown in FIGS. 28 and 29A-29C, this defined shape and absence of collapsing may help avoid interference with, for example, the hand or foot that is interfaced with the parallel kinematic mechanism. A monolithic transmission strip may be made of plastic, metal, or composite materials. Or alternatively a transmission strip with living hinges may be assembled from discrete components of living hinges and rigid segments.

A monolithic transmission strip that employs flexure hinges as the pivot joints is shown in FIGS. 34B-41. As shown progressively in FIGS. 34A and 34B, a strip of appropriate material (e.g., plastic) with uniform thickness may be machined to a smaller thickness at specific locations to produce living hinges at these locations. The material has to be chosen appropriately to provide adequate strength and robustness against failure, fatigue resistance, small rotational stiffness in the desired bending direction X, and high rotational stiffness about the other two rotational directions. Materials that are typically suitable for living hinges include plastics such as polypropylene, polyethylene, and polyolefin. The material may bend along the living hinge axes, all along the X direction, while the thicker sections of the strip will serve as the rigid sections (for example 3406 in FIGS. 34D and 35). One of the advantages of a monolithic living hinge transmission strip design is that it can be fabricated as a single piece/component via a cost-effective, volume-production method such as injection molding. Some more examples of such transmission strips are shown in FIGS. 34D, 35, 37A-37D, 39 and 40.

Figure 34A:
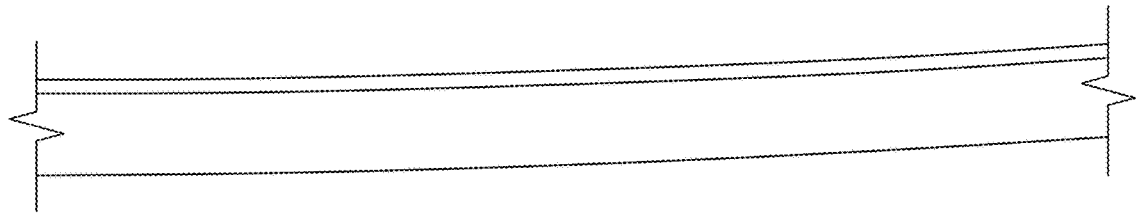
FIGS. 34A-34D illustrate a living hinge that may be used, e.g., to form a transmission strip as described herein. FIG.
Figure 34B:
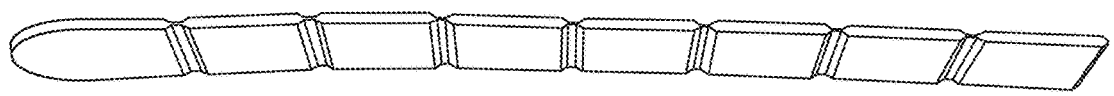
Figure 34C:
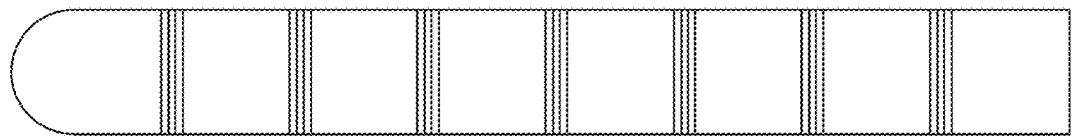
Figure 34D:
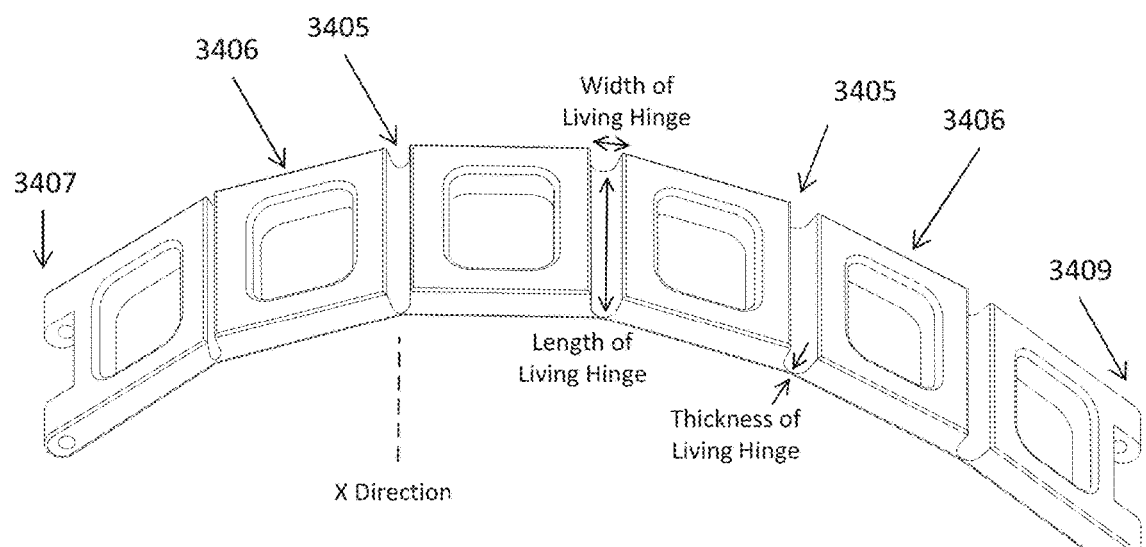
Figure 35:
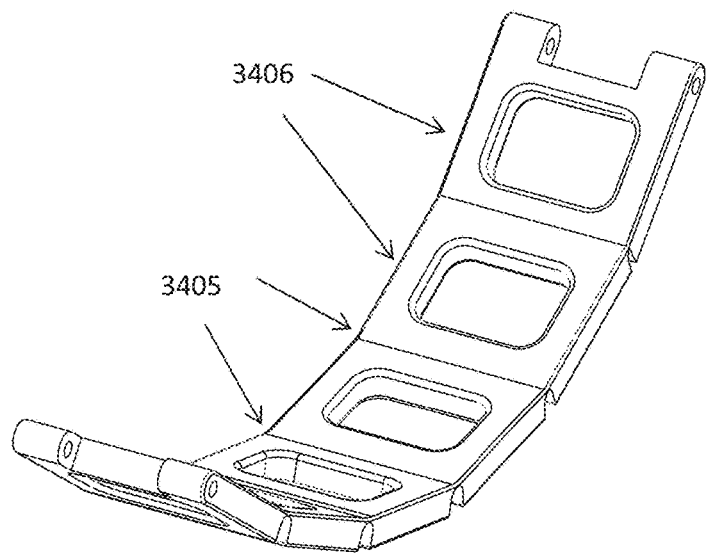
FIG. 35 illustrates a bottom perspective view of a transmission strip such as the transmission strip shown in FIG. 34D flexing in a first direction.

For example in FIGS. 34D and 35, the transmission strip is formed from a polymeric (e.g., plastic) material having living hinge regions 3405. In these examples the strip includes pockets or windows cut out in the rigid segments to provide weight reduction while maintaining the desired stiffness/rigidity is maintained. The first end and second end of the transmission strips show a pin based pivot joint 3407, 3409 for interfacing with other bodies such as the handle and transmission pulleys (intermediate bodies A or B, in FIG. 12).

Figure 36:
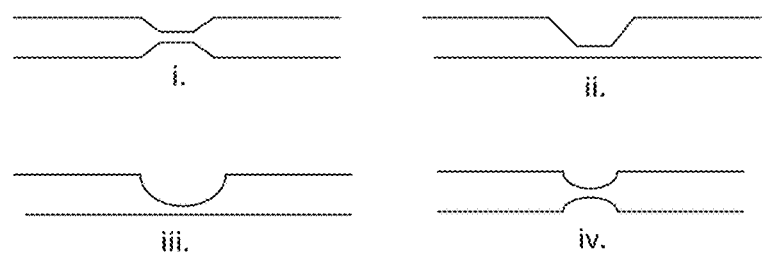
FIG. 36 illustrates cross-sectional views through variations of living hinge profiles that may be used as part of any of the transmission strips described herein (along the longitudinal axis of a transmission strip).

FIG. 34D also shows that in any of the transmission strips described herein, different pivot joints may be used, i.e. in the same strip one could use a combination of pin based pivot joints and living hinge based pivot joints. Furthermore, a living hinge may be optimized to reduce stress, increase fatigue life, reduce or optimize stiffness in rotation/bending about X direction, maximize stiffness in rotation (bending about Y and twisting about Z). For example, the thickness, width, and length of the living hinge may be varied, as shown in FIG. 34D. Furthermore, various shapes of the living hinge may be used, as shown in FIG. 36 (i)-(iv). In this example, FIG. 36 (iii) is similar to the variation shown in FIGS. 34D, 35, 38. In FIG. 36, sections through the living hinge region show that the depth, profile and width may be varied.

Figure 37A:
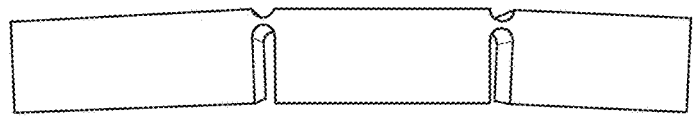
FIGS. 37A-37D show examples of variations of living hinges forming transmission strips.
Figure 37B:
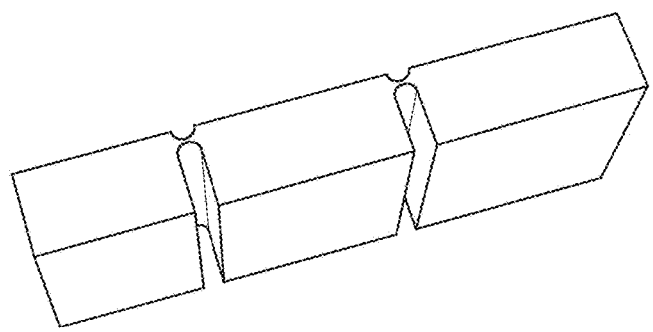
Figure 37C:
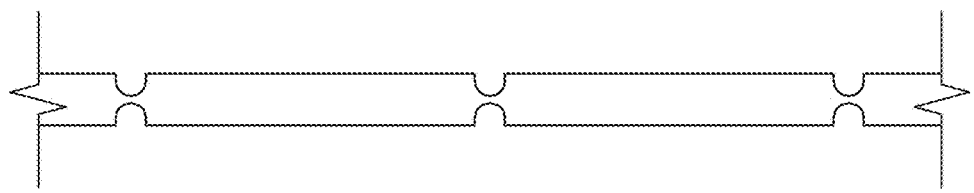
Figure 37D:
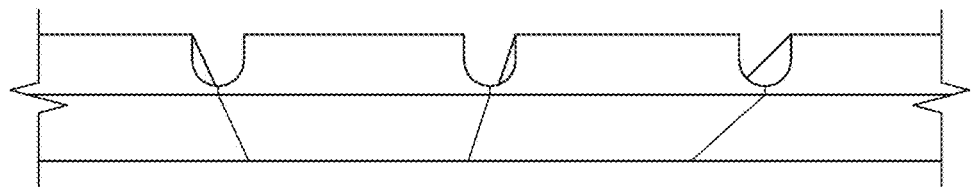

FIGS. 37A-37D show other variations of living hinges or flexure hinges. In FIGS. 37A and 37B, for example, the strip has a deep grooves on one side to allow bending in the upwards direction but limits bending in the downward direction. The strip in FIG. 37C shows a symmetric living hinge geometry that allows upwards as well as downwards bending. FIG. 37D shows a living hinge having a smooth surface on the bottom side, which might be desirable in certain applications. For example, in the FIGS. 12, 18 and 29A-29C, it may be desirable to keep the side of the transmission strip that faces the user's hand smooth to avoid pinching.

Figure 38:
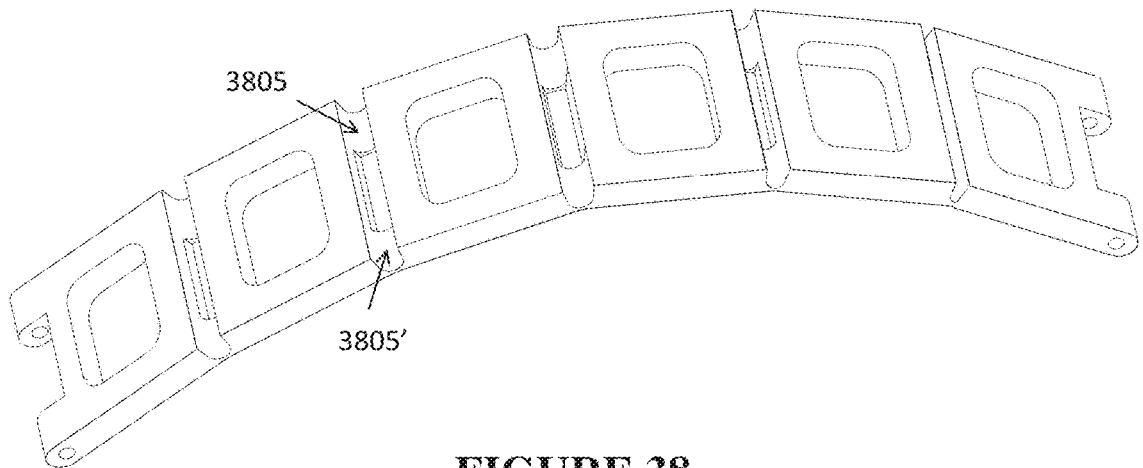
FIG. 38 is a top perspective view of a transmission strip such as the one shown in FIG. 35, flexing in a first direction.

Other variations of the living hinge include a geometry where the living hinge includes discrete sections extending between the rigid portions. For example, FIG. 38 shows transmission strips with living hinges, each of which are formed with two segments 3805, 3805' along their length (as defined in FIG. 34D).

Figure 39:
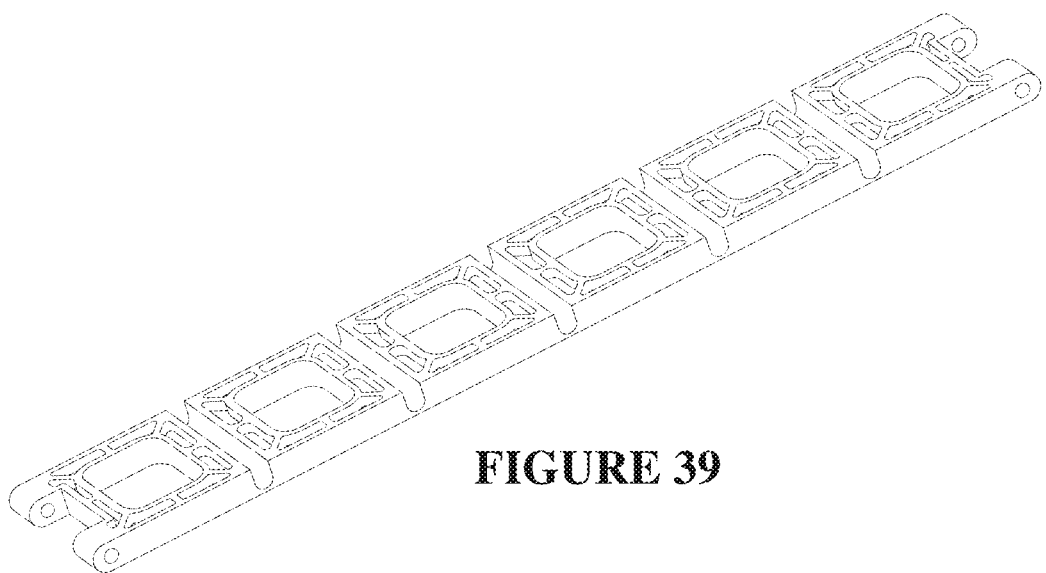
FIG. 39 is a schematic of another example of a transmission strip including a living hinge between rigid regions; the rigid regions may include opening therethrough, which may reduce weight without unduly compromising strength.
Figure 40:
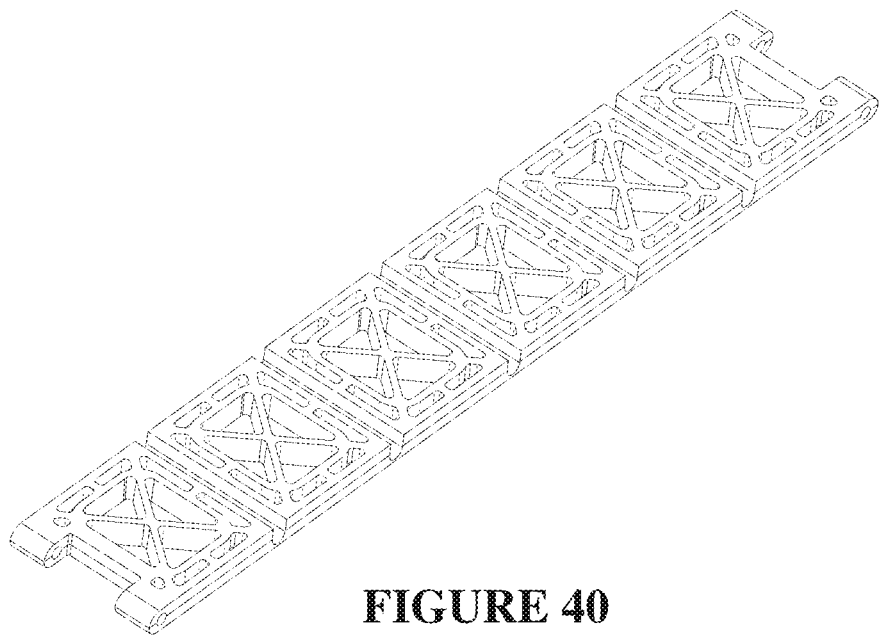
FIG. 40 is a schematic of another example of a transmission strip including a living hinge between rigid regions.

The shape and geometry of the rigid section may also be varied. As mentioned above, the transmission strips may include rigid segments that have cut-outs or windows through them. The rigid segments may also be made of the same material as the flexure hinge. The base material (e.g., plastics, etc.) may be made more rigid by making the entire strip thicker; the weight may be reduced by including cut-out windows in the rigid segments. These window cutouts may help reduce the weight but do not significantly affect the stiffness of the rigid segments, such as shown in FIGS. 39 and 40. Other geometric features (cut-outs, holes, windows, patterns, truss structure, ribs, etc.) may be created on the rigid segments for reasons of functionality, manufacturability, aesthetics, etc. In particular, the transmission strips and therefore the rigid segments may have a high stiffness in bending about the Y direction and twisting about the Z direction.

FIGS. 39 and 40 show configurations of transmission strips where the rigid segments have a geometry that reduces weight, yet provide structural stiffness especially for twisting about the Z direction, and are conducive to a manufacturing process such as plastic injection molding.

Figure 41:
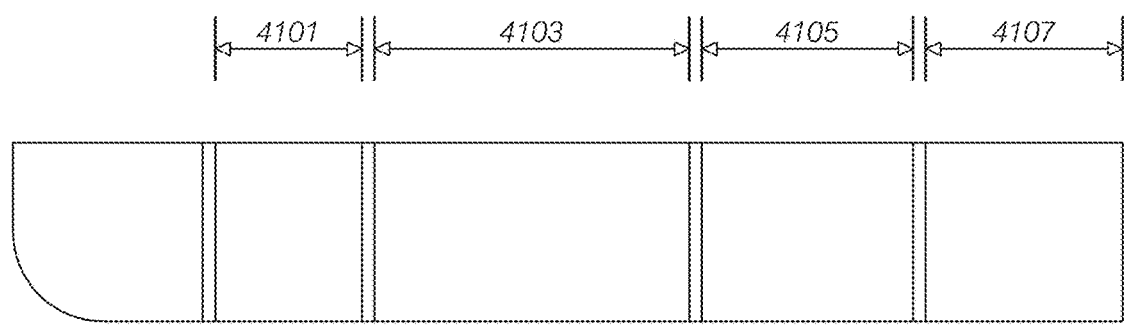
FIG. 41 is a bottom view of another example of a transmission strip.
Figure 42A:
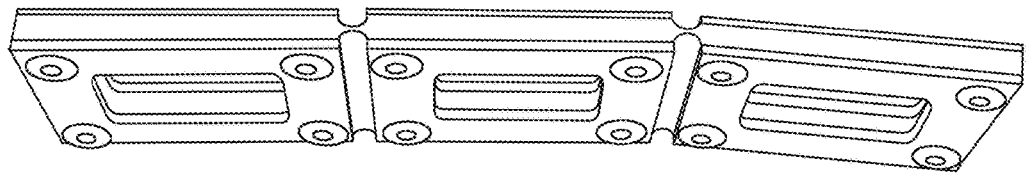
FIGS. 42A-42D illustrate other variations of a transmission strip having metal-reinforced rigid segments.
Figure 42B:
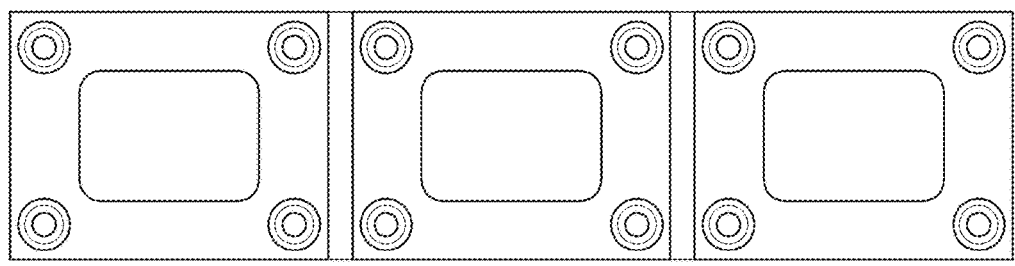
Figure 42C:
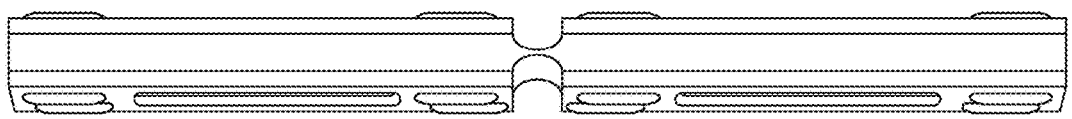
Figure 42D:
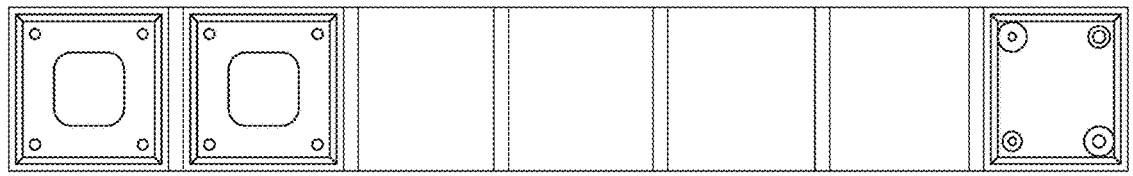

The lengths of the rigid segments 4101, 4103, 4105, 4107 may be varied from one segment to another segment, as shown in FIG. 41. Such variation, which also affects the number and location of the pivot joints along the length of the strip, can help optimize functionality (desired stiffness characteristics), manufacturability, aesthetics etc. of the transmission strip, including avoiding interference with, for example, a hand or foot that is interfaced with the parallel kinematic mechanism under consideration.

Furthermore, the shape of the rigid segments may be varied from one segment to another segment. Although most figures here show the rigid segments to flat and square/rectangular in shape; in practice, they may have any general shape dictated by the application as long as they are adequately stiff. One example may be seen in the transmission strips of FIG. 12 and FIGS. 30A and 30B, where the rigid segment in the middle of each transmission strip is curved rather than flat.

Rigid segments may also or alternatively be reinforced with a stiffer material such as metal, ceramic, carbon-fiber. Metal based reinforcement is shown in FIGS. 42A-42D. These reinforcements further improve the bending stiffness of the strip about the Y direction, and more importantly the twisting stiffness of the strip (between its first and second ends) about the Z direction. The reinforcement material (the metal squares in this case) may be attached via rivets as shown FIG. 42B or via screws, adhesives, or any other attachment method. A transmission strip that employs living hinges as the pivot joints may be formed from a thin strip of compliant material and selectively reinforced along its length. The sections of the strip that are not reinforced may serve as the living hinge. Material, thickness, length, and width of this non-reinforced section can be chosen to optimize its performance characteristics to provide the desired flexure strip level desired functionality in terms of stiffness, fatigue strength, aesthetics, maintaining shape (i.e. not collapsing) etc.

Figure 43A:
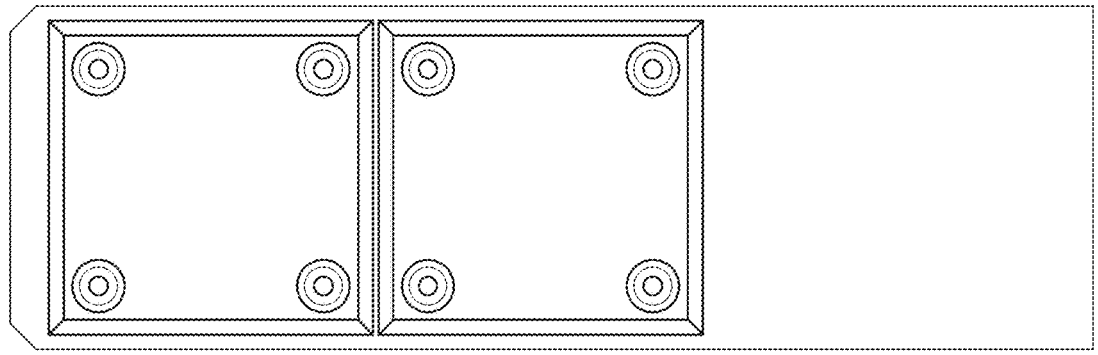
FIGS. 43A and 43B show top and side perspective views of another variation of a transmission strip formed of different materials.
Figure 43B:
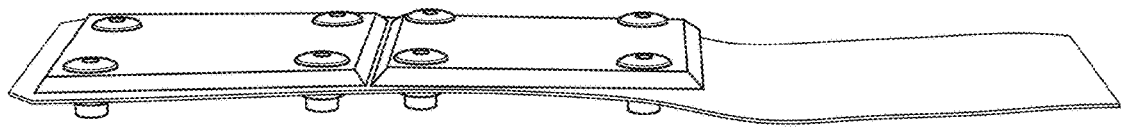
Figure 44A:
FIGS. 44A and 44B show top and side views of another variation of a transmission strip comprising a spring steel forming the hinge portion, which may be reinforced with additional materials.
Figure 44B:

For example, the thin sheet of compliant material may be nylon, Teflon, polypropylene, polyethylene, polyolefin, carbon fiber etc., or a woven fabric strip (which may be made of these materials). The reinforcement material to create the rigid sections may be made of any appropriate (e.g., stiff) material. For example, see FIGS. 43A and 43B, showing attachment of metal rigid sections to the compliant base material forming the living hinge. In some variations the thin sheet of compliant material forming the living hinge may be made of metal e.g. spring steel as shown in FIGS. 44A and 44B. Various materials may be used for reinforcement (not shown) to create the rigid sections. Alternatively, starting from a metal strip, the geometry could be progressively cut and stamped into a shape such that there are flanges and ribs on the rigid segments that provide rigidity while the metal strip is left as such at the living hinge locations to provide the desired compliance in bending, e.g., about the X direction.

Figure 45A:
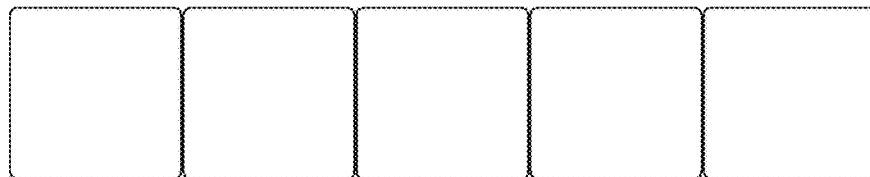
FIGS. 45A-45D illustrate another variation of a transmission strip.
Figure 45B:
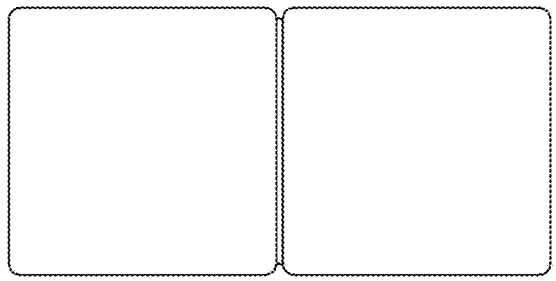
Figure 45C:
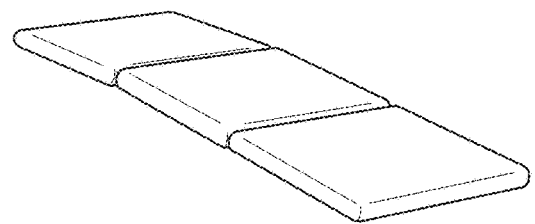
Figure 45D:
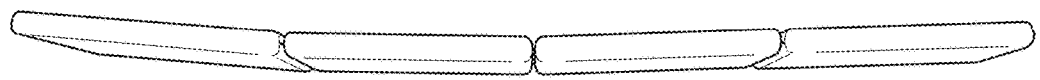
Figure 46:
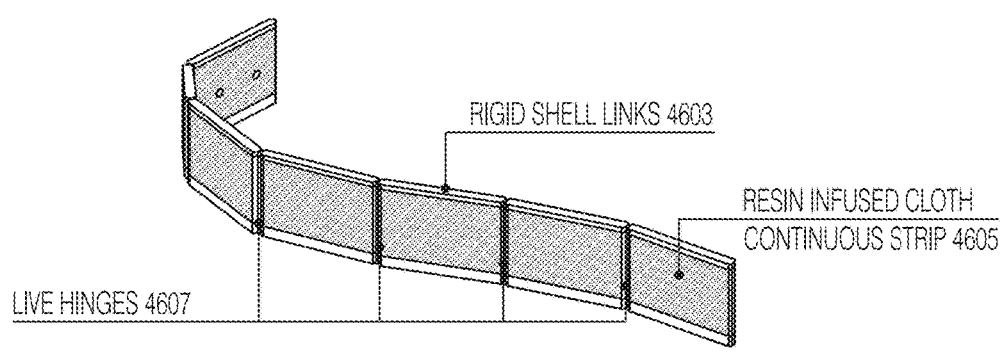
FIG. 46 illustrates another variation of a transmission strip.

FIGS. 45A-45D show another variation of a transmission strip having a living hinge. In FIG. 45A the transmission strip is composed of a continuous resin-infused cloth strip (e.g. made of nylon fiber) and repeating units of rigid segments (or shells or links) bonded to the cloth strip. This forms a series of living hinges with each hinge axis parallel with all other hinges within the strip permitting the strip to be flexible only about the X direction. Multiple rigid links 4603 are first made or printed. A resin infused strip 4605 is inserted into the rigid link shell. Successive links are kept separated by the appropriate distance to yield the desire living hinge 4607 dimensions. Epoxy is then used to attach the cloth strip to the rigid link shells, and the assembly is allowed to set. The construction where a woven fabric strip is used as the compliant element can produce a transmission strip that has the desired low stiffness in bending about the X direction, desired high stiffness in bending about the Y direction. Depending on the dimensions and construction, twisting stiffness about the Z direction may or may not be high.

In addition to the variations described above, other transmission strip embodiments may also be used. For example plastic or metallic watch straps/bands may provide the desired transmission strip functionality, having an alternating sequence of the rigid segments and pin based pivot joints. Rubber/plastic timing belts may also be used, having an alternating sequence of relatively rigid segments (thick)

and living hinge (thin) based pivot joints. Machine/bicycle chains having an alternating sequence of rigid segments and pin-based pivot joints may also be used. Flexible tracks may also have an alternating sequence of the rigid segments and pin based pivot joints, and may also be used.

Figure 53:
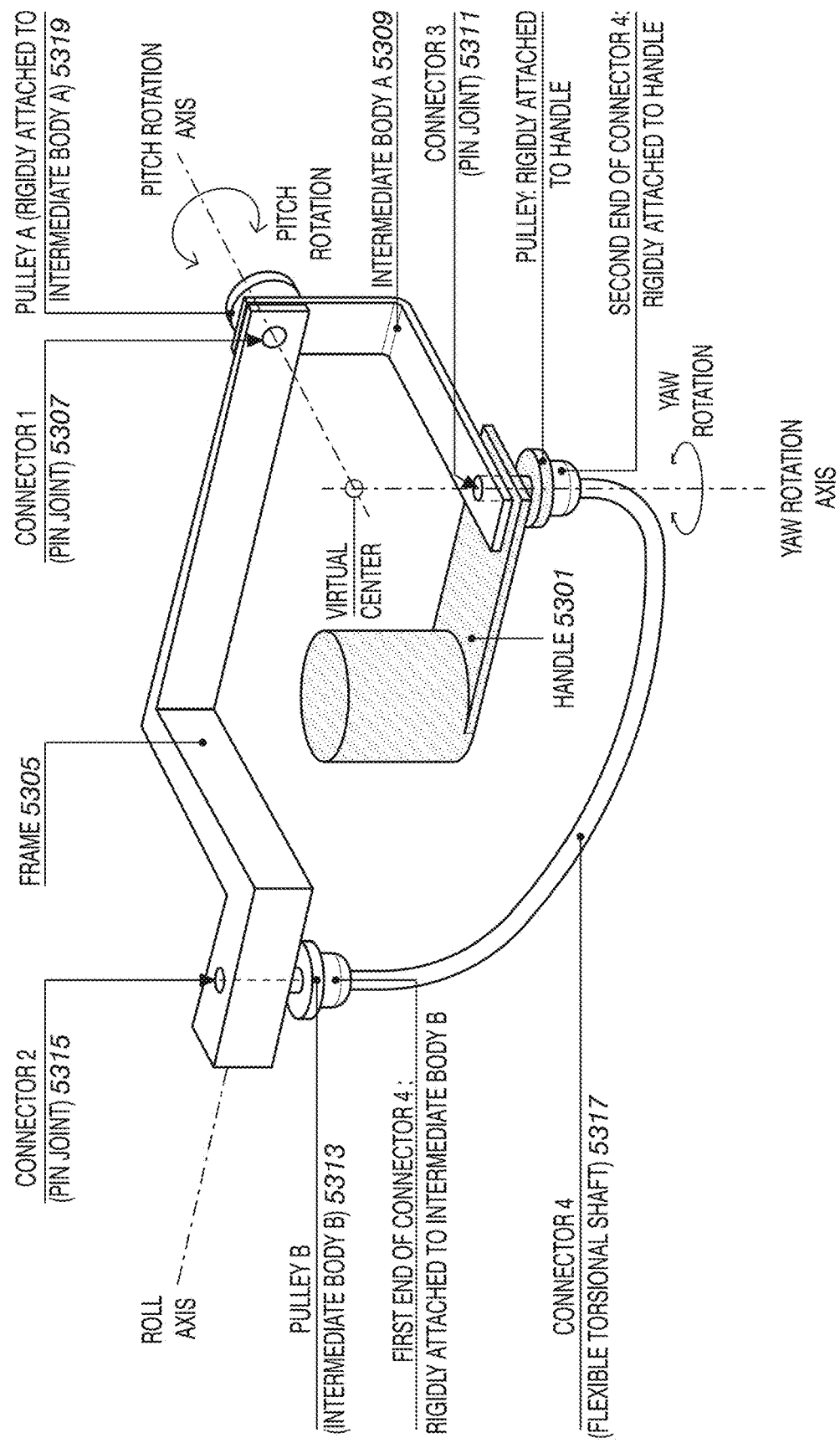
FIG. 53 is a schematic illustration of another variation of a parallel kinematic mechanism.

FIG. 53 illustrates another variation of a PK mechanism that follows the constraint map of FIG. 26 and also provides a virtual center of rotation. In this variation, between the handle 5301 and the frame 5305, there are two parallel (or independent) mechanical connection paths. As a result of this construction, the mechanism provides two rotational degrees of freedom of the handle with respect to the frame. These two rotations are marked as "Pitch rotation" (rotation 1 of FIG. 26) and "yaw rotation" (rotation 2 of FIG. 26). One path of connection between the frame and the handle (the upper path shown in the constraint map of FIG. 26) connects the frame 5305 to intermediate body A 5309 via connector 1 5307, which is a pin/pivot joint. This joint allows relative pitch rotation between frame and intermediate body A 5309, but constrains (and therefore transmits) yaw rotation between the two. Intermediate body A 5309 is connected to the handle 5301 via connector 3 5311, which is another pin/pivot joint. This joint allows relative yaw rotation between intermediate body A 5309 and the handle 5301, but constrains (and therefore transmits) pitch rotation between the two. The second path of connection between the frame 5305 and the handle 5301 (corresponding to the lower path shown in the constraint map of FIG. 26) corresponds to the connection from the frame 5305 to intermediate body B 5313 via connector 2 5315, which is a pin/pivot joint. This joint allows relative yaw rotation between frame 5305 and intermediate body B 5313, but constrains (and therefore transmits) pitch rotation between the two. Intermediate body B 5313 is connected to the handle 5301 via connector 4 5317. Connector 4 (5317) is a kind of joint or connection, commonly referred to as a flexible torsion shaft or simply flexible shaft. This flexible shaft has two ends. The first end is rigidly attached to intermediate body B 5313 and the second end is rigidly attached to the handle. Between these two ends is a flexible shaft segment that allows certain motions and constrains other motions. This connector constrains rotation about its torsional axis which is the same as yaw rotation axis at its second end; therefore, this connector transmits yaw rotation from handle to intermediate body B. At the same time flexible shaft connector is compliant in pitch direction, or allows pitch rotation between its two ends.

As a result of this construction, any arbitrary combination of pitch and yaw motion at the handle with respect to the frame gets mechanically separated into a pitch only rotation available at pulley A 5319 which is rigidly attached to intermediate body A (note that because of this rigid attachment, pulley A 5319 and intermediate body A 5309 are the same rigid body) and a yaw only rotation at pulley B 5313 which is rigidly attached to intermediate body B (note that because of this rigid attachment, pulley B 5313 and intermediate body B are the same rigid body). Thus, pulley A exhibits a pure pitch rotation with respect to the frame and pulley B exhibits a pure yaw rotation with respect to the frame. Since the axes of rotation of these two pulleys is fixed with respect to the frame, it is practically easy to transmit these two rotations via a mechanical transmission system/method that also employs the frame as a ground reference to another remote or distal location on the frame.

The above example illustrates a serial kinematic design that has been augmented by adding an independent, non-overlapping connection path (using a flexible torsion shaft and an additional pulley B) resulting in a parallel kinematic design. The flexible torsion shaft transmits rotations about its axis while remaining compliant in bending of its axis. Here, with just the frame, intermediate body A, and handle, we would have a serial kinematic mechanism with two rotational DoF (pitch and yaw rotations) mechanism that provides a virtual center of rotation, but would have all the challenges related to transmission associated with serial kinematic mechanisms described earlier. In this example, intermediate body A is rigid in translation along the third axis (roll, not shown in FIG. 53) and the connectors 1 and 3 also do not allow this translation. Even though the other mechanical path comprising connector 4 (the flexible shaft) does allow this translation, both paths have to allow this translation motion (or DoF) for the overall mechanism to also allow this translation motion (or DoF). Therefore, translation along the roll axis between the handle and the frame is constrained (i.e. is not a DoF, i.e. is not allowed) in this particular embodiment.

Intermediate body A is rigid in rotation about the third axis (roll, shown in FIG. 53) as well as the connectors 1 and 3 are also rigid about this rotation (or in other words constrain/transmit this roll rotation. Here the other mechanical path comprising connector 4 (the flexible shaft) does allow this roll rotation, but it takes only one path (in the overall mechanism) to constrain relative motion. Since the first path constrains roll rotation between the handle and the frame, this roll rotation is constrained in the overall mechanism as well. In other words, roll rotation is transmitted from the handle to frame and vice versa by this PK mechanism.

Figure 54:
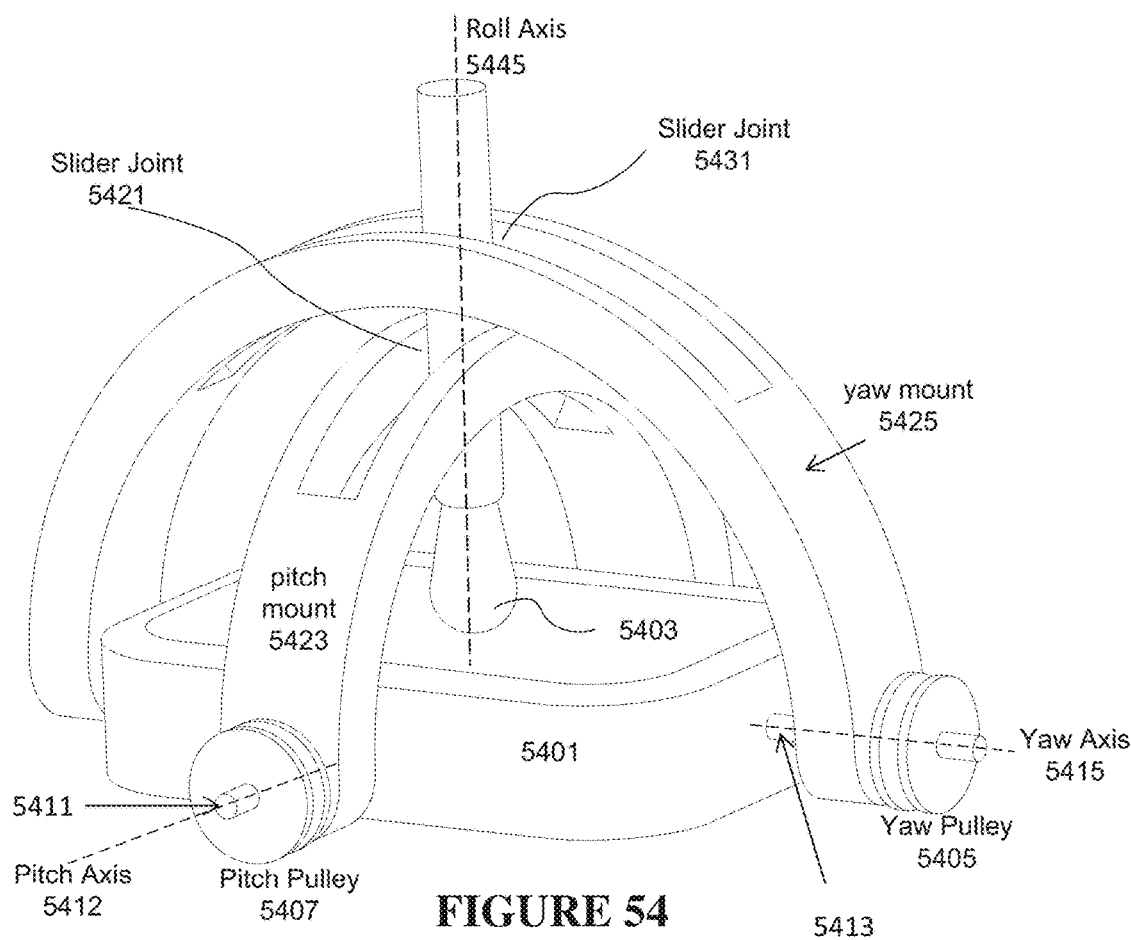
FIG. 54 is a schematic illustration of another variation of a parallel kinematic mechanism.

FIG. 54 illustrates another example of a parallel kinematic system configured according to the constraint map of FIG. 26. In this example, the first rotation (rotation 1) corresponds to the pitch rotation, the second rotation (rotation 2) corresponds to yaw. The frame 5401 and handle 5403 may be similar to those described above. The intermediate body A 5407 is a Pitch pulley and Pitch mount (the two are rigidly coupled together) and the intermediate body B 5405 are a yaw pulley and yaw mount (the two are rigidly coupled together). Connector 1 5411 corresponds to a pivot joint between Pitch pulley and frame about Pitch axis 5412, while connector 2 5413 corresponds to a pivot joint between yaw pulley and frame about yaw axis 5415. Connector 3 5421 is a slider joint 5421 between pitch mount 5423 and handle 5403 and connector 4 5431 is a Slider joint 5431 between yaw mount 5425 and handle 5403. Although shown to be in the shape of a semi-ring or arch in FIG. 54, the pitch mount and yaw mount can be any generic shape. Semi-circular shapes, as shown, may help avoid interferences between the pitch mount and yaw mount while both rotate about their respective rotation axes with respect to the frame. This embodiment may provide a virtual center (VC) of rotation of the handle 5403 with respect to the frame 5401. This virtual center of rotation is defined by the intersection of the pitch and yaw axes, as described above.

In operation, the parallel kinematic mechanism shown in FIG. 54 may be operated by a user grasping and manipulating the handle 5403. The parallel kinematic mechanism separates and filters out rotation of the handle 5403 relative to the frame 5401 into yaw and pitch components only at the yaw pulley and pitch pulley, respectively. The yaw component of rotation of the handle with respect to the frame is transmitted to the yaw mount 5425 (e.g., yaw ring) via the slider joint 5431, which transmits yaw rotation but allows (or filters out) the pitch rotation. This causes the yaw mount 5425 and yaw pulley 5405 to rotate about connector 2 (pivot joint 5413) with respect to the frame 5401. Thus, the yaw pulley 5405, which rotates about yaw axis 5415, only exhibits the yaw component of rotation of the handle relative to the frame. The pitch component of rotation of the handle with respect to the frame is transmitted to the pitch mount 5423 via the slider joint 5421, which transmits pitch rotation but allows (or filters out) the yaw rotation. This causes the pitch mount 5423 and pitch pulley 5407 to rotate about connector 1 (pivot joint 5411) with respect to the frame 5401. Thus, the pitch pulley 5407, which rotates about pitch axis 5412, only exhibits the pitch component of rotation of the handle relative to the frame. In the end, the combined yaw and pitch rotations of the handle 5403 may be separated into a pure yaw rotation about the yaw axis at the yaw pulley 5405 and a pure pitch rotation about the pitch axis at pitch pulley 5407.

When used as the input joint/interface of an instrument/tool/device/machine, the rotations of the pitch and yaw pulleys 5407, 5405 about the respective pitch and yaw axes 5412, 5415 may be used to transmit the desired pitch and yaw rotations mechanically to a remote end effector, or electronically to a computer input device. Compared to a serial kinematic mechanism, in the case of this parallel kinematic mechanism the two axes of rotations 5412 and 5415 are fixed with respect to the frame. Therefore, rotations about these axes can be transmitted via various mechanical transmission methods/systems that are practically simple and feasible. These various transmission methods/systems all operate with respect to the same ground reference frame 5401. Thus, any moving components of this transmission system, all have an axis of rotation or translation or a trajectory of motion that is fixed with respect to this ground reference frame. That makes the task of designing and implementing a transmission system from each individual axis 5412 or 5415 to some other location on the frame (or an extension of the frame) practically feasible.

In one instance, the rotations produced at the pitch and yaw axis pulleys 5407, 5405 may be individually transmitted to a remote end effector using pitch and yaw transmission cables, respectively. This design greatly facilitates the capturing and transmission of 2-DoF rotational motion of a handle with respect to a frame; doing so directly from the handle is difficult; instead this design separates out the 2-DoF rotation into two 1-DoF rotations; these two rotations may be individually and independently transmitted relatively easily (using cables, or gears, or links, or electronically, or pneumatically) because they are now well-defined rotations about pitch and yaw rotation axes that are fixed with respect to the frame.

In the example shown in FIG. 54, the handle 5403 may be freely rotated about the roll axis 5445 with respect to the frame 5401. Thus, roll rotation may not be transmitted from handle to frame and vice versa by this variation.

Figure 55:
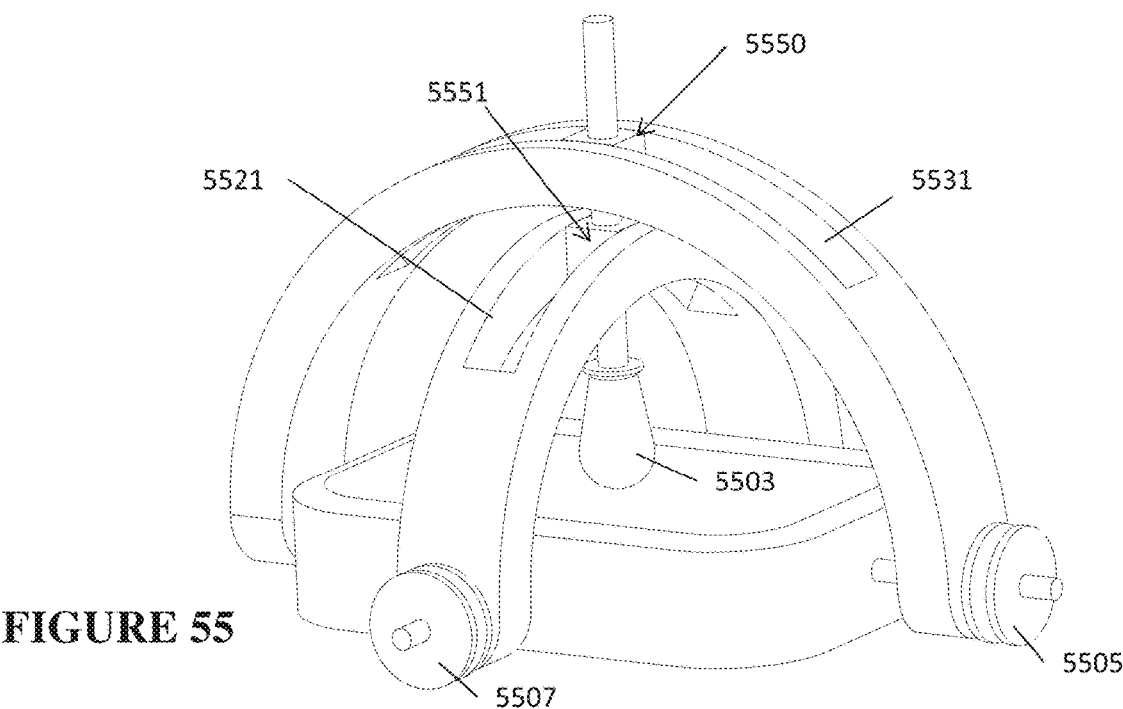
FIG. 55 schematically illustrates another variation of the parallel kinematic mechanism shown in FIG. 54.

FIG. 55 shows another variation of the embodiment shown in FIG. 54, in which the handle 5503 has a geometry (note the square pegs 5550, 5551 that are rigidly attached to the handle) such that roll rotation is transmitted from the handle 5503 to intermediate body A 5507 and vice versa via the slider joint 5521 between the two; and from the handle 5503 to intermediate body B 5505 and vice versa via the slider joint 5531 between the two. In practice, there may be either square peg 5550, or square peg 5551, or both rigidly attached to the handle. This variation is otherwise similar to the variation shown in FIG. 54, and may operate in the same manner. However, because of either or both of the square pegs 5550, 5551, this variation constrains and therefore transmits roll rotation of the handle 5503 relative to the frame 5401, and vice versa, about a roll axis of rotation.

Although in some of the variations described above, the terms VC mechanism, input mechanism, input joint, and PK mechanisms may be used interchangeably, e.g., when used in remote/minimal access instruments, however, this is not necessarily always the case. In general, a VC mechanism need not be PK in design, and not every PK mechanism (and more specifically any PK mechanism based on the constraint map of FIG. 26) has to provide a VC. Also not every PK or VC mechanism needs to serve as the input joint. As indicated above, in FIGS. 29A-29C, the mechanism may serve as the output joint/interface in a certain tools, machines, devices or instruments. The constraint map of FIG. 26 enables separation of a 2DoF rotation into two individual single DoF rotations about axes that are fixed with respect to the frame, and conversely enables the combination of two individual single DoF rotations about axes that are fixed with respect to the frame, into a single 2DoF rotation of a handle with respect to the frame. This functionality is a consequence of the constraint map and holds irrespective of the VC functionality. For certain physical embodiments of the constraint map of FIG. 26, the mechanism may also include a virtual center as shown in many variations above.

Figure 56A:
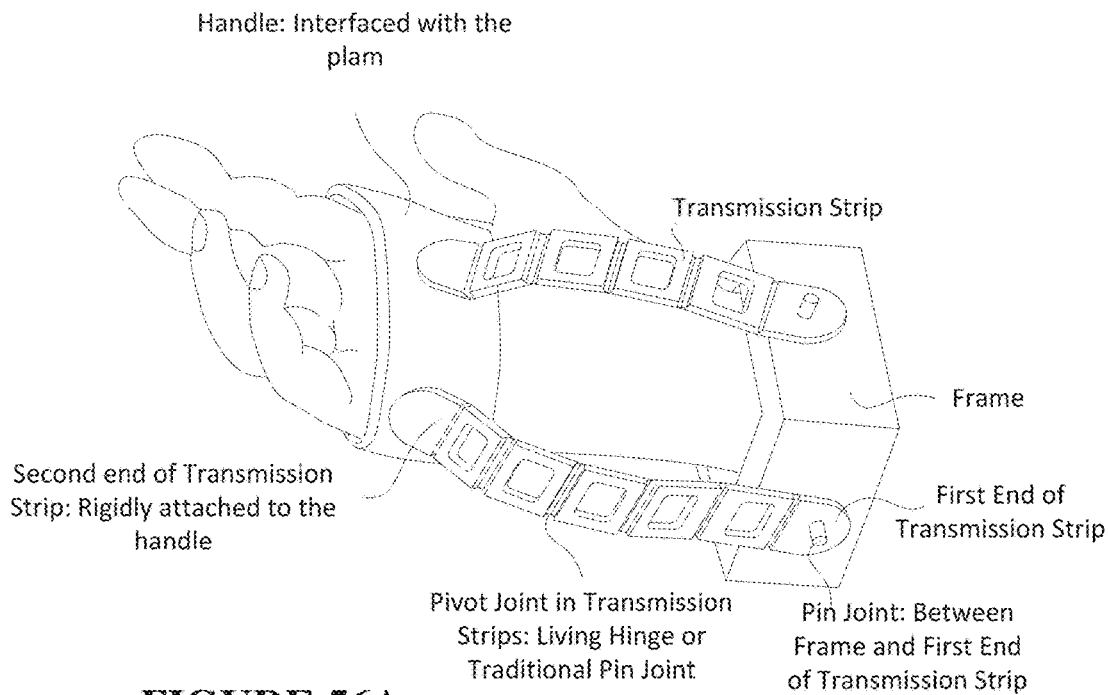
FIGS. 56A-56C illustrate variations of a parallel kinematic mechanism configured for interfacing over a user's hand.
Figure 56B:
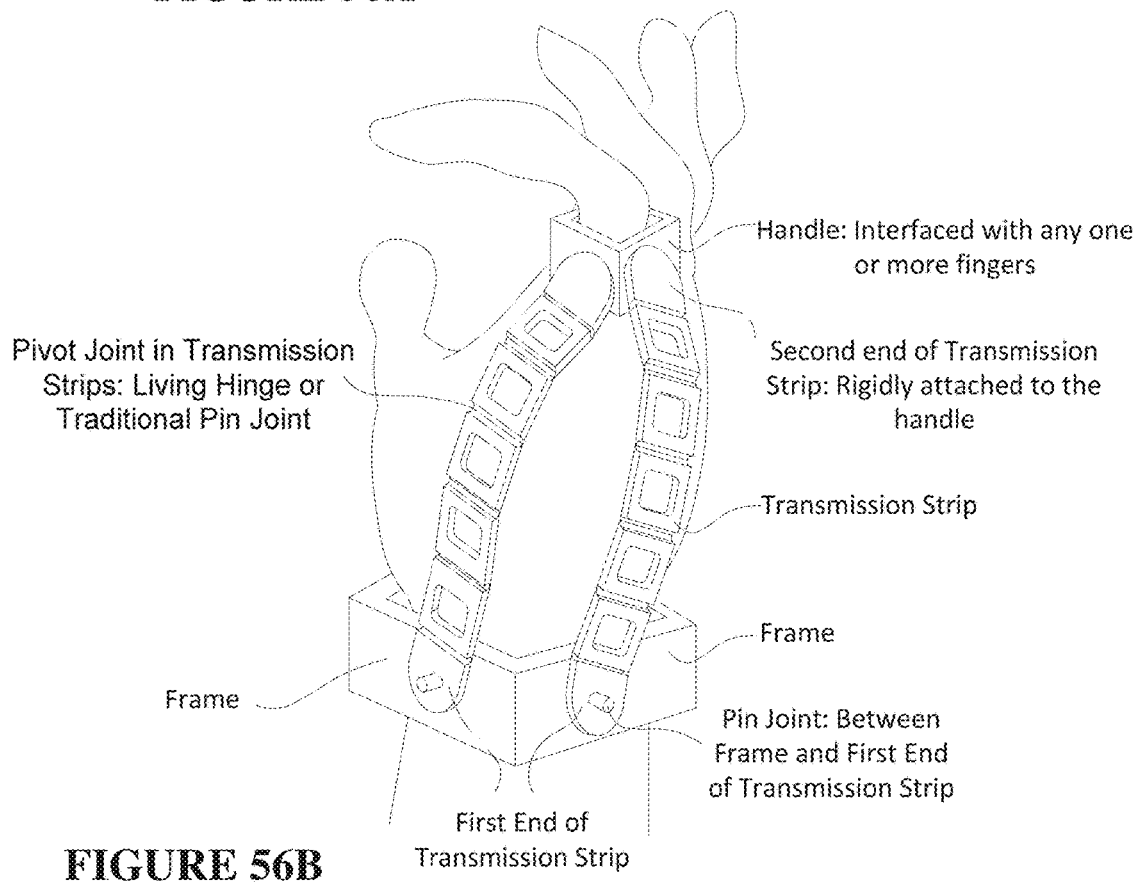
Figure 56C:
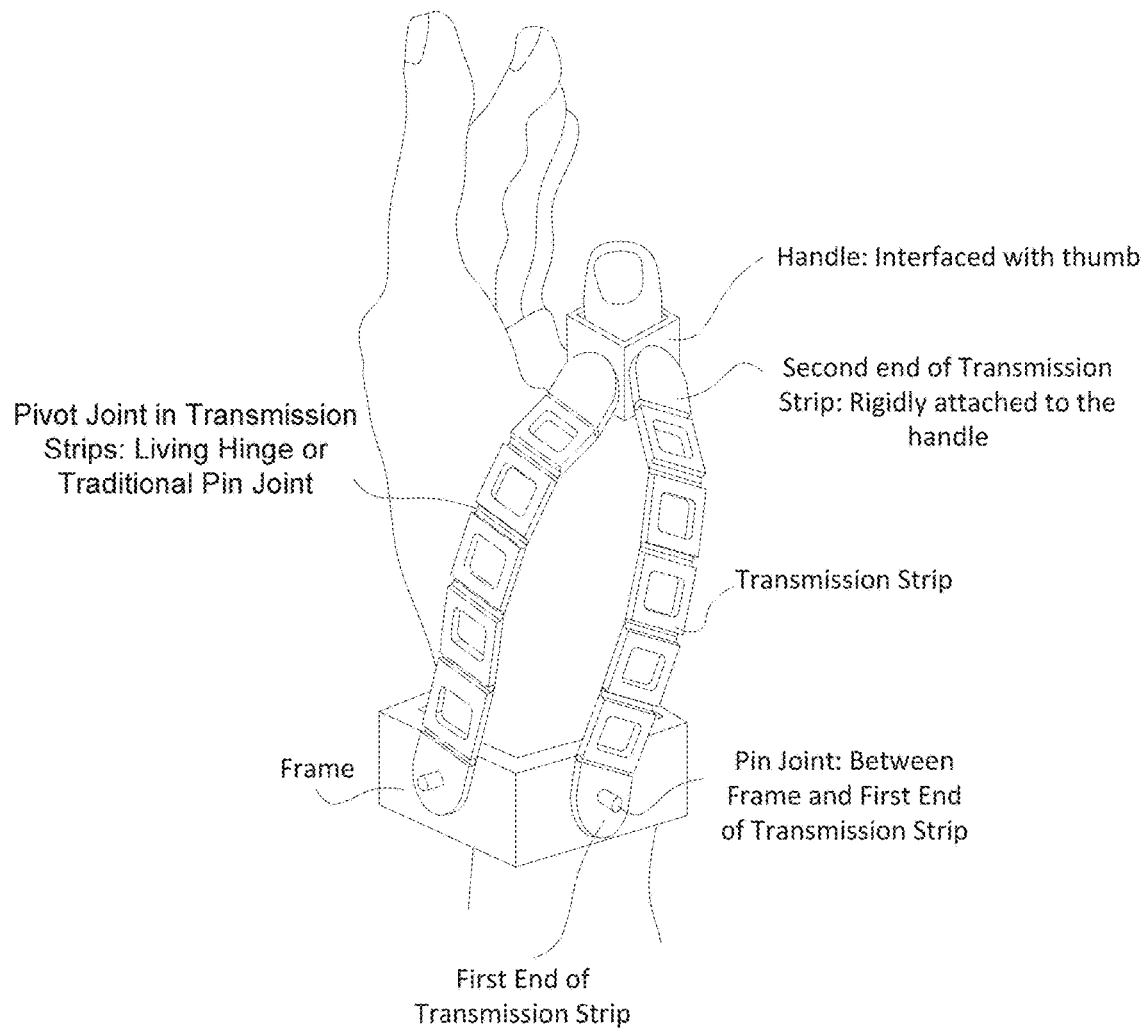

In variations of the PK mechanism apparatuses described above having a virtual center, it may be beneficial to locate the virtual center provided by the PK mechanism close to the center of an articulating human joint (e.g. wrist, finger base joint i.e. the metacarpophalangeal joint (MCP), ankle, shoulder, hip, etc.). When interfaced with a human joint, the mechanism may be used as an input interface or output interface of a tool/machine/device, as shown above. For example, the handle could interface with a hand or a foot in one of various different ways, and similarly the frame may interface with another part of the human body also in many different ways. In the case when the PK mechanisms described above are used in conjunction with a human wrist joint, the handle can interface the user at various locations on the hand and in various ways as shown in FIGS. 29A-29C and in FIGS. 56A-56C. In FIGS. 56A-56C, the virtual center of the mechanism may be kept close to the center of rotation of the human wrist. Such proximity can help in some applications e.g., by allowing natural and free rotation of the human wrist without the mechanism restricting the wrist's natural range of motion, but this need not be a strict requirement. Furthermore, the frame may be securely attached the forearm of the user, or may be lightly attached via padding material/sponges etc., or may be coupled to the forearm via a jointed interface, or may not be attached at all.

In any of the examples shown, the two rotational axes of the user's articulating joint (e.g. wrist) need not be exactly the same or analogous as the two rotational axes of the parallel kinematic mechanism/joint. For example consider FIG. 29B, in which the two rotations of the ankle joint may be anatomically defined about the axes A and B, while the two rotational axes of the PK mechanism may be given by C and D. Note that the two sets may be, but are not necessarily the same.

In general, the two rotational axes of the PK mechanism and the two rotational axes of the user joint approximately lie in the same plane. For example, in FIG. 29B, it may be seen that axes A, B, C, and D are in the same plane. As long as this condition is met, the actual configuration of the PK mechanism (and its associated rotational axes) may be arbitrary with respect to the user articulation joint (and its associated rotation axes). This provides freedom in realizing the details of the PK mechanism geometry and construction in a manner that takes into account practical space constraints around the user's articulating joint.

As discussed above, the frame may interface with an appropriate part of the human body. For example, if the handle may interface with a hand, as shown in FIG. 56A, and the frame may interface with the forearm. If the handle interfaces with the foot (FIGS. 29A and 29B), the frame may interface with the shin/calf. If the handle interfaces with the arm (FIG. 29C), the frame may interface with the shoulder. The frame interface may be a secure attachment, or light attachment via padding material/sponges, or a jointed attachment, etc.

As mentioned above any of the parallel kinematic mechanisms described herein may be used in combination with any appropriate output. For example, an input joint of any of these parallel kinematic mechanisms may be coupled to an output joint for controlling an end effector. FIG. 14A shows one example of an output joint 32 is configured as a flexible, snake-like joint. In this example, the output comprises flexible disks 82 attached in a fashion such that the direction of flexure of each element alternates. This joint 32 can be actuated by pushing or pulling on the disks 82, causing expansion and contraction of its sides. Cables (not shown) running through each disk 82 of the output joint 32 may be selectively pulled to create deflection in the yaw and pitch rotation directions or any combination thereof. Alternative joint types that could be used include, but are not limited to, inextensible wires compliant in bending, hourglass flexure, compression/extension springs with constrained torsion, or any other 2-DoF (yaw and pitch) joints. The output joint 32 may be temporarily locked in any desired orientation with respect to the tool shaft 22.

Instead of being a traditional 2-DoF joint, the output joint 32 may also be realized by means of a VC mechanism such as the one illustrated in FIG. 14B, similar to the one used at the input joint 16 described above. Barring space constraints, such a VC mechanism at the output joint 32 may provide a center-of-rotation for the end effector 12 that can be conveniently located at any location other than the physical location of the output joint 32.

Any of the parallel kinematic mechanisms described herein may also allow or include additional controls for actuating an end effector. For example, any of these apparatuses may include one or more controls for actuating the open/close motion of jaws on an end effector. In some variations, an end effector may be made to grasp via transmission of an actuation from the handle of the apparatus (e.g., by pushing or pulling a button, trigger, lever etc.). Transmission of this control may be combined with the transmission system for the rotational motions (e.g. pitch and yaw) discussed herein, or it may be separate. Furthermore, a mechanical, electrical, pneumatic, or any other transmission system may be used for this control. In one example, a mechanical cable or cables may pass from the handle 24 to the end effector 12 for transmitting this control. For example, in one variation, shown in FIG. 15, an apparatus 84 may include a control (lever 81) that may form part of or may be mounted on the handle 24 and may be mechanically coupled to the end effector 12 for actuating a grasping motion (open/close) of jaws on the end effector 12. For example, a cable 86 may be attached to the lever 81 and an associated closure mechanism 84 provided, wherein the cable 86 may transmit the grasping motion from the lever 81 and the closure mechanism 84 to jaws (e.g. 96 in FIG. 16) on the end effector 12. The grasping transmission system transmits one grasping DoF from the user's thumb/fingers to a corresponding open/close action (also one DoF) at the end effector 12. In general, the closure mechanism 84 may have more than one DoF that may be transmitted to the same number of DoF at jaws on the end-effector 12. Since the handle 24 will move along with the user's hand, thumb and fingers during wrist motion, providing the lever 84 and the closure mechanism 84 on the handle 24 ensures that the input device for providing the grasping motion does not move relative to the hand, thumb, and fingers.

In the example shown in FIG. 15, as the user's thumb presses the lever 81 of the closure mechanism (handle lever sub-assembly) 84 it rotates approximately about axis (a). A flexure element 90, such as a piece of spring steel, may be used as a one-DoF pivot joint, wherein this joint may be compliant in nature so as to automatically return to its nominal (undeformed) position. Alternatively, this may be a traditional pivot joint comprising a pin and a separate return spring (leaf spring or coil spring) can provide the returning to nominal function. This automatic return is desirable to ease the motion input requirements for the user's thumb or fingers. It is understood that any one-DoF joint could be used for this actuation, for example, a pin, slider, or push button (compliant or spring-mounted), provided one end is mounted to the handle 24 and the other is acted on by the fingers or thumb. Using thumb actuation allows the user to grasp the handle 24 with their fingers and palm while independently actuating the lever 81. A finger-actuated lever could alternatively be used, depending on size constraints from the shape of the handle 24.

According to one non-limiting aspect of the present invention, the closure mechanism 84 may include a ratcheting mechanism which allows the user to lock the lever 81 in different positions. This device may also use a compliant one DoF flexure joint 92 as shown in FIG. 15. The ratcheting mechanism is similar to those seen in U.S. Pat. Nos. 5,209, 747 and 4,950,273, incorporated by reference herein, and may comprise a toothed body 94 that engages a single tooth on the lever 81 in different positions. As the user depresses the lever 81 of the handle lever sub-assembly 84, the toothed body 94 deflects about axis (b) and allows the lever 81 to slip down to the next tooth. When the user releases the lever 81, it remains at whatever current position it is in. To release the lever 81, the toothed body 94 is simply deflected forward by the user's thumb causing the ratchet teeth to disengage. The springiness of the flexure joint 92 holding the lever 81 causes the lever 81 to go back to its nominal condition. In general, any other variable closure mechanism may be used instead of the ratcheting mechanism, depending on the specifics of the application. Such a mechanism provides the user the ability to hold a grasp (for example, on a tissue) inside the patient's body via the jaws 96 of the end effector 12. Alternatively, one can also envision a latching mechanism 84 where the level 81 is depressed until it latches and locks in a closed position. Further depressing this lever would that unlatch or unlock the lever allowing it to return to its nominal position under the action of above mentioned return spring.

During operation, the handle 24 moves along with the user's hand and wrist, such that the distance between the user input (i.e. handle) and the tool output (i.e. tool frame, tool shaft, end effector, etc.) is variable. Because each user input motion should be independent for the desired tool functionality, a transmission means that allows for a variable distance and orientation between components, particularly the tool handle and tool frame, is generally desirable. In FIG. 15, relative motion between the cable 86 and a sheath or cable housing (not shown) may be used for actuation. The cable 86 may attach to the end effector 12, pass through the tool shaft 22, pass through the sheath to the floating plate 26 of the VC mechanism 16, pass through the handle 24, and then attach to the lever 84. The sheath or cable housing may be connected between the tool frame 18 and the plate 26 (or equivalently handle 24). Between the tool frame 18 and the plate 26, there may be slack in the sheath to ensure that the motion of the plate 26/handle 24 (e.g. pitch and yaw rotations with respect to the frame) is not constrained by the sheath. When the floating plate 26 moves in response to user wrist actuation, the amount of slack in the sheath will change but there will be no relative motion between the cable 86 and the sheath. This arrangement is similar to that of a brake cable and associated sheath on a bicycle.

The sheath through which the transmission cable 86 runs between the tool frame 18 and floating plate 26 can be any type of hollow body that is flexible in bending. According to one non-limiting aspect of the present invention, the sheath may include a flexible coiled spring or nylon tubing that provides enough flexibility in bending, but has a high stiffness under compression. Another example of this sheath would be a Bowden cable sheath. This stiffness ensures that the relative motion between the cable 86 and the sheath dominate during tension in the transmission cable 86. When the cable 86 is pulled through the sheath, the cable 86 acts the same regardless of the shape of the sheath. With slack introduced in the sheath, the cable 86 can be straightened or bent or deformed by a certain amount, without the grasping actuation force in the cable 86 being affected. This cable and sheath system may be implemented in various ways, but ultimately should allow for a variable distance between the tool frame 18 and the floating plate 26 of the VC mechanism 16. It should be noted that such a cable and sheath arrangement may be used not only for the grasping action transmission, but also for the transmission of the wrist rotations from the input joint 16 to the output joint 32. For example, separate sheaths could be employed for two pitch transmission cables, two yaw cables, and one or two grasping actuation cable.

Figure 16:
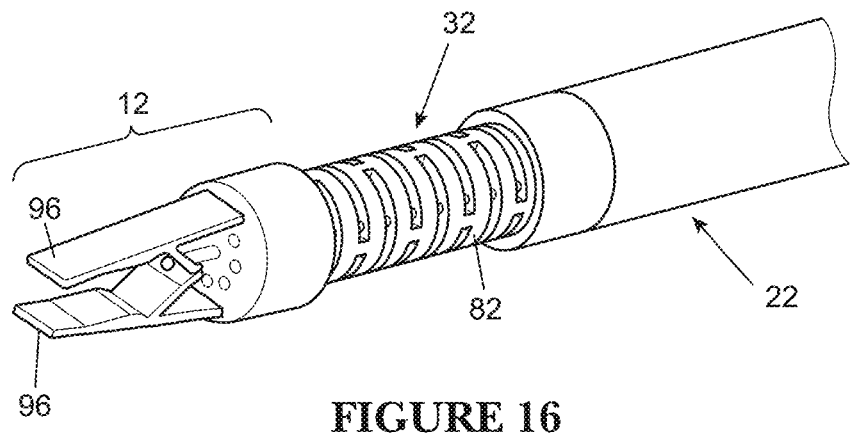
FIG. 16 is a perspective view of an end effector according to the present invention.

As described above, the end effector 12 may reproduce the user's actions in vivo. The end effector 12 can be any number of one DoF devices, such as scissors, shears, needle drivers, dissectors, graspers, or retractors. These end effectors 12 may be compliant or rigid, and may have active and passive components (depending on the motion transmission system). With reference to FIG. 16, the embodiment shown includes a compliant grasping mechanism that is at equilibrium in the open (or grasp-release) position. When the center of this grasper is pulled axially backwards, the jaws 96 of the end effector 12 close inward. In addition to grasping, the jaws 96 may have other functionality such as, but not limited to, cutting or cauterizing of tissue.

Figure 17:
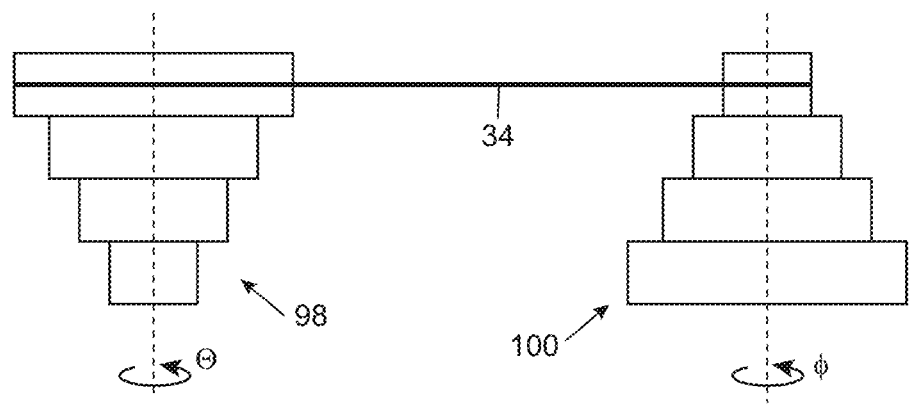
FIG. 17 is a schematic illustration of input and output pulleys allowing for a variable transmission ratio according to the present invention.
Figure 18:
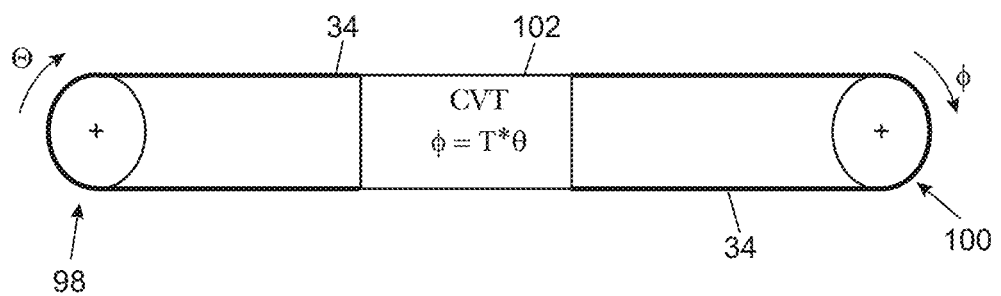
FIG. 18 is a schematic illustration of input and output pulleys allowing for a continuously variable transmission according to the present invention.

With reference now to FIG. 17, transmission between the input joint 16 and the output joint 32 may be accomplished via a pulley and cable system for each of the two rotational DoF, pitch and yaw, as described with respect to several embodiments above. The design may incorporate a mechanism to scale the user's input rotation (θ) reflected at an input pulley 98 (corresponding to either of the pulleys 78 or 80 in FIGS. 12 and 13) to the tool output joint rotation (Φ) at an output pulley 100 by some transmission ratio T, thereby providing a variable transmission ratio between the tool input (user's hand rotation about his/her wrist) and tool output (end effector 12 rotation about the output joint 32). This transmission ratio T may be fixed, may be changed in discrete steps, or may be changed continuously. Any fixed transmission ratio may be achieved by choosing appropriate radii for the input and output pulleys 98, 100. Alternatively, instead of input and output pulleys, one may have other components such as gears, linkages, levers, etc. and a variable transmission ratio between the input pitch and yaw rotations and corresponding pitch and yaw rotations is still relevant. A discretely variable transmission ratio may be accomplished by means of a stepped configuration of the input and output pulleys 98, 100 such as that shown in FIG. 17, and a shifting mechanism (not shown) that allows a user to change between ratios. This shifting mechanism may be similar to the shifting mechanism for variable gears on a bicycle. Alternatively, a continuously variable transmission (CVT) may be employed which allows the user to select an arbitrary ratio between input and output rotations, as shown in FIG. 18. Such a CVT may be implemented by an intermediate module 102 such as, but not limited to, a V-Belt or toroidal arrangement, wherein a generic CVT arrangement is shown in FIG. 18. Although the CVT embodiment is illustrated in an arrangement that utilizes input and output pulleys 98, 100, it is understood that pulleys 98, 100 are not required for the implementation of a CVT in accordance with the present invention.

Figure 19:
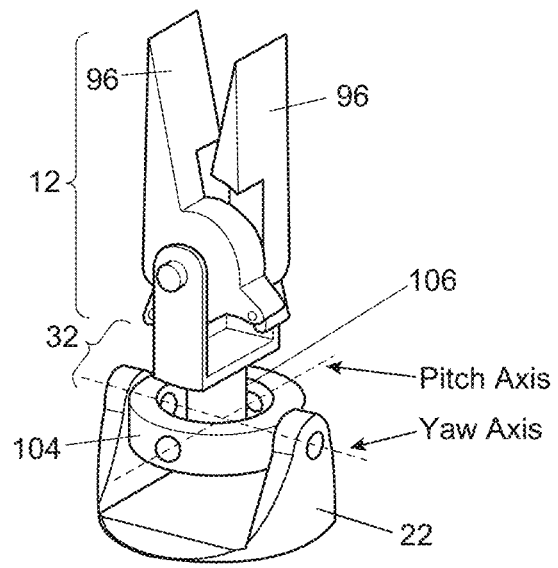
FIG. 19 is a perspective view of a tool tip manipulator and output joint according to the present invention that decouples the actuation of the two wrist DoF.

Turning next to FIG. 19, a tool 10 according to the present invention may incorporate an end effector 12 and output joint 32 that decouple the actuation of the pitch and yaw DoF at the tool output. As described above, the tool output comprises an end effector 12 and a 2-DoF rotational output joint 32 about which the end effector 12 can rotate. The actuation of three motions (two wrist-like rotations of the end effector 12 about the output joint 32, and one open/close motion of the end effector jaws 96) are decoupled in this embodiment. These three motions are actuated at the input joint 16 by means of the user's hand rotation about his/her wrist, accomplished naturally via the VC mechanism 16, and an end effector actuation mechanism (e.g., such as the closure mechanism 84 shown in FIG. 15 or any other end effector) provided at the tool input, respectively.

Pin-based joints can achieve large rotations in very small spaces, but their mechanical implementation can result in the coupling of rotations in cascaded arrangements. In such prior art configurations, the pitch rotation of the tool is implemented after the yaw rotation and, as a result, the transmission cable actuation to produce a desired pitch depends on the current yaw angle. This is referred to as end effector motion coupling and results in non-intuitive tool output behavior. In the embodiment of the present invention depicted in FIG. 19, the output joint 32 includes a pair of nested rings 104, 106. The outer ring 104 may be connected by a pin joint to the tool shaft 22, and is actuated by a pair of cables (not shown) which may be attached to the outer ring 104 generally at the location of the pitch axis and which produce a rotation about the yaw axis. The inner ring 106 is pinned to the outer ring 104 so that the pitch axis is orthogonal to the yaw axis. The inner ring 106 is also driven by a pair of drive cables (not shown) which may be attached to the inner ring 106 at generally the same height as the outer ring 104 and generally at the location of the yaw axis. The two joints create a center of rotation acting at the intersection of the pitch and yaw axes. This arrangement prevents motion coupling by co-locating the two joint axes in an arrangement that would not be feasible with traditional cascaded, pin-based joints. This end effector 12 and output joint 32 design allows the tool 10 according to the present invention to be operated with a smaller radius of curvature, thus providing a tighter workspace which is desirable for the surgeon (user). This output joint 32 also fully separates the pitch and yaw motions to allow for completely independent motions, thus keeping the rotations mechanically decoupled.

Figure 20:
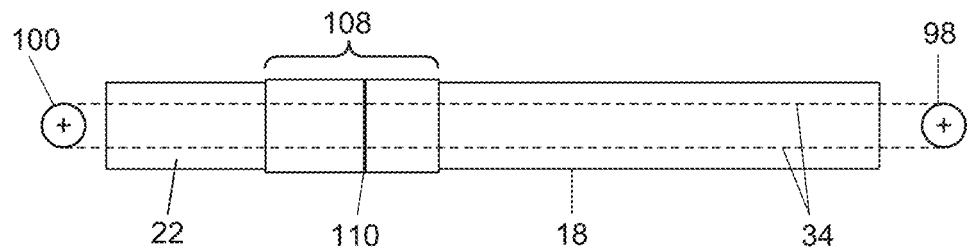
FIG. 20 is a schematic illustration of an embodiment of a minimal access tool according to the present invention which includes a quick release mechanism for replacing the tool shaft.

With reference to FIG. 20, the tool shaft 22 may be easily replaceable while the frame 18 remains attached to the user's arm. This feature allows the user to quickly replace the tool shaft 22 and end effector 12 without having to remove the entire tool 10 from his or her arm. A cable junction 108 may be provided at the connection point between the tool shaft 22 and the frame 18. Alternatively, a junction 108 may be introduced at the base of the tool frame 18, such that one part of the frame 18 that supports to the tool input remains attached to the user's forearm via the arm attachment member 20, while the rest of the frame 18 along with the tool shaft 22 is replaceable. In either of these two cases, to release and reconnect the tool shaft 22 from/to the frame 18, transmission cable connections must be severed and reconnected while maintaining sufficient cable tension to allow effective input-output motion transmission. These links could be established by a quick release mechanism 110 such as, but not limited to, a snap-fitting mechanism, magnetic coupling, or some other method of temporarily joining and releasing two tensile members. This link can be severed and reattached as desired during a surgery to allow the user to switch tool shafts 22 without having to change or remove the arm attachment member 20.

The tool 10 according to the present invention may result in significantly reduced forces at the surgical port, which in turn reduces skin/tissue trauma for the patient. In MIS tools currently on the market, placement of the tool input joint between the handle and the tool shaft makes the actuation of the tool dependent on the presence of an external ground reference, which can provide reaction loads, or in other words, close the load loop. The user applies a torque at the tool handle, and the surgical port acts as the external ground reference to provide the balancing loads necessary to allow the handle to tip downwards, which then tips the end effector downwards. The load loop, in this case, comprises the tool handle, tool shaft, surgical port, patient's body, the bed that the patient's body rests on, the ground that supports the bed, the ground that the surgeon (user) stands on, the surgeon's body, the surgeon's forearm, and the surgeon's hand that grips the tool handle—in that order. As such, all the tool actuation loads during articulation of input and output joints necessarily flow through the surgical port and patient's body. These loads are particularly detrimental to the skin and tissue surrounding the surgical port, in the case of young or elderly patients.

In contrast, the tool 10 according to the present invention provides a common ground frame 18 that bridges the tool shaft 22 and the user's forearm. Employing the user's forearm as a ground reference locally closes the load loop associated with the wrist DoF actuation forces. Here, the load loop comprises the handle 24, the input joint or VC mechanism 16, the frame 18, the arm attachment member 20, and the user's arm and hand. Contrary to existing hand-held tools, this entirely eliminates the need for an external ground reference, such as the surgical port and patient's body, to provide reaction loads.

Figure 21:
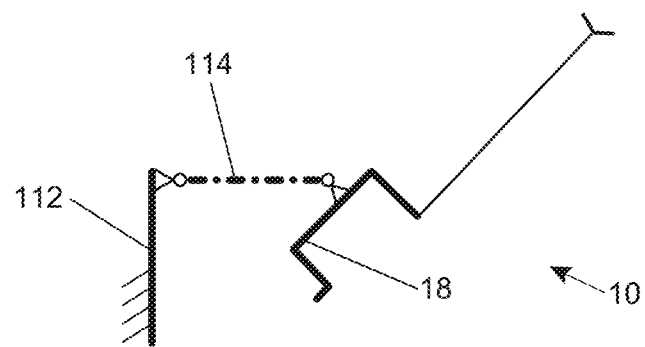
FIG. 21 is a schematic illustration of an alternative attachment of a minimal access tool according to the present invention to a support structure other than the user's forearm.
Figure 22A:
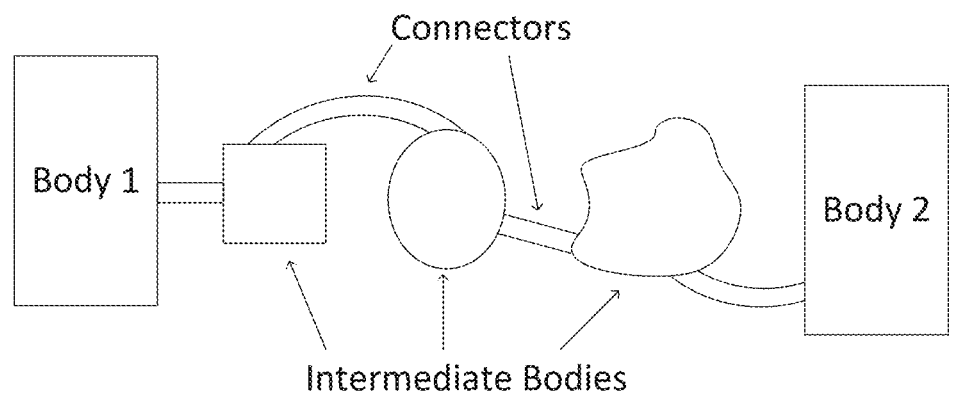
FIGS. 22A and 22B illustrate example of a schematic of serial kinematic pathways.
Figure 22B:
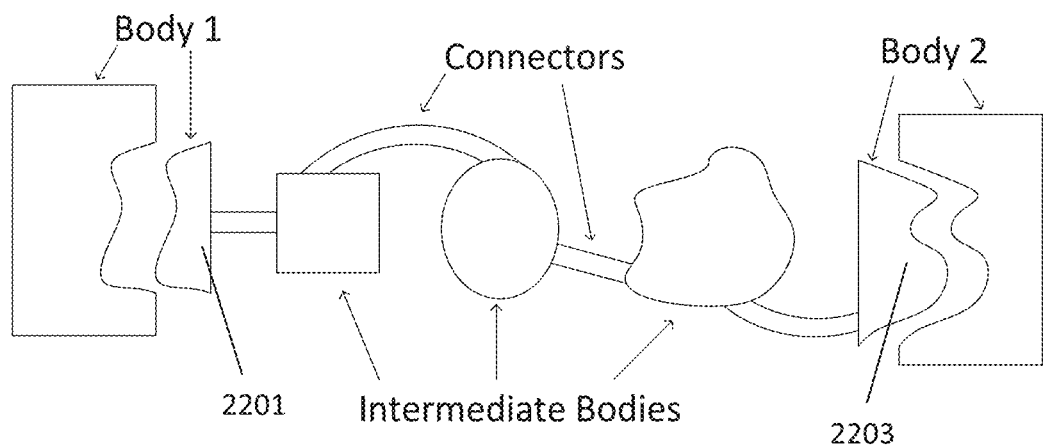
Figure 23:
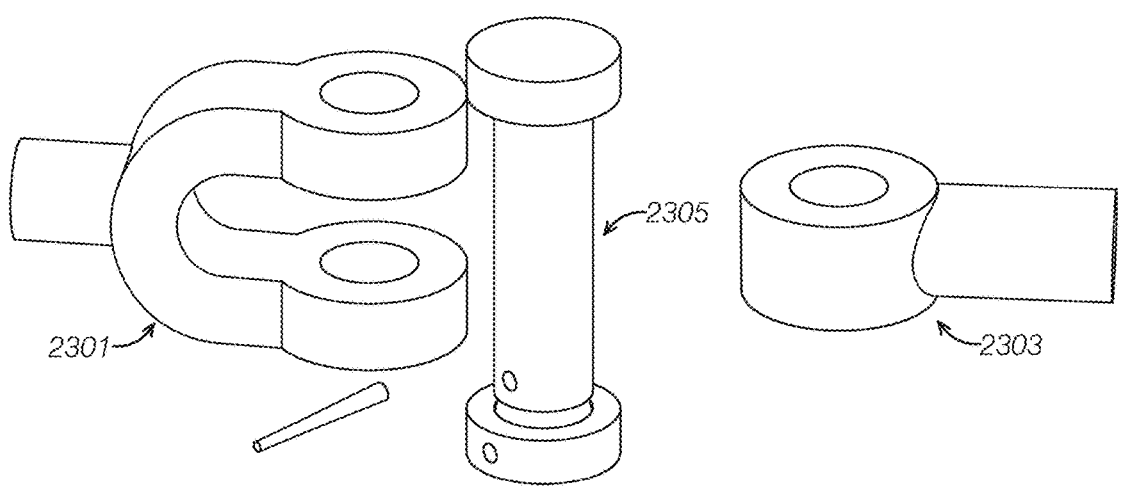
FIG. 23 is an example of an exploded view of a joint that, when assembled, allows a single rotational degree of freedom but constrains the other five degrees of freedom.
Figure 24:
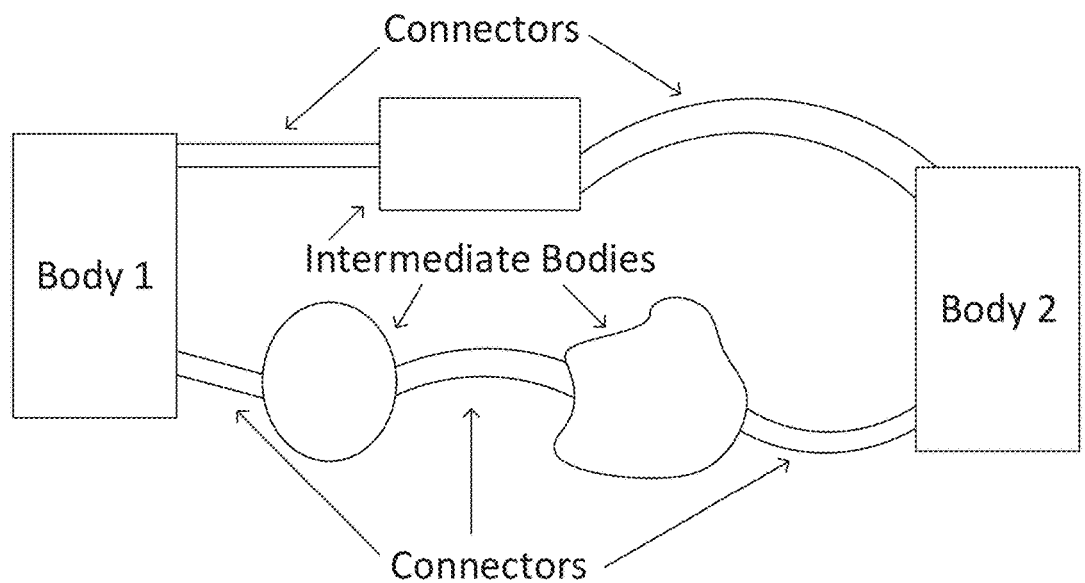
FIG. 24 illustrates an example of a parallel design, in which two independent pathways connect between body 1 and body 2.
Figure 25:
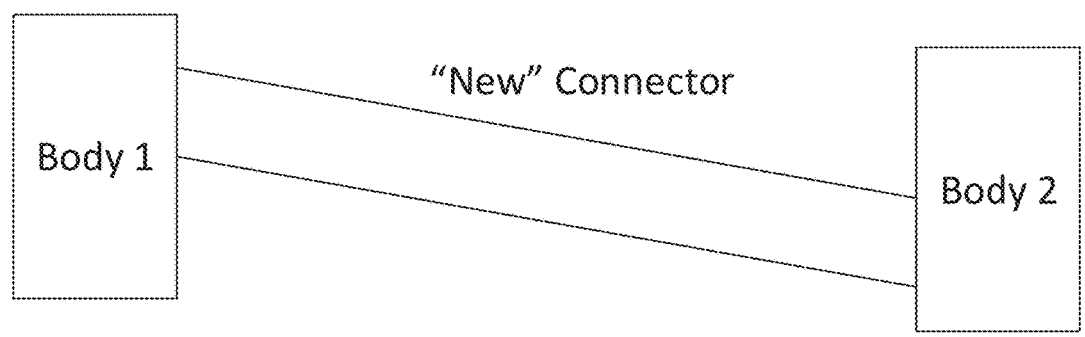
FIG. 25 shows a simplified version of a kinetic schematic such as the one shown in FIG. 22A, in which the multiple intermediate bodies and connectors are reduced to a single "new" pathway that may include these components.

Lastly, with reference to FIG. 21, instead of the frame 18 being attached to the user's forearm, the frame 18 may be mounted on a bed frame or other structure 112 external to the user's body via an interface mechanism 114 connected there between which may help support the weight of the tool 10. This interface mechanism 114 may generally provide 6 DoF between the external structure 112 and the frame 18 to avoid over-constraining or limiting the motion of the tool 10. The surgeon (user) can then place his/her arm into the arm attachment member 20 and guide the tool 10 as described above while the external structure 112 supports the weight of the tool 10.

While the articulation of an end effector 12, connected to the distal end of tool shafted via an output joint, using an input joint that may include a VC mechanism 16 is described above, in another application, a similar VC mechanism-based input joint may be used to articulate the tip of an endoscopic device. Such an arrangement would provide the user with an intuitive and ergonomic means for guiding the endoscopic device inside a patient's body.

While embodiments of the invention have been illustrated and described, it is not intended that these embodiments illustrate and describe all possible forms of the invention. It is understood that the features of various implementing embodiments may be combined to form further embodiments of the invention. The words used in the specification are words of description rather than limitation, and it is understood that various changes may be made without departing from the spirit and scope of the invention.

The PK mechanisms described above generally include two rotational degrees of freedom (generically, rotation 1 and rotation 2; or more specifically pitch and yaw). The nature of these PK mechanisms derived from the constraint map of FIG. 26 such that these two rotations are present with respect to a frame that may serve as the ground reference in a tool, device, machine, instrument, robot, etc. In any of these applications, there is often the practical need to transmit these rotations from or to the PK mechanism. For example, when the mechanism serves as an input interface, as discussed above, there may be a need to transmit the rotations from the mechanism to another point of interest. The latter could be a remote end effector, or inputs to a computer interface e.g. XY coordinates on a computer screen, or pitch and roll coordinates in a gaming system, etc. When the mechanism serves as an output interface (e.g., as described above for FIGS. 29A and 29B), there is a need to transmit rotations (and associated torques) to the mechanism from other points of interest (generally manual or powered actuators). Thus, the PK mechanisms presented here may generally be used along with a transmission system, as discussed above. This transmission system could be mechanical, hydraulic, pneumatic, electrical, and/or wireless. Some representative examples are shown using the PK mechanism embodiments in FIG. 1 (and embodiment 1) discussed above. Described herein are examples of transmission systems that may be used in conjunction with PK mechanisms based on the constraint map of FIG. 26. The unique attribute of any PK mechanism based on this constrain maps is that it presents the two rotations separated out as two individual rotations, pitch only and yaw only, about respective axes that are fixed with respect to the frame. These individual rotations can then be individually transmitted from the respective pulleys to other locations on the frame of the overall device/instrument/tool or vice versa.

Figure 57A:
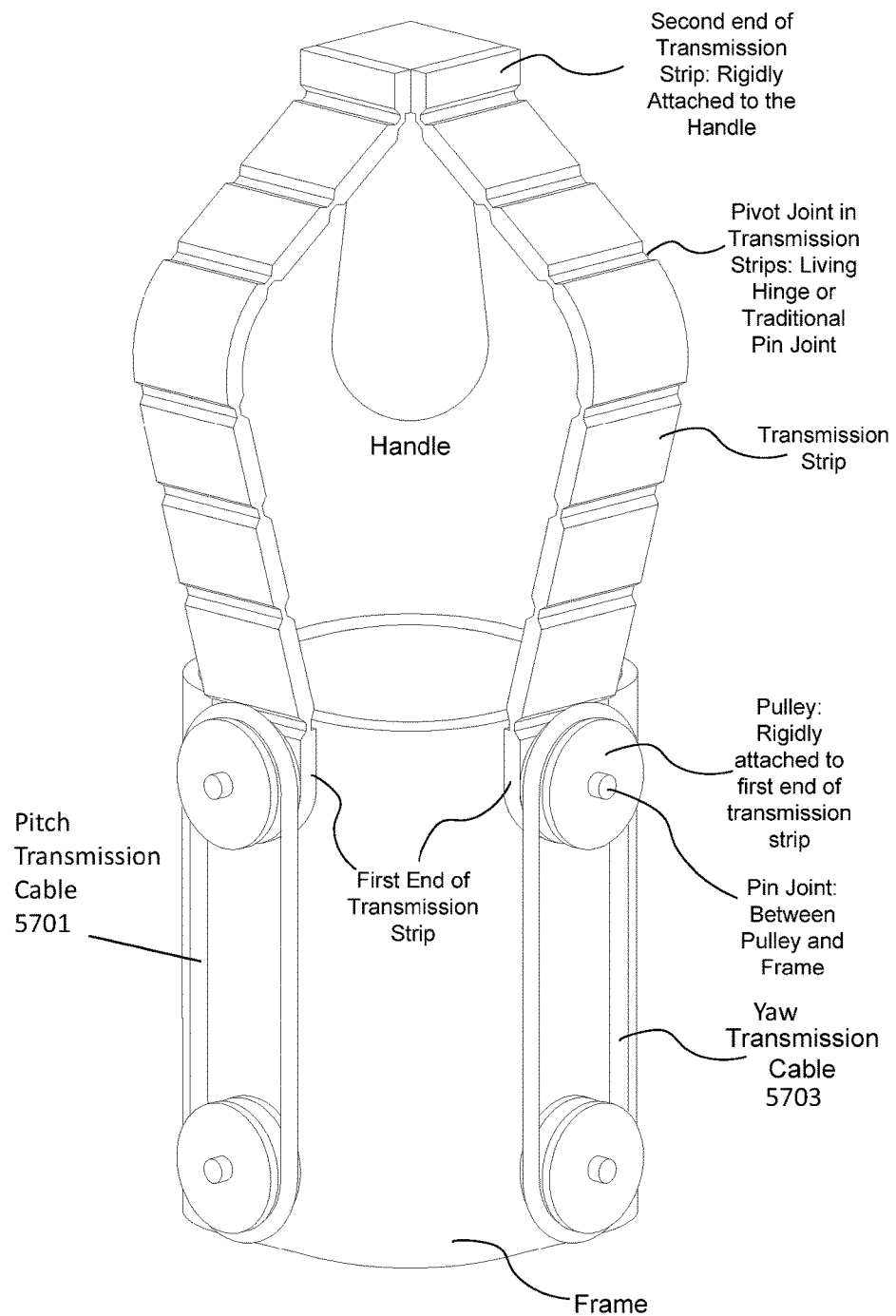
FIGS. 57A and 57B illustrate a parallel kinematic mechanism including a mechanical transmission (transmission cable or belt).
Figure 57B:
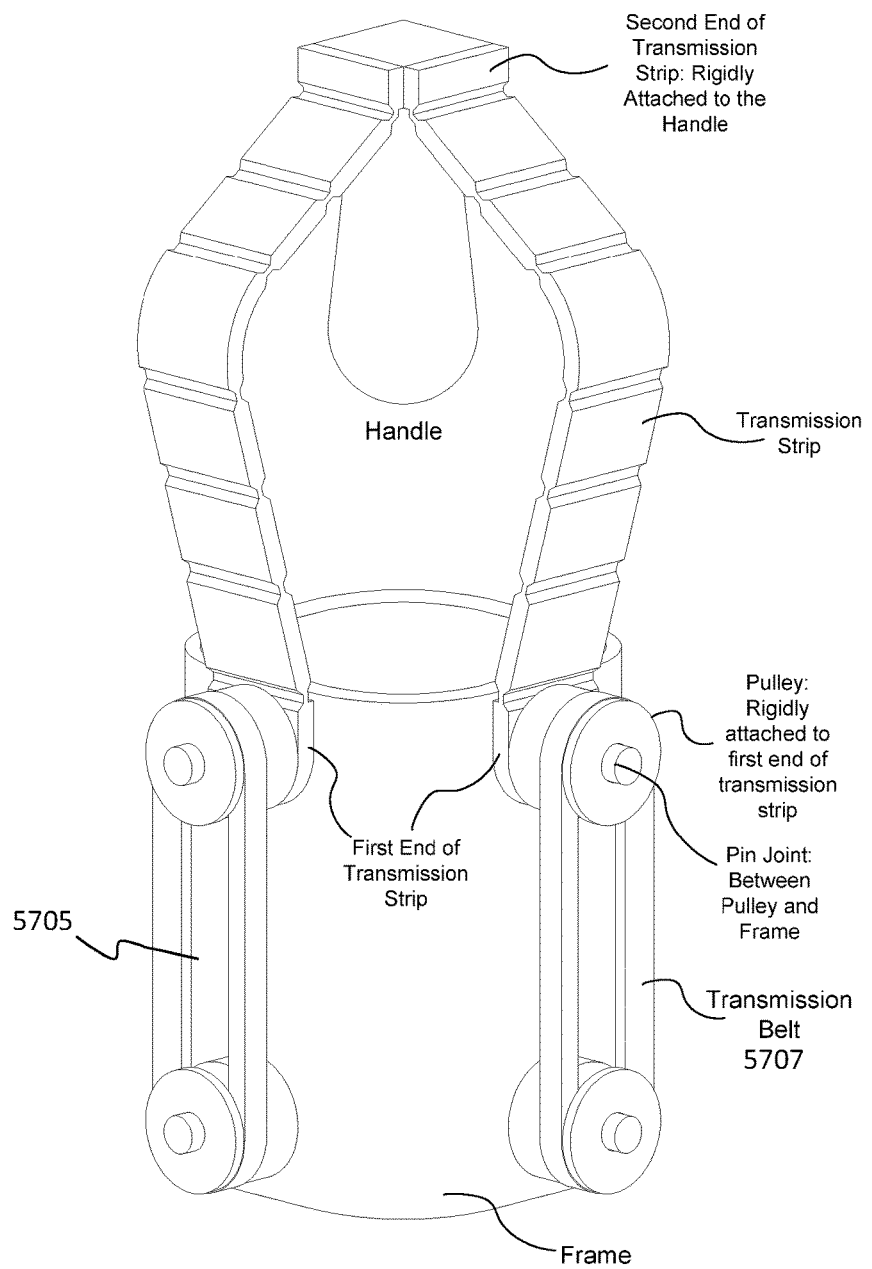

FIG. 57A illustrates a cable or pulley based transmission. Although FIG. 57A shows a simple cable-pulley transmission system for each rotation, it should be understood that the cable/pulley transmission system can be fairly sophisticated and be routed via complex paths to transmit rotations of the two pulleys in the PK mechanism to corresponding motions at a remote location on the frame. Transmission cables, pitch cable 5701 and yaw cable 5703 separately transmit pitch and yaw rotations from the mechanism. Similarly, FIG. 57B illustrates a belt/pulley based transmission that is similar to the previous case, but includes a pair of belts 5705, 5707 that transfer the pitch and yaw rotations separately. The belts may be rubber belts, timing belts, metal belts, or metal links based chain, etc. Although FIG. 57B shows a simple belt-pulley transmission system for each rotation, it should be understood that the belt-pulley transmission system can be fairly sophisticated and be routed via complex paths to transmit rotations of the two pulleys in the mechanism to corresponding motions at a remote location on the frame.

Figure 58:
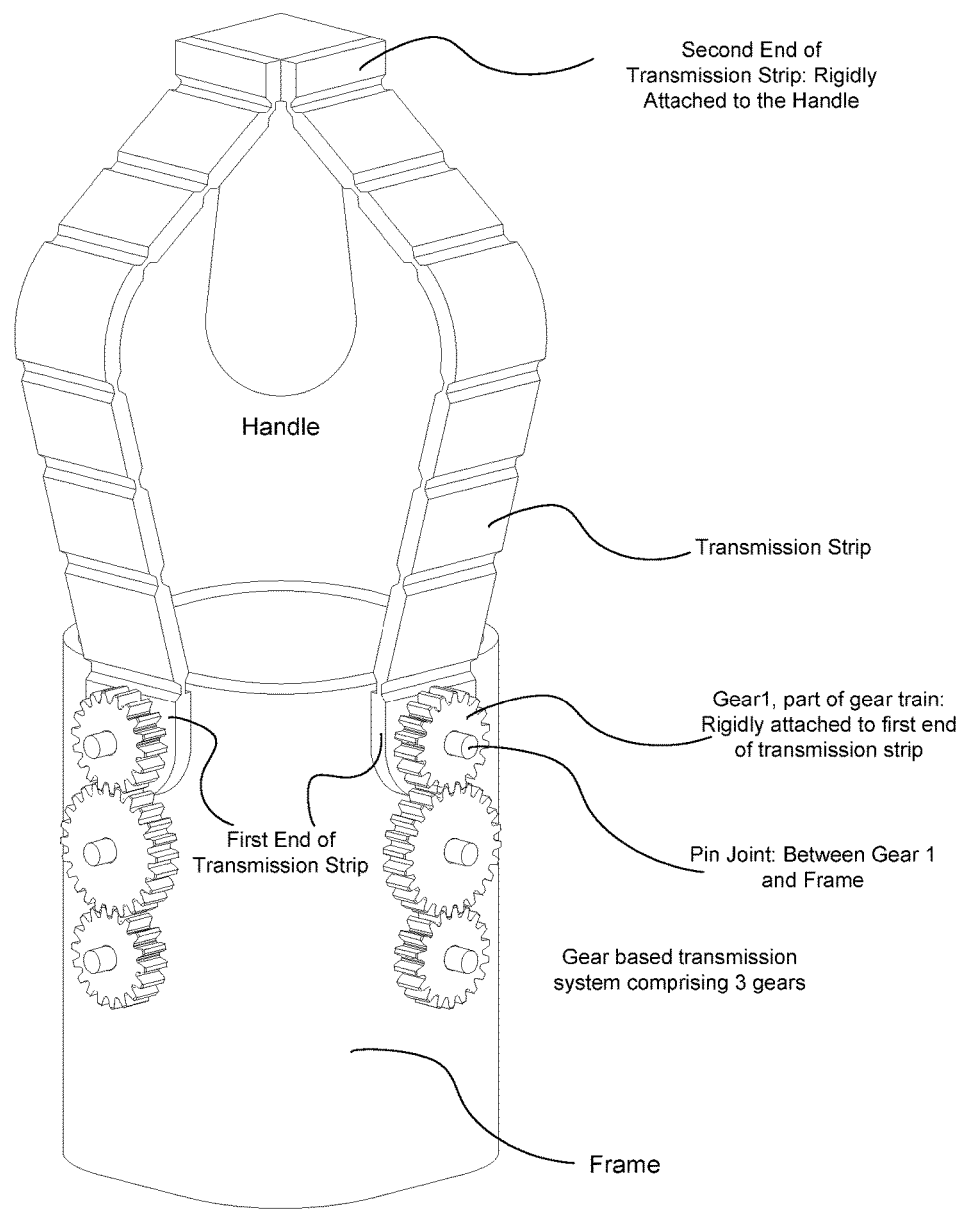
FIG. 58 shows an example of a parallel kinematic mechanism including a gear-based transmission system.

A gear-train based transmission may also be used, as illustrated in FIG. 58. Although FIG. 58 shows a simple gear-train based transmission system for each rotation, it should be understood that the gearing can be fairly sophisticated (e.g. be in the form of a gearbox) and be packaged along complex paths to transmit rotations of the two pulleys in the mechanism to corresponding motions at a remote location on the frame. Any of the transmission systems described herein (e.g., pulley, belt, gear, hydraulic, etc.) may be combined. For example, one can envision a transmission system that transmit the yaw and pitch rotations of the mechanism via separate transmission paths, each path comprising pulleys, belts, gears, hydraulics, pneumatics, electronics, wireless etc.

Figure 59:
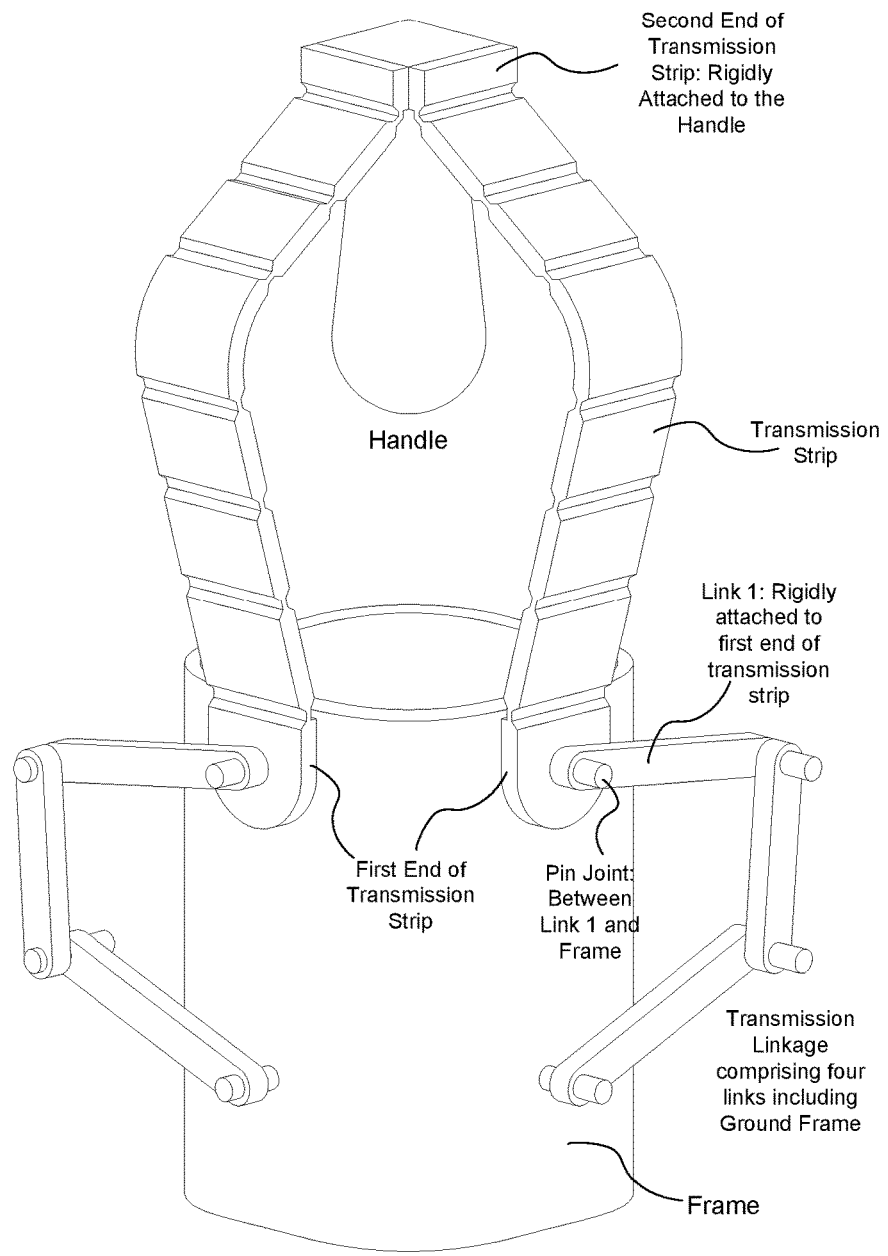
FIG. 59 shows an example of a parallel kinematic mechanism including a transmission linkage.

FIG. 59 illustrates a linkage mechanism based transmission. In FIG. 59, the linkage is a simple four bar mechanism based transmission system for each rotation. It should be understood that the linkage can be fairly sophisticated (e.g. six bar, eight bar mechanisms, etc.) and be packaged along complex paths to transmit rotations of the two pulleys in the mechanism to corresponding motions at a remote location on the frame.

Figure 60:
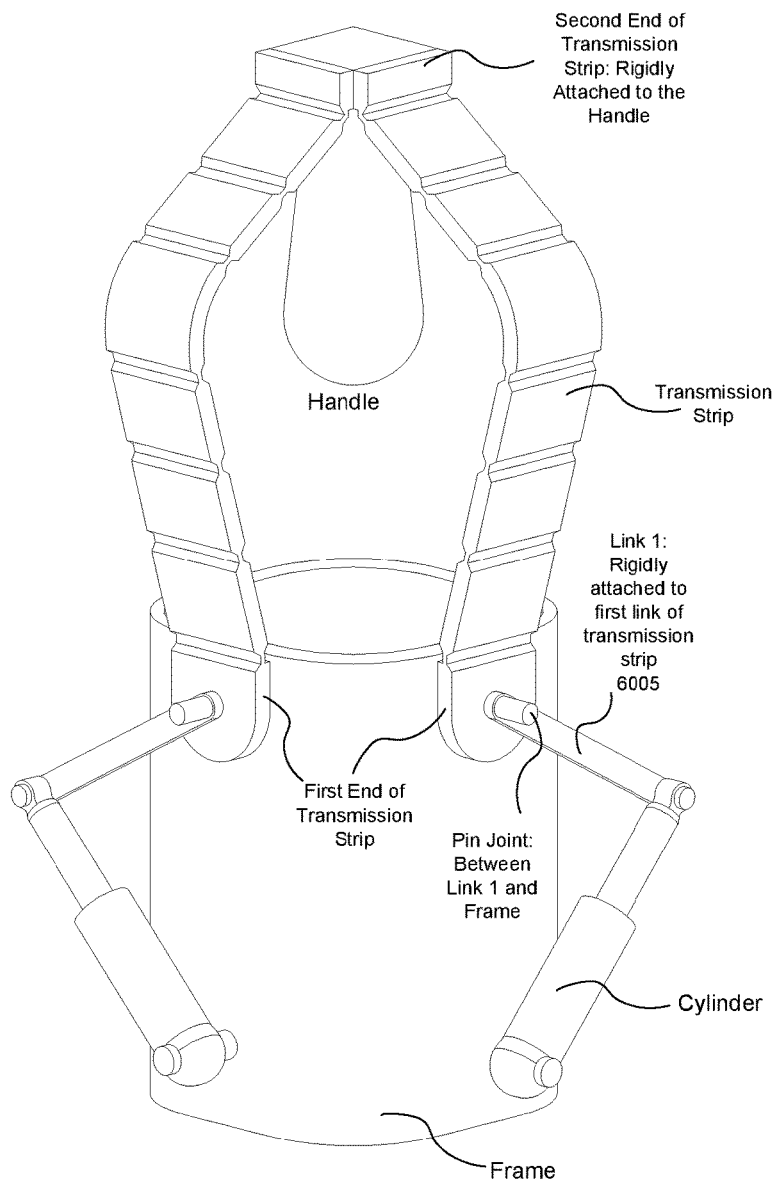
FIG. 60 shows an example of a parallel kinematic mechanism including a pneumatic/hydraulic transmission system.

The variation in FIG. 60 shows a pneumatic/hydraulic transmission. In FIG. 60, the transmission is a simple configuration where each rotation of the PK mechanism is converted into fluid pressure via a cylinder. This fluid flow (in case of hydraulics) or pressure (in case of pneumatics) can be transmitted to any location via hoses/pipes etc. The fluid flow/pressure thus transmitted can be used to recreate/regenerate force and/or motion at a remote location. This is simply one representative example of how fluid based transmission may be used. It is noted that the illustrated system is actually a combination of hydraulic/pneumatic transmission elements and linkage based transmission because a linkage is used in this example to convert the rotational motion of the mechanism (at Link 1 6005, for example) to translation motion at a piston-cylinder that is used to generate fluid flow or pressure.

Figure 61:
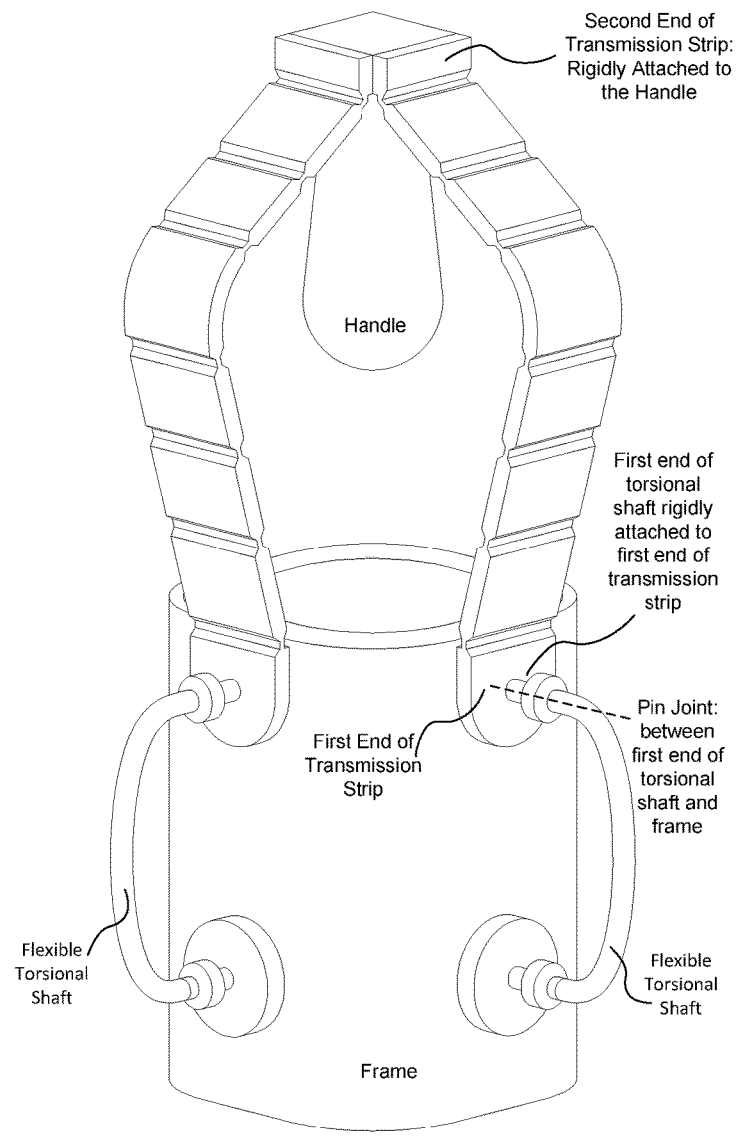
FIG. 61 shows an example of a parallel kinematic mechanism with a transmission system including flexible torsional shafts.
Figures 62A, 62B:
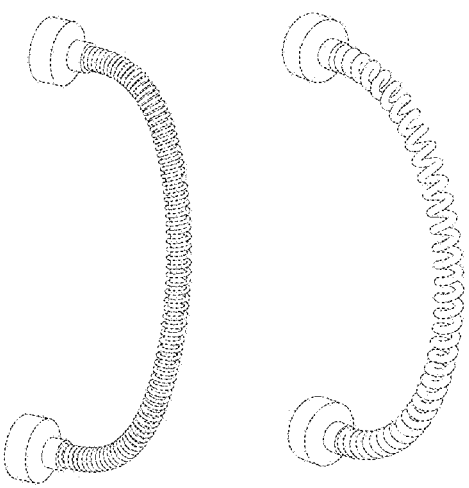
FIGS. 62A and 62B illustrate torsional shafts.

FIG. 61 illustrates an example of a flexible torsional shaft based transmission. In this example, each rotation of the mechanism (i.e. of the pitch and yaw pulley with respect to the frame) is individually transmitted to corresponding pulleys located elsewhere on the frame. The flexible torsional shaft here is similar to that discussed above in relation to FIG. 53. The torsional shaft can easily bend (within certain limits dictated by its construction) while maintaining high torsional stiffness about its center axis even after bending. The latter helps transmit rotational motions about the center axis of the flexible shaft. FIGS. 62A and 62B illustrate examples of construction of the flexible torsional shaft.

Figure 63:
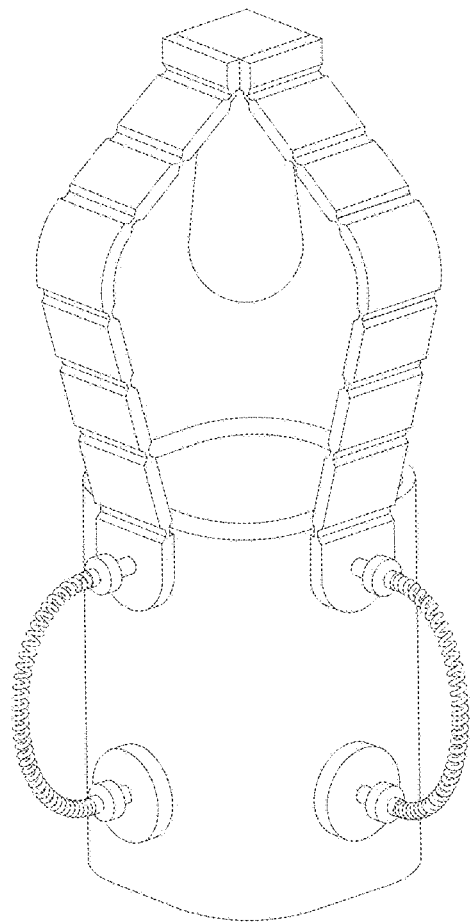
FIG. 63 shows another example of a parallel kinematic mechanism with a transmission system including flexible torsional shafts.

FIG. 63 shows another example of a torsional shaft transmission system used along with a PK mechanism.

Figure 64:
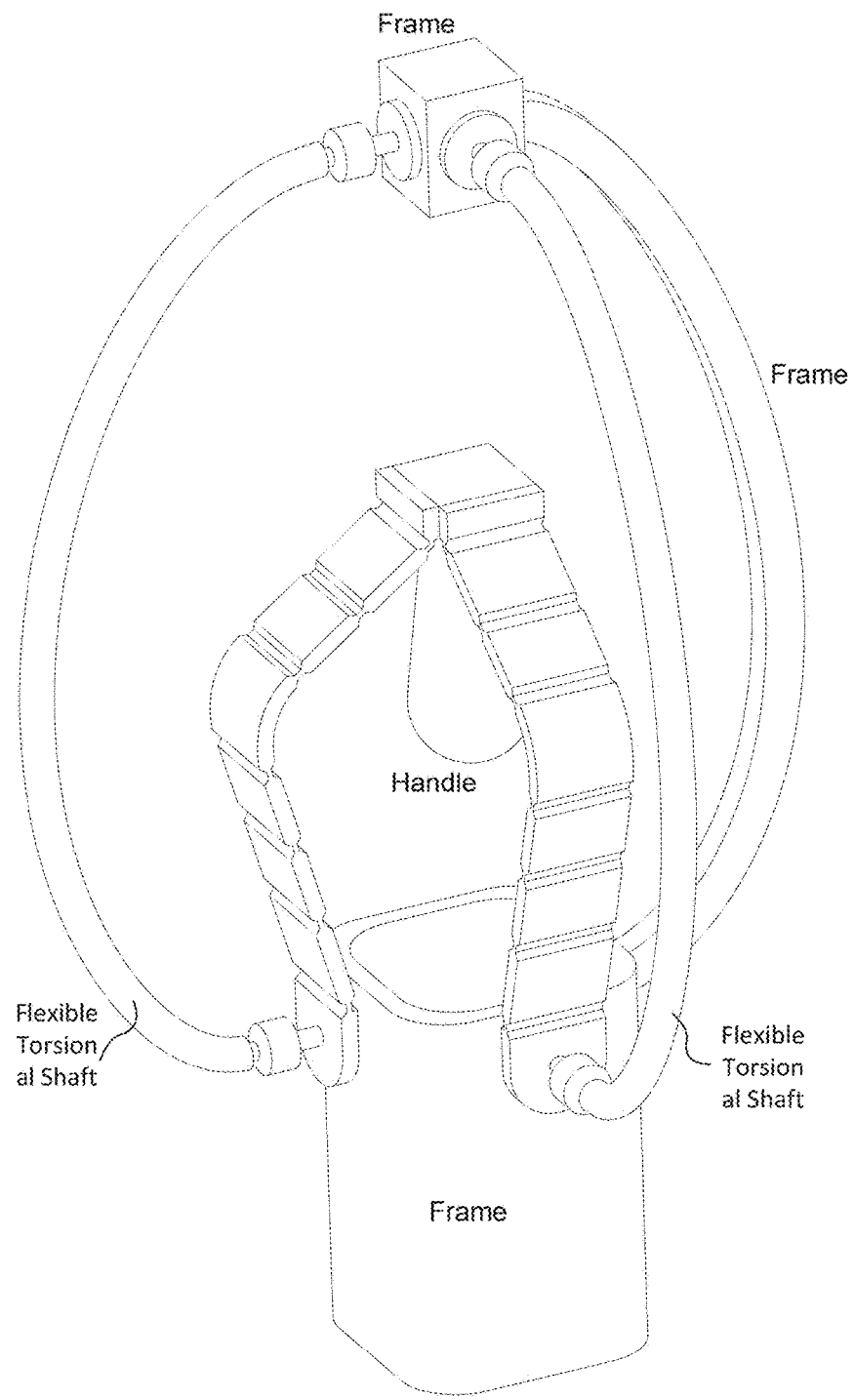
FIG. 64 shows an example of a parallel kinematic mechanism with a transmission system including flexible torsional shafts and a frame that extends both proximally and distally from the parallel kinematic mechanism.
Figures 65A, 65B:
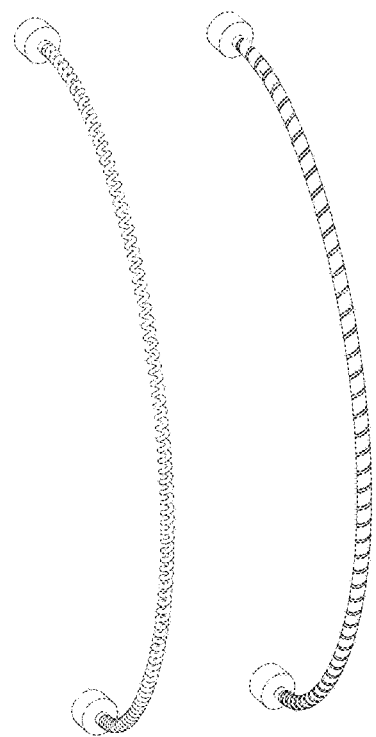
FIGS. 65A and 65B show examples of the flexible torsional shafts.
Figure 66:
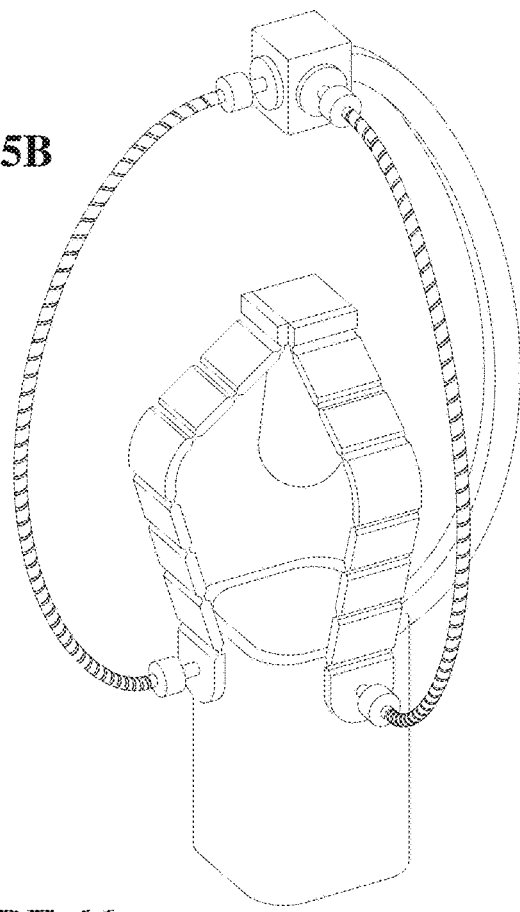
FIGS. 66 and 67 show examples of a parallel kinematic mechanism similar to that shown in FIG. 64.
Figure 67:
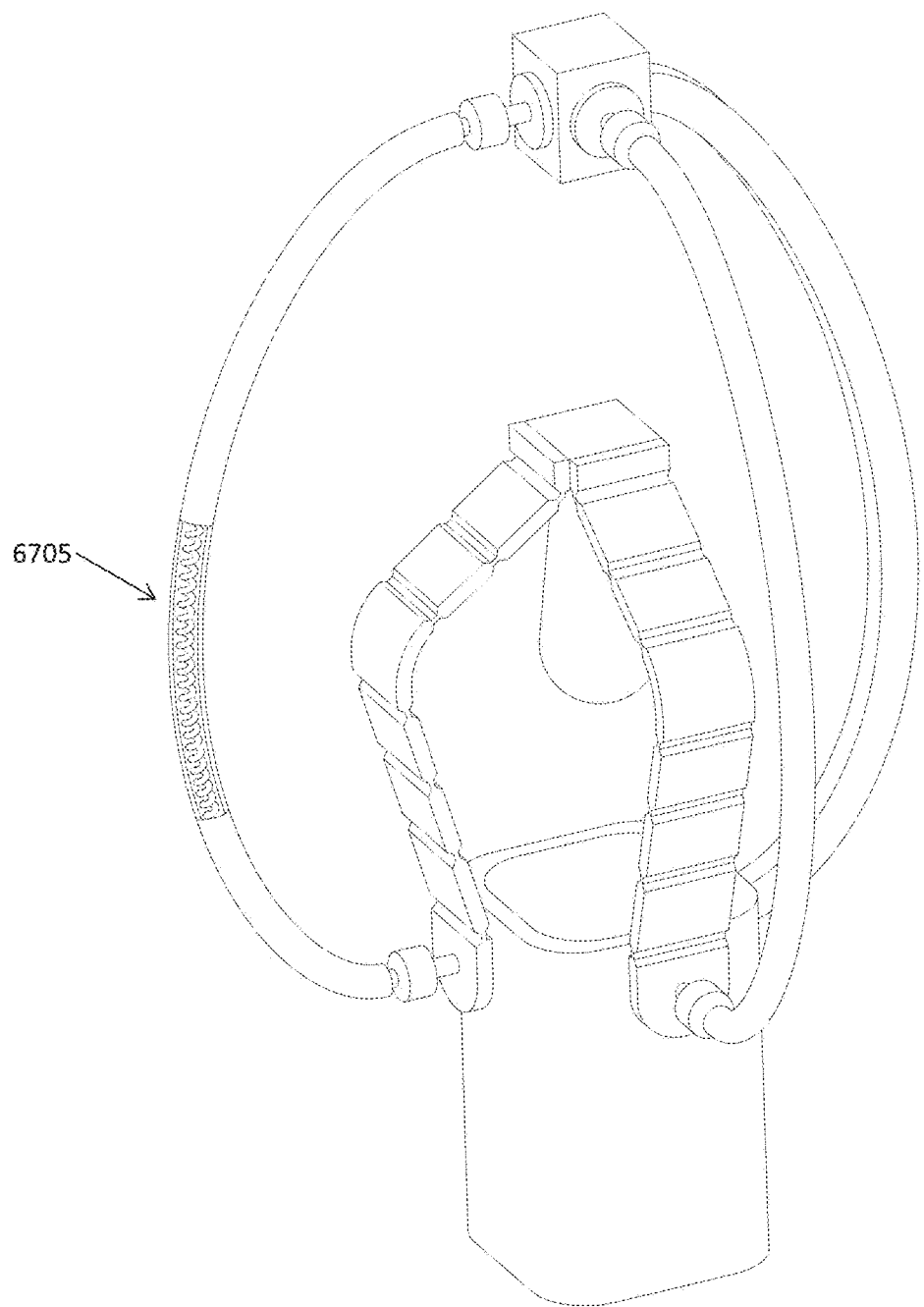

FIG. 64 shows a similar transmission concept with a slightly different frame geometry. Here the frame has an extended shape and geometry to convey the fact that the frame can be of any arbitrary size and shape. The flexible torsional shafts simply need to be long enough to reach the appropriate point of interest on the frame, where the rotations from the PK mechanism are to be transmitted (or vice versa). Similarly, FIGS. 65A and 65B illustrate examples of the construction of flexible torsional shafts, and this transmission system is also illustrated in FIGS. 66 and 67. FIG. 67 shows an embodiment of a PK mechanism with construction details 6705 of the flexible torsional shaft shown. In this example, the flexible torsional shaft is shown with a partial sectional view 6705 that includes the flexible shaft as well as a sheath that covers the shaft. Such cover may provide protection against debris etc., ensure that the flexible shaft itself does not pinch or damage any other component that it comes in contact with, and provide support to the flexible shaft so that it can transfer torque and rotational motion more effectively.

One attribute of the flexible torsional shaft based transmission is that the frame itself does not have to be rigid. Even if the frame is adjustable in shape, the flexible torsional shafts simply bend and take a new shape from one location on the frame to another location on the frame, all the while transmitting rotations about its center axis. This can be of practical use in an application where it is desirable to keep the frame itself flexible/adjustable, rather than completely rigid. Examples of flexible/adjustable frames include frames that can be bent/adjusted into any desired shape, and retain their shape due to, e.g., friction at joints along the length of this construction.

Figure 68:
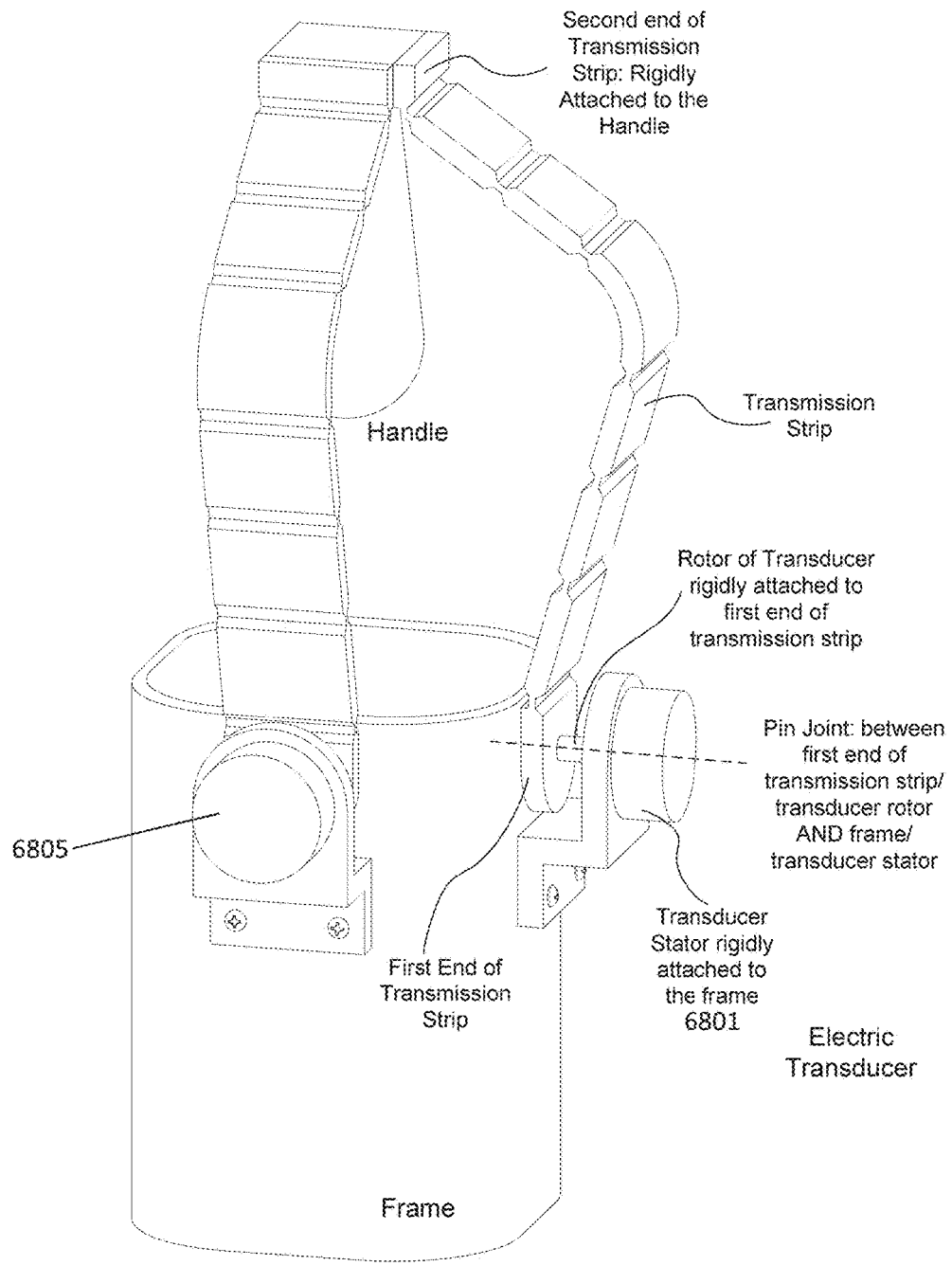
FIG. 68 shows an example of a parallel kinematic mechanism with a transmission system including an electrical transducer.

FIG. 68 illustrates and example of an electrical transmission that may be used. In FIG. 68 the pitch and yaw pulleys of the mechanism (more generically, intermediate bodies A and B, respectively) are coupled with electrical transducers 6805, 6801 such as actuators (motor, etc.) or sensors (optical encoders, potentiometers, etc.). The transducer may have a housing/stator and a rotor, and a pivot joint axis between the rotor and stator. In the transmission of FIG. 68, the rotor of the transducer is rigidly attached to the first end of the transmission strip while the stator of the transducer is rigidly attached to the frame (therefore the rotor and first end of the transmission strip are equivalent to a single rigid body and the stator and frame are equivalent to another rigid body). If the transducer is a sensor, then any rotation of the first end of the transmission strip (or equivalently intermediate bodies A or B) with respect to the frame gets converted into an electrical signal. This electrical signal may then be transmitted via wires or wirelessly to a computer or electrical system, where this signal may be used to control a human interface device such as mouse or to control a gaming system etc., or these signals can serve as the inputs to a computer controlled robotic system. For example, the PK mechanism may become part of a joy-stick.

Alternatively, the electrical transducer may be a motor that transmits torques and rotations to the PK mechanism, an example of this was shown in FIGS. 29A and 29B.

Note that instead of rotary transducers as shown in FIG. 68, one could first employ a linkage mechanism such as show in FIGS. 59 and 60 to convert rotary motion into translation motion between the piston/cylinder, and then employ a translational transducer with the piston cylinder.

Although the transmission systems described above are shown in conjunction with the exemplary PK mechanism of FIGS. 12 and 13, these transmission methods are equally relevant to all other embodiments of the PK mechanism described here, and generally with respect to those encompassed by the constraint map of FIG. 26. Further, although various transmission systems are presented separately, combination of these transmission systems may be used, such as "gearing system with electrical sensors" or "linkage mechanisms with cable/pulley drive", etc.

Figure 69A:
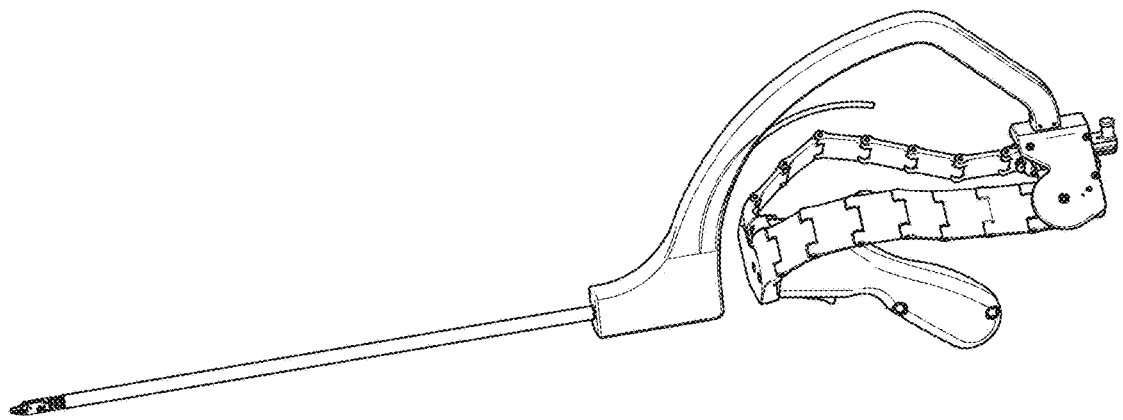
FIGS. 69A and 69B show side perspective views of one variation of a parallel kinematic mechanism configured as a minimally invasive tool having an output joint connected to the input joint of the parallel kinematic mechanism via a transmission.
Figure 69B:
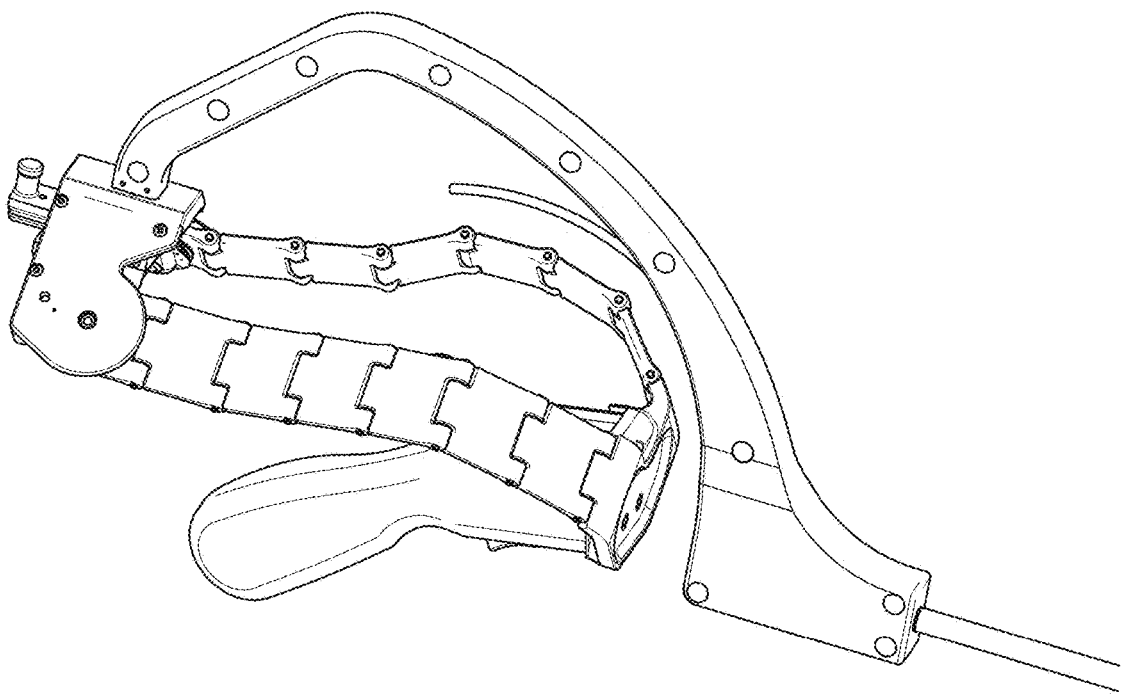

FIGS. 69A and 69B illustrate exemplary minimal access surgical tools including an end effector that is controlled using a parallel kinematic (PK) mechanism apparatuses based on a constraint map focusing on articulation motion (i.e. two orthogonal rotations) in which there are at least two independent and parallel paths between a frame and a handle. The first path includes a first intermediate body that is connected to the frame by a first connector and to the handle by a third connector. The second path includes a second intermediate body that is connected to the handle by a second connector and to the handle by a fourth connector. The first connector and the fourth connector are both compliant (allow rotation) in a first rotational direction and stiff (restrict rotation) in a second rotational direction. The second and third connectors allow rotation in the second rotational direction and restrict rotation in the first rotational direction. In some variations, the first and second rotational directions may be orthogonal to each other (e.g., the first rotational direction may be pitch and the second rotational direction yaw), but do not have to be. For example, the angle between these rotational directions may be between 30 and 150 degrees.

In this example, the PK mechanism of the apparatus includes a virtual center of rotation, but it does not have to. In FIGS. 69A and 69B, the virtual center (VC) is configured to be positioned at the user's wrist joint when the user's hand holds the handle and forearm interfaces with the arm attachment member of the frame.

Figure 70:
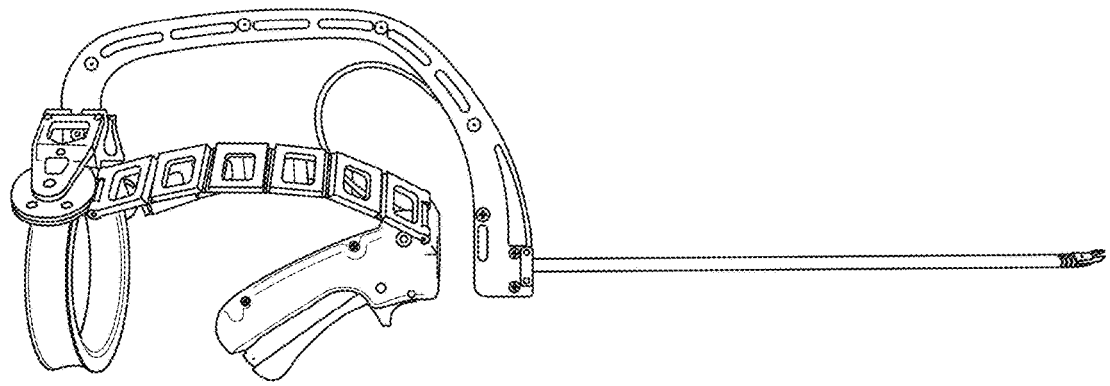
FIG. 70 is a side perspective view of another example of a parallel kinematic mechanism configured as a minimally invasive tool.
Figure 71A:
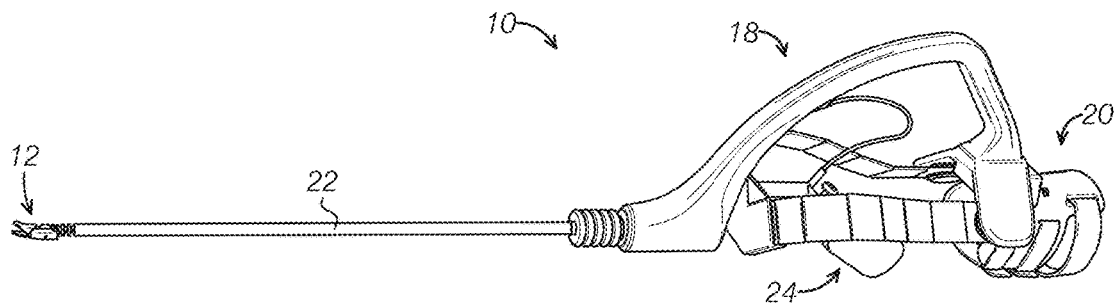
FIGS. 71A and 71B show side perspective views of a parallel kinematic mechanism configured as a minimally invasive tool.
Figure 71B:
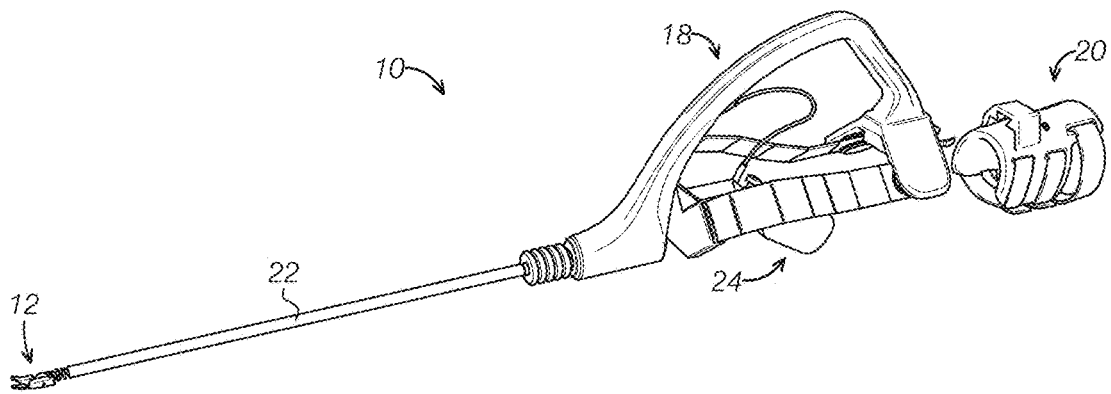

FIGS. 70, 71A and 71B illustrate two additional exemplary minimal access surgical tools including an end effector that is controlled using a parallel kinematic (PK) mechanism apparatuses based on a constraint map focusing on articulation motion. Each of these variations includes a PK mechanism consistent with the constraint map of FIG. 26 that is similar to that shown in FIGS. 12 and 13 as discussed above.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative teams, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A parallel kinematic (PK) mechanism having at least two rotational degrees of freedom between a handle and a frame, the PK mechanism comprising:
   the frame;
   the handle;
   an input joint having at least two independent paths for transmission of motion coupling the handle to the frame, wherein the at least two independent paths comprise a first path and a second path;
   a first intermediate body in the first path that is connected to the frame by a first connector and to the handle by a third connector;
   a second intermediate body in the second path that is connected to the frame by a second connector and to the handle by a fourth connector;
   wherein the first connector and the fourth connector both allow rotation in a first direction and restrict rotation in a second direction;
   further wherein the second and third connectors allow rotation in the second direction and restrict rotation in the first direction.

2. The parallel kinematic mechanism of claim 1, wherein an angle between an axis of rotation of the first direction and an axis of rotation of the second direction is between 30 and 150 degrees.

3. The parallel kinematic mechanism of claim 1, wherein an axis of rotation of the first direction is orthogonal to an axis of rotation of the second direction.

4. The parallel kinematic mechanism of claim 1 wherein an axis of rotation of the first direction and an axis of rotation of the second direction intersect in a virtual center of rotation, further wherein the virtual center of rotation is located in a vacant space devoid of any other components of the parallel kinematic mechanism or attached to the parallel kinematic mechanism.

5. The parallel kinematic mechanism of claim 4, wherein the virtual center of rotation coincides with a center of a user's articulating joint when the user interfaces with the handle.

6. The parallel kinematic mechanism of claim 4, wherein the virtual center of rotation coincides with a center of a user's wrist joint when the user is holding the handle.

7. The parallel kinematic mechanism of claim 1 configured as a portion of a minimally invasive tool further comprising a tool shaft having a proximal end and a distal end, wherein the proximal end of the tool shaft is connected to the frame.

8. The parallel kinematic mechanism of claim 7, wherein the minimally invasive tool further comprises an output joint with at least two rotational degrees of freedom between an end effector and the distal end of the tool shaft wherein the output joint is coupled to the input joint via a transmission system to correlate and transmit the at least rotations of the input joint to the at least two rotational degrees of freedom of the output joint.

9. The parallel kinematic mechanism of claim 7 wherein the minimally invasive tool further comprises an end effector connected to the tool shaft via an output joint having at least two rotational degrees of freedom between the end effector and the distal end of the tool shaft, wherein the output joint is coupled to the input joint via a transmission system to correlate and transmit rotations of the handle with respect to the frame to corresponding rotations of the end effector with respect to the tool shaft.

10. The parallel kinematic mechanism of claim 1 further comprising an output joint wherein the output joint is coupled to the input joint via a purely mechanical transmission system configured to correlate and transmit rotations of the first and second intermediate bodies to the output joint.

11. The parallel kinematic mechanism of claim 1 further comprising an output joint wherein the output joint is coupled to the input joint via an electromechanical transmission system configured to correlate and transmit rotations of the first and second intermediate bodies to the output joint.

12. The parallel kinematic mechanism of claim 1 further comprising an output joint wherein the output joint is coupled to the input joint via a fluidic transmission configured to correlate and transmit rotations of the first and second intermediate bodies to the output joint.

13. The parallel kinematic mechanism of claim 1, wherein the frame is configured to interface with the forearm of a user.

14. The parallel kinematic mechanism of claim 1, wherein the first and second intermediate bodies comprises pulleys.

15. The parallel kinematic mechanism of claim 1, wherein the first connector is a first pivot joint, the second connector is a second pivot joint, the third connector is a first flexure transmission strip and the fourth connector is a second flexure transmission strip.

16. The parallel kinematic mechanism of claim 1, wherein the input joint comprises a third independent path for transmission of motion coupling the handle to the frame, wherein the third independent path operates in parallel with the first and second paths;
   a third intermediate body in the third independent path that is connected to the frame by a fifth connector and to the handle by a sixth connector;
   wherein the fifth connector allows rotation in the first direction and restricts rotation in the second direction and the sixth connector allows rotation in the second direction and restricts rotation in the first direction.

17. The parallel kinematic mechanism of claim 1, wherein the first path and the second path allow translation along a third direction orthogonal to first and second directions.

18. The parallel kinematic mechanism of claim 1, wherein the first path or the second path or both the first path and the second path constrain(s) rotation about a third direction orthogonal to first and second directions.

19. A parallel kinematic (PK) mechanism having at least pitch and yaw rotational degrees of freedom between a handle and a frame, the PK mechanism comprising:
   the frame;
   the handle;
   an input joint having at least two independent paths for transmission of motion coupling the handle to the frame, wherein the at least two independent paths comprise a first path and a second path;
   a first intermediate body comprising a first pulley in the first path that is connected to the frame by a first connector comprising a first pulley pin and to the handle by a third connector comprising a first transmission strip;
   a second intermediate body comprising a second pulley in the second path that is connected to the frame by a second connector comprising a second pulley pin and wherein the second intermediate body is connected to the handle by a fourth connector comprising a second transmission strip;
   wherein the first pulley pin allows rotation in a pitch direction and restricts rotation in a yaw direction, and the second transmission strip is compliant in bending in the pitch direction and has a high stiffness in bending in the yaw direction;
   further wherein the second pulley pin allows rotation in the yaw direction and restricts rotation in the pitch direction and the first transmission strip is compliant in the yaw direction and has high stiffness in bending in the pitch direction.

20. The parallel kinematic mechanism of claim 19, wherein the first and second transmission strips comprise a plurality of rigid segments serially connected by hinged connections.

21. The parallel kinematic mechanism of claim 19, wherein the first and second transmission strips comprise a plurality of rigid segments and a plurality of hinges, wherein each rigid segment is hinged to an adjacent rigid segment by a hinge from the plurality of hinges, and wherein each hinge has an axis of rotation that is parallel to an axis of rotation of each hinge in the plurality of hinges, and wherein the hinges can be traditional hinges or living hinges or a combination thereof.

22. The parallel kinematic mechanism of claim 19, wherein a first end of the first transmission strip is attached to the handle and an opposite end of the first transmission strip is attached to the first pulley; further wherein the first end of the second transmission strip is attached to the handle and an opposite end of the second transmission strip is attached to the second pulley.

23. The parallel kinematic mechanism of claim 19, wherein the first and second transmission strips allow translation along a third direction that is orthogonal to the first direction and the second direction.

24. The parallel kinematic mechanism of claim 19, wherein the first path, or the second path, or the first and second paths constrain rotation along a third direction that is orthogonal to the first direction and the second direction.

25. The parallel kinematic mechanism of claim 19, wherein the first and second transmission strips comprise a plurality of rigid segments and a plurality of hinges, wherein each rigid segment is hinged to an adjacent rigid segment by a hinge from the plurality of hinges, and wherein at least some of the hinges comprise living hinges.

26. A parallel kinematic (PK) mechanism having at least pitch and yaw rotational degrees of freedom between a handle and a frame comprising:
   a frame;
   a handle comprising a plate;
   an input joint having at least two independent paths for transmission of motion coupling the handle to the frame, wherein the at least two independent paths comprise a first path and a second path;
   a first intermediate body comprising a first plate in the first path that is connected to the frame by a first connector comprising a first plurality of transmission strips and to the handle by a third connector comprising a third plurality of transmission strips;
   a second intermediate body comprising a second plate in the second path that is connected to the frame by a second connector comprising a second plurality of transmission strips and to the handle by a fourth connector comprising a fourth plurality of transmission strips;
   wherein the first connector and the fourth connector both allow rotation in a pitch direction and restrict rotation in a yaw direction;
   further wherein the second and third connectors allow rotation in the yaw direction and restrict rotation in the pitch direction.

27. The parallel kinematic mechanism of claim 26, wherein the first plurality of transmission strips and the fourth plurality of transmission strips are compliant in bending in the pitch direction and have a high stiffness in bending about the yaw direction and wherein the second plurality of transmission strips and the third plurality of transmission strips are compliant in bending in the yaw direction and have a high stiffness in bending about the pitch direction.

28. The parallel kinematic mechanism of claim 26, wherein the each transmission strip in the first plurality of transmission strips is rigidly attached at a first end to the first intermediate body and is rigidly attached at a second end opposite from the first end to the frame; and wherein each transmission strip in the third plurality of transmission strips is rigidly attached at a first end to the first intermediate body and is rigidly attached at a second send opposite from the first end to the handle.

29. A parallel kinematic (PK) mechanism having at least pitch and yaw rotational degrees of freedom between a handle and a frame comprising:
   a frame;
   a handle;
   an input joint having at least two independent paths for transmission of motion coupling the handle to the frame, wherein the at least two independent paths comprise a first path and a second path;

a first intermediate body comprising a pitch mount in the first path that is connected to the frame by a first connector comprising a pivot joint and to the handle by a third connector;

a second intermediate body comprising a yaw mount in the second path that is connected to the frame by a second connector comprising a pivot joint and to the handle by a fourth connector;

wherein the first connector and the fourth connector both allow rotation in a pitch direction and restrict rotation in a yaw direction;

further wherein the second and third connectors allow rotation in the yaw direction and restrict rotation in the pitch direction.

30. The parallel kinematic mechanism of claim 29, wherein the first intermediate body comprises a pulley rigidly coupled to the pitch mount and wherein the second intermediate body comprises a yaw pulley rigidly coupled to the yaw mount.

31. The parallel kinematic mechanism of claim 29, further wherein the first path, or the second path, or the first and the second paths constrain the handle or the member rigidly extending from the handle from rotating about a roll axis that is orthogonal to both the pitch and yaw axes.

32. The parallel kinematic mechanism of claim 29, further wherein the first path and the second path allow the handle or the member rigidly extending from the handle to translate along a roll axis that is orthogonal to both the pitch and yaw axes.

* * * * *